(12) United States Patent
Tsukui

(10) Patent No.: US 9,657,071 B2
(45) Date of Patent: May 23, 2017

(54) IGE PEPTIDE VACCINE

(71) Applicant: NIPPON ZENYAKU KOGYO CO., LTD., Koriyama-shi, Fukushima (JP)

(72) Inventor: Toshihiro Tsukui, Koriyama (JP)

(73) Assignee: NIPPON ZENYAKU KOGYO CO., LTD., Koriyama-Shi (JP)

(*) Notice: Subject to any disclaimer, the term of this patent is extended or adjusted under 35 U.S.C. 154(b) by 119 days.

(21) Appl. No.: 14/408,590

(22) PCT Filed: Jun. 18, 2013

(86) PCT No.: PCT/JP2013/066685
§ 371 (c)(1),
(2) Date: Dec. 17, 2014

(87) PCT Pub. No.: WO2013/191166
PCT Pub. Date: Dec. 27, 2013

(65) Prior Publication Data
US 2015/0203550 A1    Jul. 23, 2015

(30) Foreign Application Priority Data
Jun. 18, 2012 (JP) ................. 2012-136944

(51) Int. Cl.
| A61K 38/00 | (2006.01) |
| C07K 14/47 | (2006.01) |
| C07K 16/42 | (2006.01) |
| C07K 16/00 | (2006.01) |
| C07K 7/08 | (2006.01) |
| A61K 39/00 | (2006.01) |

(52) U.S. Cl.
CPC ............ C07K 14/47 (2013.01); A61K 39/001 (2013.01); A61K 39/0005 (2013.01); C07K 7/08 (2013.01); C07K 16/00 (2013.01); C07K 16/4291 (2013.01); *A61K 2039/505* (2013.01); *A61K 2039/552* (2013.01); *A61K 2039/57* (2013.01); *A61K 2039/575* (2013.01); *A61K 2039/577* (2013.01); *C07K 2317/52* (2013.01); *C07K 2317/526* (2013.01)

(58) Field of Classification Search
None
See application file for complete search history.

(56) References Cited

U.S. PATENT DOCUMENTS

| 6,811,782 | B1 * | 11/2004 | Wang ................. A61K 39/0008 424/185.1 |
| 6,913,749 | B2 | 7/2005 | Hellman |
| 8,298,547 | B2 * | 10/2012 | Brown ................... A61K 39/00 424/185.1 |
| 2002/0064525 | A1 | 5/2002 | Morsey et al. |
| 2003/0096369 | A1 * | 5/2003 | Morsey .................. C07K 16/00 435/69.3 |
| 2004/0156838 | A1 | 8/2004 | Klysner et al. |
| 2011/0300163 | A1 * | 12/2011 | Champion ......... A61K 39/0005 424/183.1 |

FOREIGN PATENT DOCUMENTS

| DK | WO 0220038 A2 * | 3/2002 | ......... A61K 39/0008 |
| JP | 1-299298 A | 12/1989 | |
| JP | 9-169795 A | 6/1997 | |
| JP | 2002-531064 A | 9/2002 | |
| JP | 2002-281984 A | 10/2002 | |
| JP | 2003-47482 A | 2/2003 | |
| JP | 2004-508028 A | 3/2004 | |
| JP | 2005-102701 A | 4/2005 | |
| JP | 2006-151880 A | 6/2006 | |
| WO | WO 9305810 A1 * | 4/1993 | ......... C07K 16/4291 |
| WO | WO 9526365 A1 * | 10/1995 | ......... A61K 39/0005 |
| WO | WO 9612740 A1 * | 5/1996 | ......... A61K 39/0008 |
| WO | WO 00/25722 A2 | 5/2000 | |
| WO | WO 02/20038 A2 | 3/2002 | |
| WO | WO 2010/067286 A2 | 6/2010 | |

OTHER PUBLICATIONS

Colman, P.M., Research in Immunology, 1994, 145:33-36.*
Taylor et al., Biochemistry. Jan. 27, 2009;48(3):558-62. doi: 10.1021/bi8019993.*
Partial Supplementary European Search Report issued Jan. 11, 2016, in European Patent Application No. 13806792.1.
Extended European Search Report issued Mar. 17, 2016, in European Patent Application No. 13806792.1.
Office Action issued Oct. 27, 2015, in Japanese Patent Application No. 2014-521475.
International Search Report, issued in PCT/JP2013/066685, dated Sep. 24, 2013.
Written Opinion of the International Searching Authority, issued in PCT/JP2013/066685, dated Sep. 24, 2013.

* cited by examiner

Primary Examiner — Michael Szperka
(74) Attorney, Agent, or Firm — Birch, Stewart, Kolasch & Birch, LLP

(57) ABSTRACT

It is intended to provide an IgE peptide vaccine that can be used in the prevention or treatment of allergic diseases in animals other than mice, such as humans or dogs. The present invention provides a peptide consisting of (i) the amino acid sequence represented by SEQ ID NO: 28, or (ii) an amino acid sequence consisting of at least 10 consecutive amino acids in the amino acid sequence represented by SEQ ID NO: 28, wherein the peptide, when administered to an animal, is capable of specifically binding to a CH3 region in an IgE antibody of the animal and thereby blocking the binding of the IgE antibody to an IgE receptor.

6 Claims, 43 Drawing Sheets

Fig. 1-1

DOG

ESDPRGVSSYLSPPSPLDLYVHKAPKITCLVVDLATMEGMNLTWYRESKEPVNPGPLNKKDHFNGTIIVTSTLPVNTNDWIEGETYYCRVTHPHLPKDIVRSIAKAP (SEQ ID NO:1)

ESDPRGVSSYLSPPS (CH3-1) (SEQ ID NO:2)
GVSSYLSPPSPLDLY (CH3-14) (SEQ ID NO:3)
LSPPSPLDLYVHKAP (CH3-8) (SEQ ID NO:4)
PLDLYVHKAPKITCL (CH3-2) (SEQ ID NO:5)
VHKAPKITGLVVDLA (CH3-15) (SEQ ID NO:6)
KITCLVVDLATMEGM (CH3-9) (SEQ ID NO:7)
VVDLATMEGMNLTWY (CH3-3) (SEQ ID NO:8)
TMEGMNLTWYRESKE (CH3-16) (SEQ ID NO:9)
NLTWYRESKEPVNPG (CH3-10) (SEQ ID NO:10)
RESKEPVNPGPLNKK (CH3-4) (SEQ ID NO:11)
PVNPGPLNKKDHFNG (CH3-17) (SEQ ID NO:12)
PLNKKDHFNGTIIVT (CH3-11) (SEQ ID NO:13)
DHFNGTIIVTSTLPV (CH3-5) (SEQ ID NO:14)
IIVTSTLPVNTNDWI (CH3-18) (SEQ ID NO:15)
STLPVNTNDWIEGET (CH3-12) (SEQ ID NO:16)
NTNDWIEGETYYCRV (CH3-6) (SEQ ID NO:17)
IEGETYYCRVTHPHL (CH3-19) (SEQ ID NO:18)
YYCRVTHPHLPKDIV (CH3-13) (SEQ ID NO:19)
THPHLPKDIVRSIAKAP (CH3-7) (SEQ ID NO:20)

mouse

HEPRGVITYLIPPSPLDLYQNGAPKLTCLVDLESEKNVNVTWNQEKKTSVSASQWYTKHHNNATTSITSILPVVAKDWIEGYGYQCIVDHPDFKPIVRSITKTPQ (SEQ ID NO:21)

NVTWNQEKKTSVSAS (mouse CH3-10) (SEQ ID NO:22)
QEKKTSVSASQWYIK (mouse CH3-4) (SEQ ID NO:23)
SVSASQWYTKHHNNA (mouse CH3-17) (SEQ ID NO:24)
QWYTKHHNNATTSIT (mouse CH3-11) (SEQ ID NO:25)
HHNNATTSITSILPV (mouse CH3-5) (SEQ ID NO:26)

Fig. 1-2

```
Text1

[ GENETYX : Amino Acid Sequence Homology Data ]

Date : 2008.09.04

1st Amino Acid Sequence
   File Name         : canine IgE CH3 amino.gpt
   Sequence Size     : 107

2nd Amino Acid Sequence
   File Name         : mouse IgE CH3 amino
   Sequence Size     : 107

Unit Size to Compare = 2
   Pick up Location No. = 1

[ 58 / 105 aa]      INT/OPT.Score : <    134/   325 >

1' ESDPRGVSSY LSPPSPLDLY VHKAPKITCL VVDLATMEGM NLTWYRESKE PVNPGPLNKK
        .****  .*  * ******** . *** *** ****.. ... *. **  . * .*.   .*    .*
     1" HEPRGVITY  LIPPSPLDLY QNGAPKLTCL VVDLESEKNV NVTWNQEKKT SVSASQWYTK

61' DHFNGTITVT STLPVNTNDW IEGETYYCRV THPHLPKDIV RSIAKAP
        .* *.*...* *.***  ..** *** .*  *  .**..** ** ***.*.*
    60" HHNNATTSIT SILPVVAKDW IEGYGYQCIV DHPDFPKPIV RSITKTPQ
```

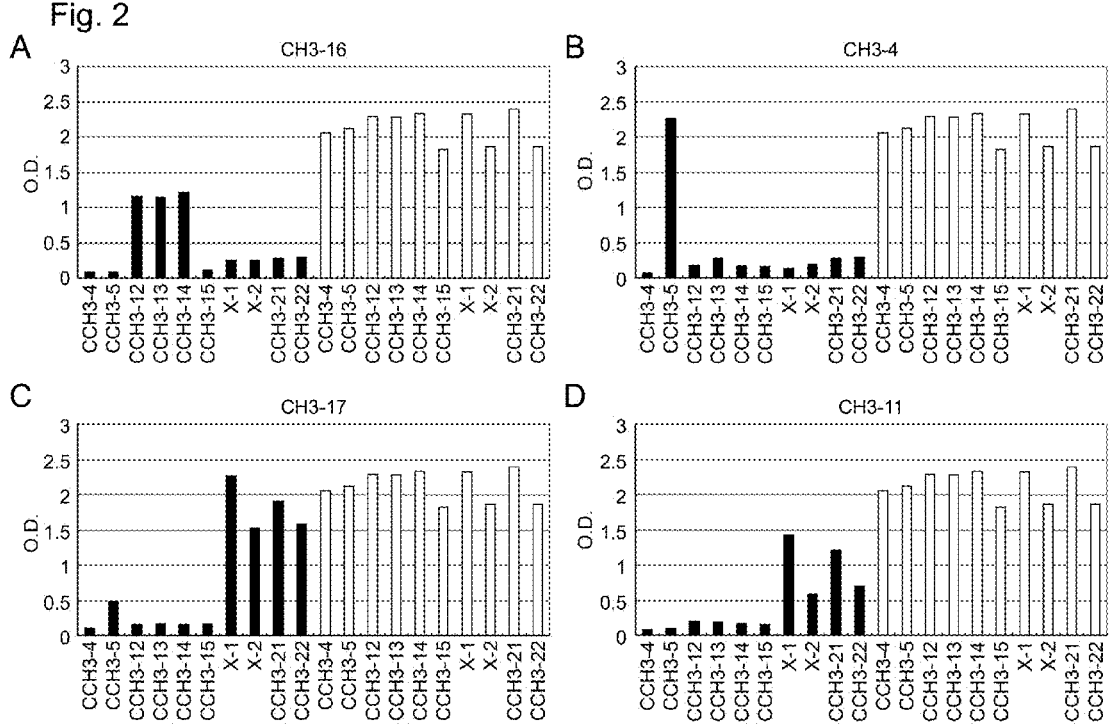

Fig. 6-1

|  | Anti-dog IgG | Anti-dog IgG1 | Anti-dog IgG2 |
|---|---|---|---|
| Peptide | ○ | ○ | ○ |
| Dog IgE | × | ○ | × |
| Mouse IgE | × | × | × |
| Human IgE | ○ | ○ | ○ |

A

B

Fig. 6-3
A
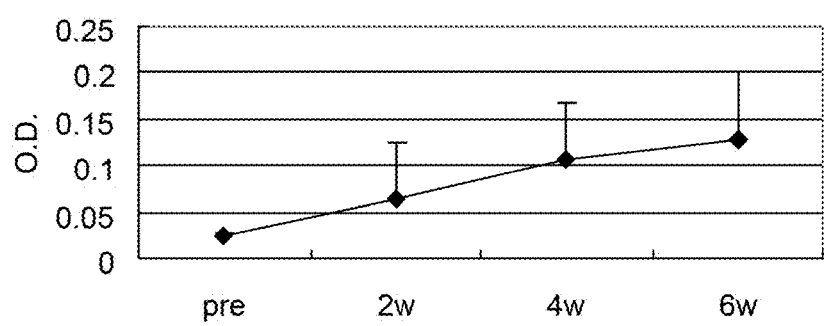
B
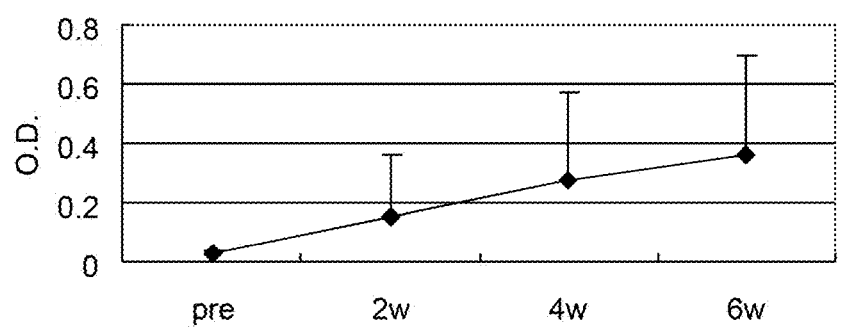
C
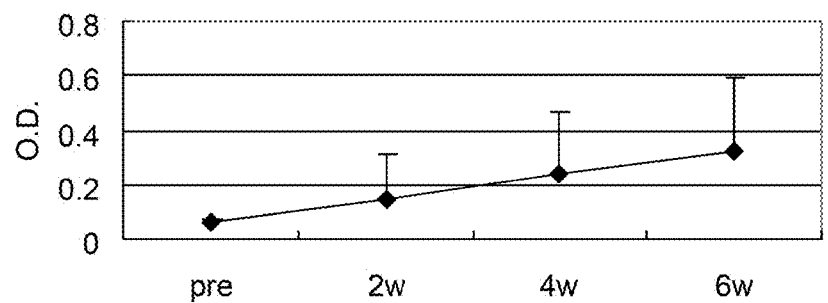

A

B

Fig. 6-6
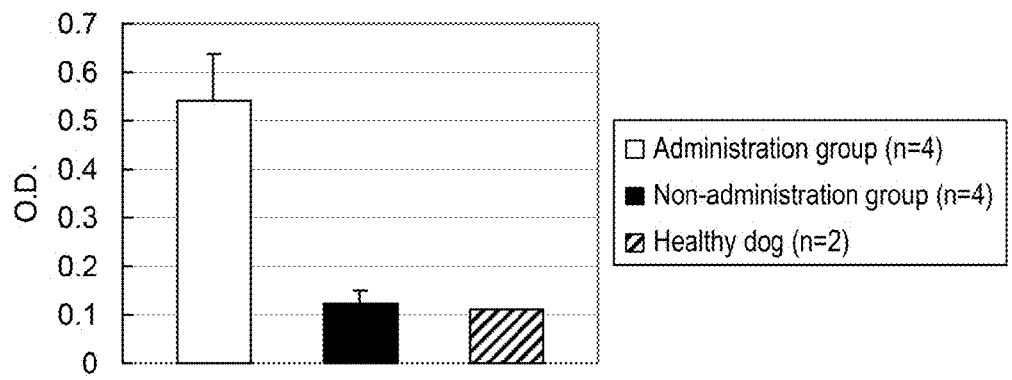
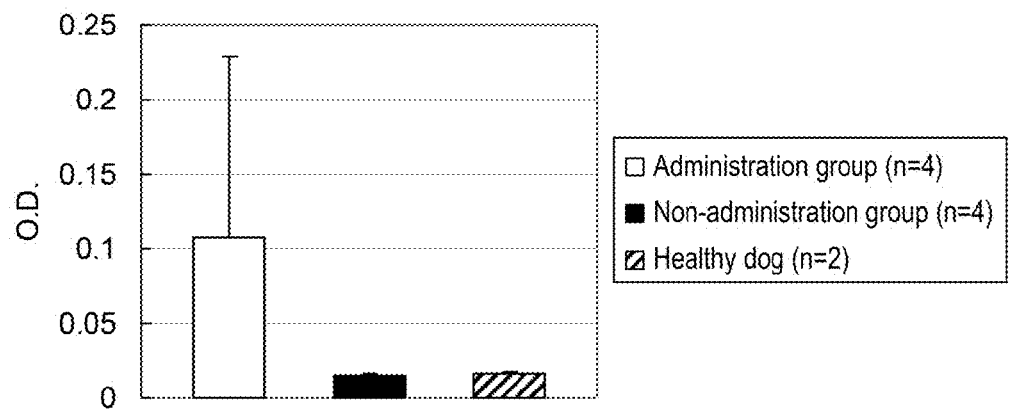
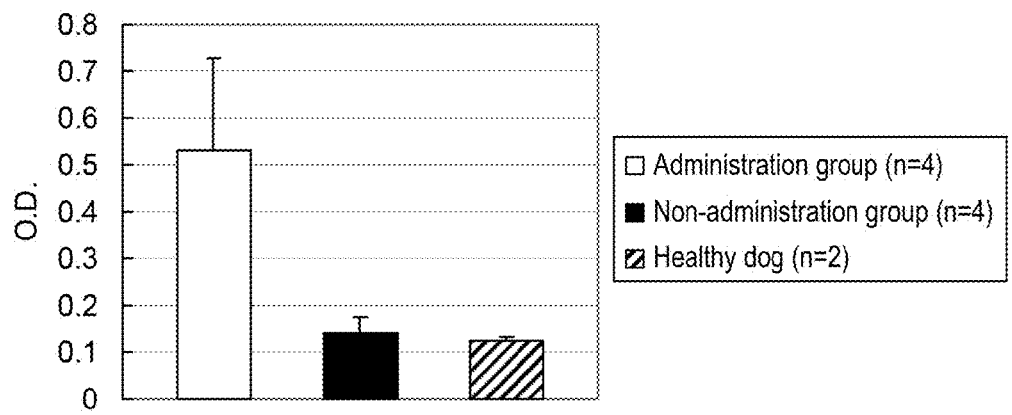

Serum 1: pooled serum of non-administration group
Serum 2: pooled serum of administration group
Serum 3: pooled serum of non-administration group
Serum 4: pooled serum of healthy dog
Serum 1 to serum 4 are indicated by circled numbers 1 to 4, respectively, in the diagram.

Serum 1: pooled serum of non-administration group (adjusted with saline so as to have Der f 2-specific IgE concentration equal to that of serum 2)
Serum 2: pooled serum of administration group
Serum 3: pooled serum of non-administration group
Serum 4: pooled serum of healthy dog
Serum 1 to serum 4 are indicated by circled numbers 1 to 4, respectively, in the diagram.

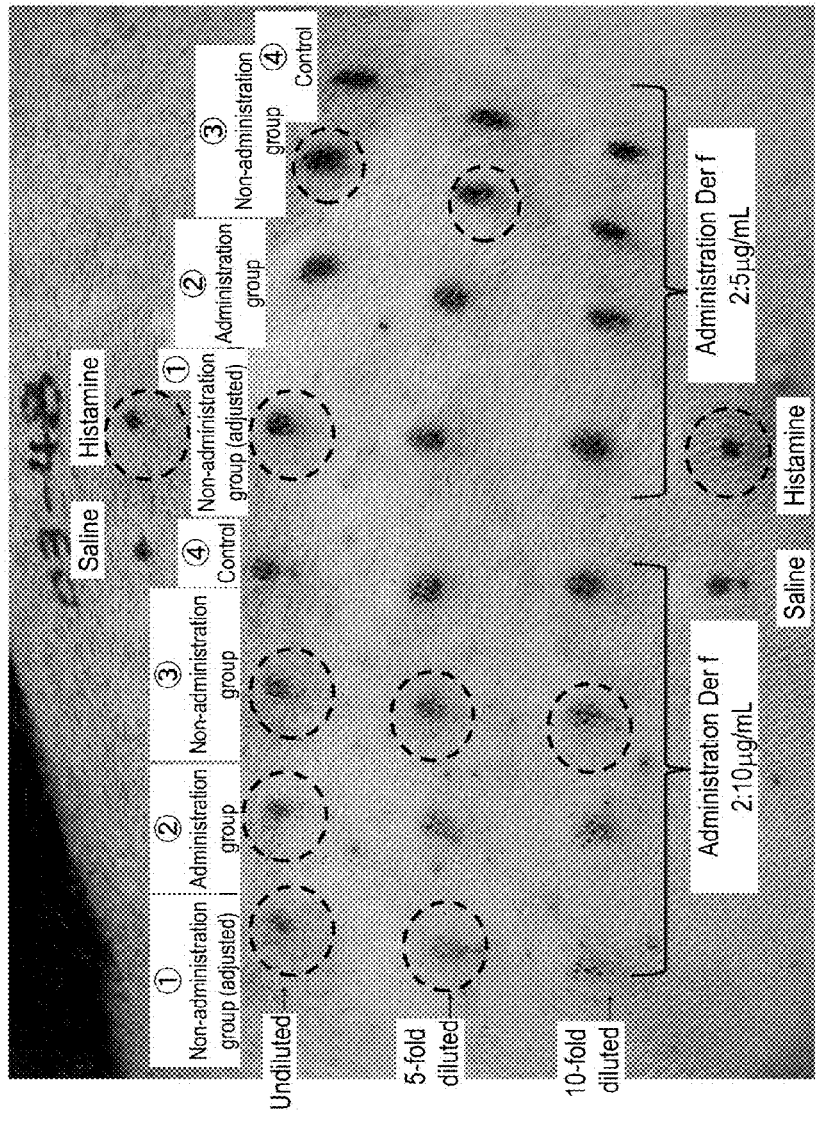

Fig. 9

Flare was circled
Serum 1: pooled serum of non-administration group (adjusted with saline so as to have Der f 2-specific IgE concentration equal to that of serum 2)
Serum 2: pooled serum of administration group
Serum 3: pooled serum of non-administration group
Serum 4: pooled serum of healthy dog
Serum 1 to serum 4 are indicated by circled numbers 1 to 4, respectively, in the diagram.

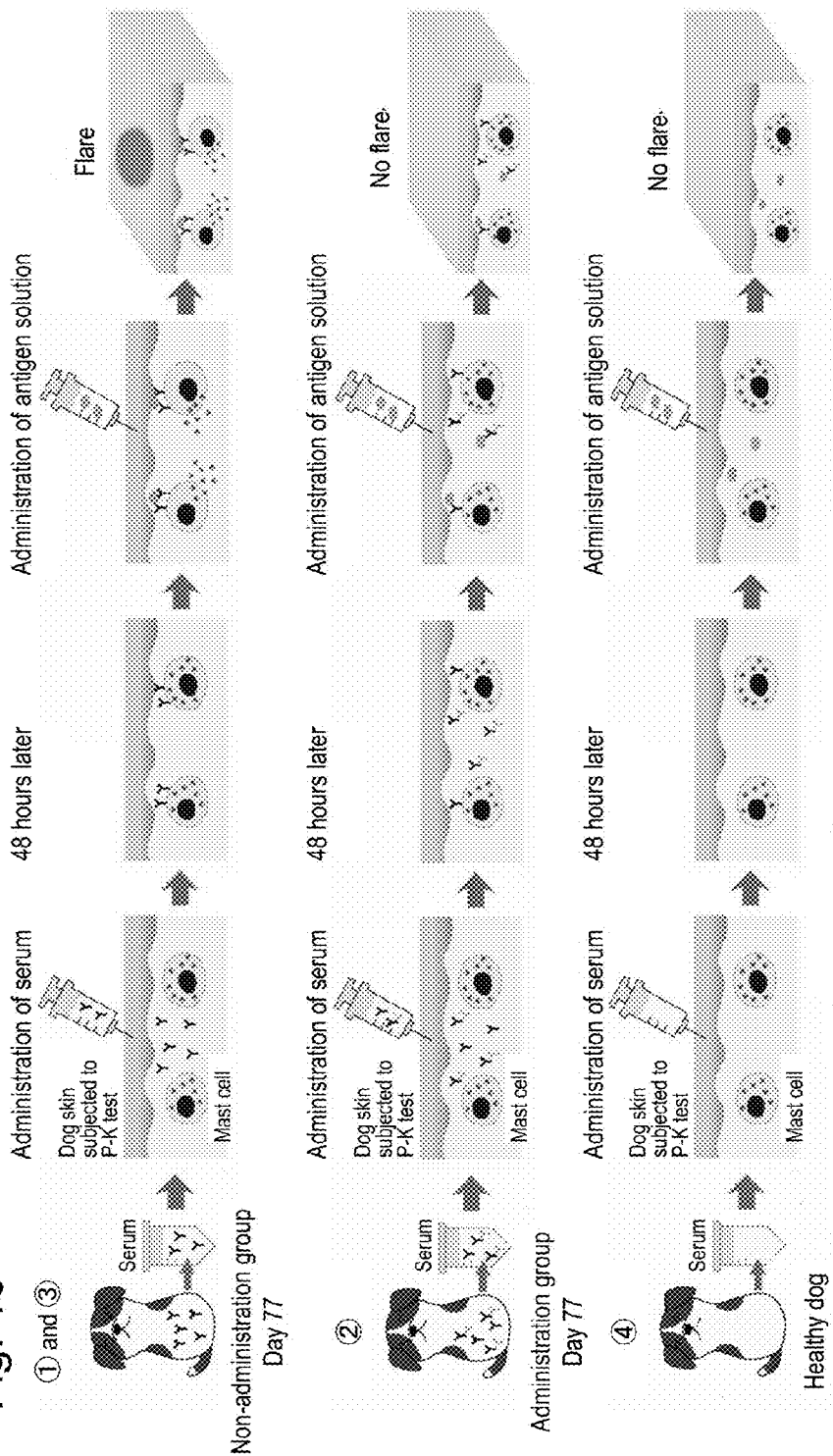

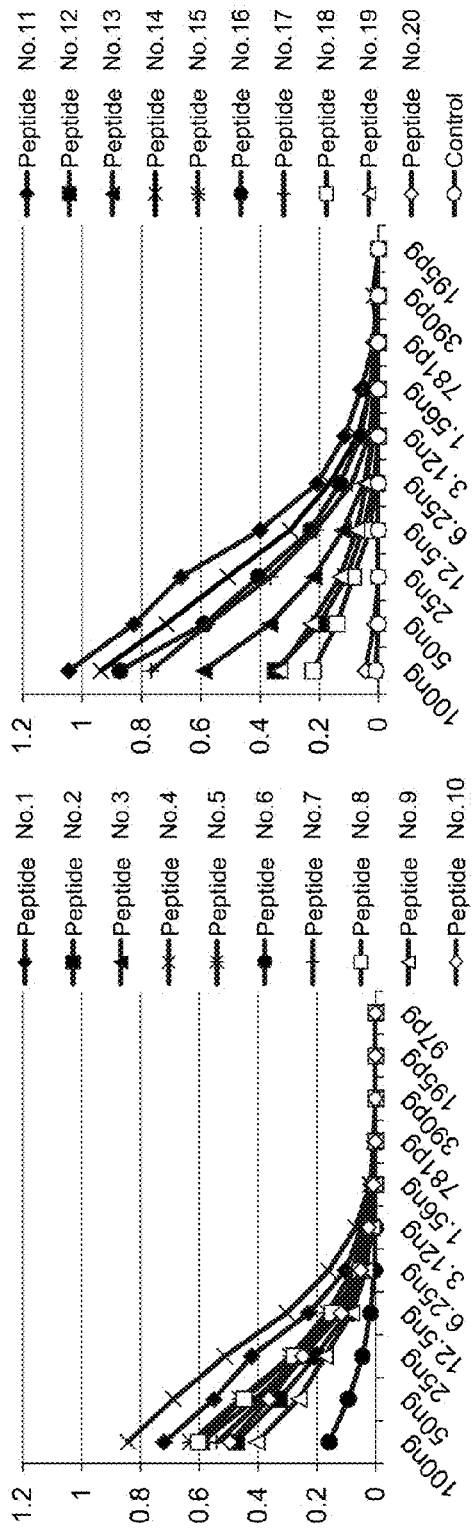

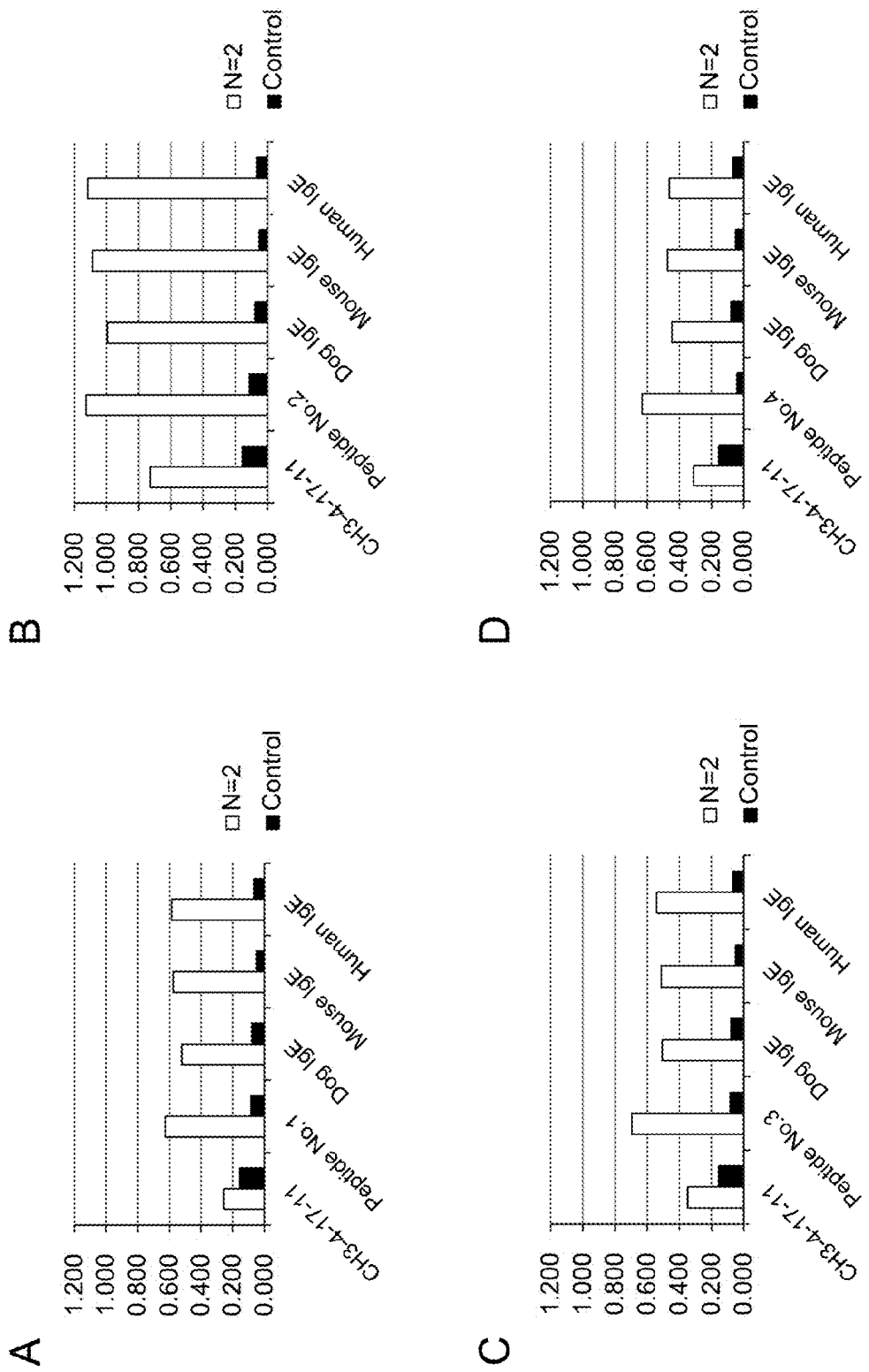

Fig. 14
A
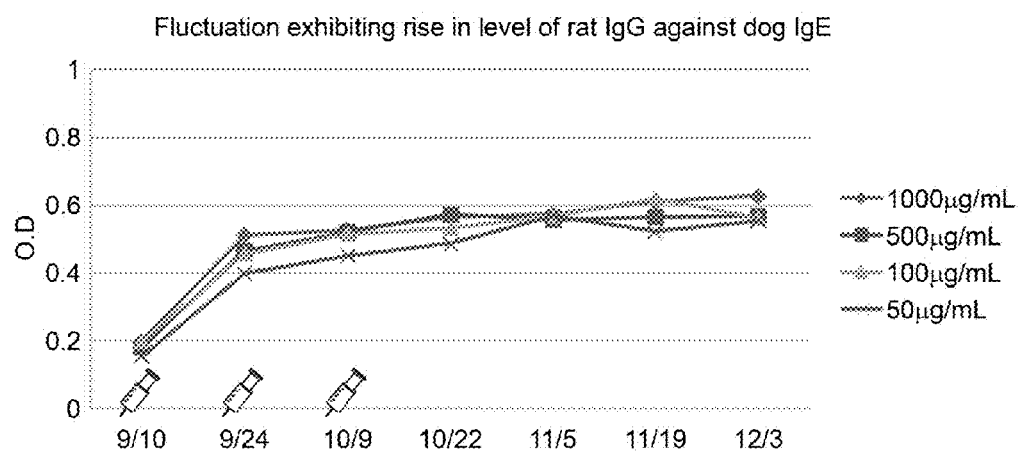
B
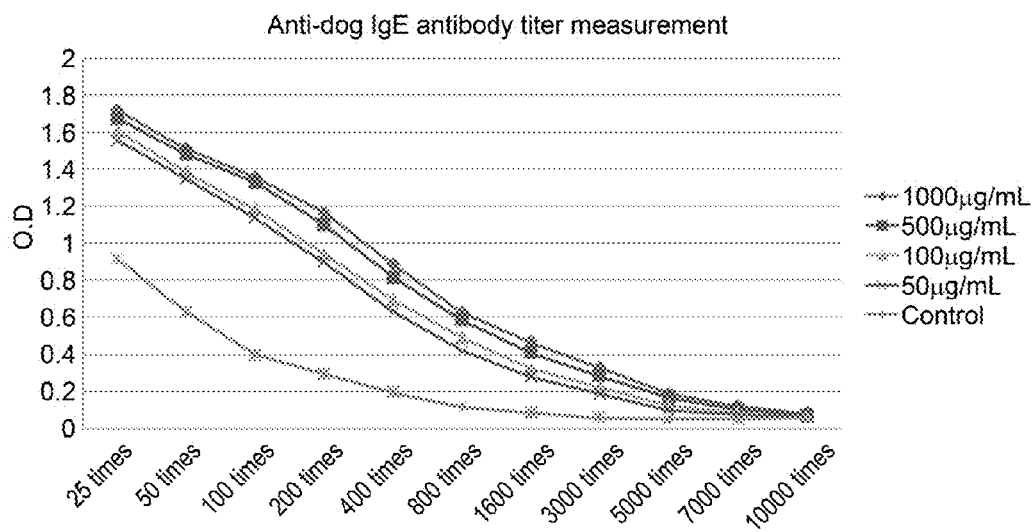

Grouping  Rat: Wister ♀ 7W

Prevention experiment groups (n=12)

1 Group: IgE peptide (50μg/mL) (n=4) intravenous administration
   ⇒ Sensitization (*D. farinae* +Alum) ⇒ Boosting 2 Group: IgE petide (50μg/mL) (n= 4) subcutaneous administration
   ⇒ Sensitization (*D. farinae* +Alum) ⇒ Boosting 3 Group (control): No administration (n=4) ⇒ Sensitization (*Der f 2* +Alum)
   ⇒ Boosting Fig. 17
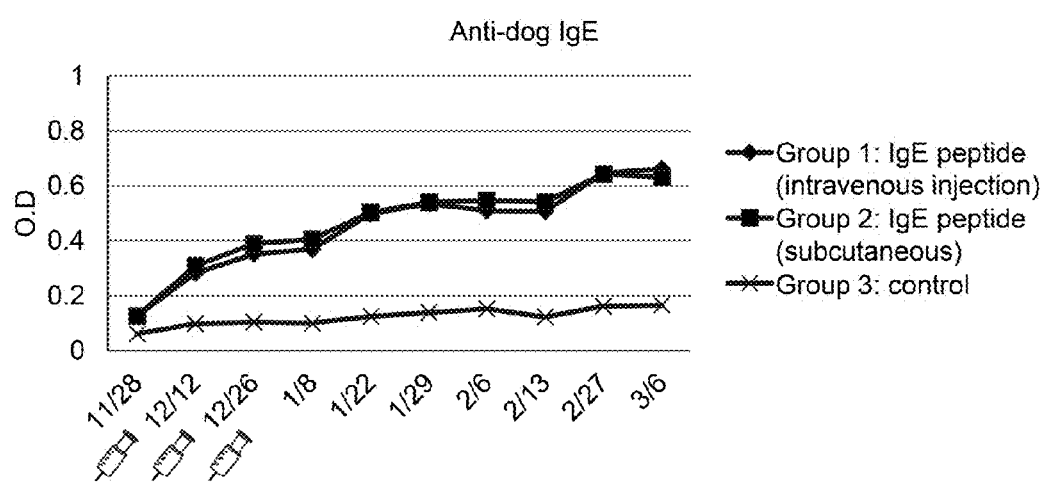
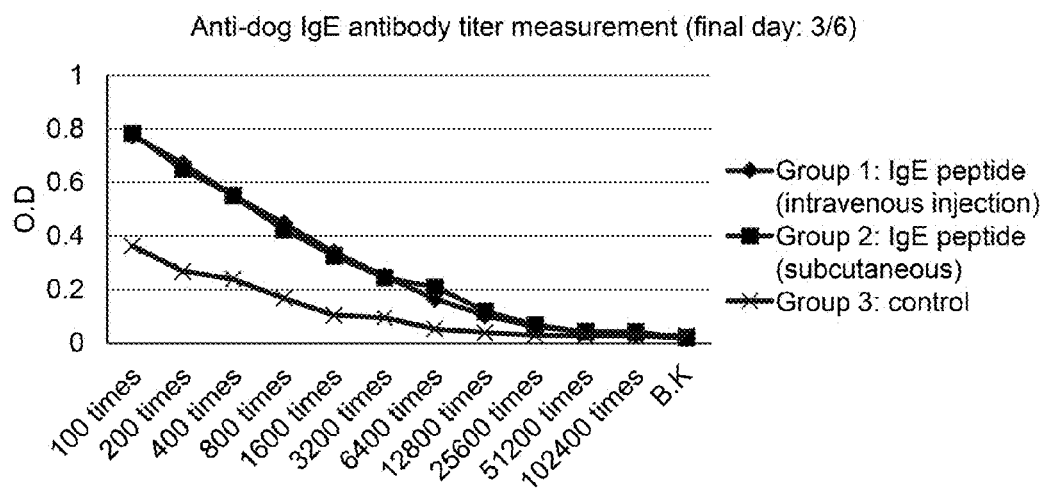

Fig. 24
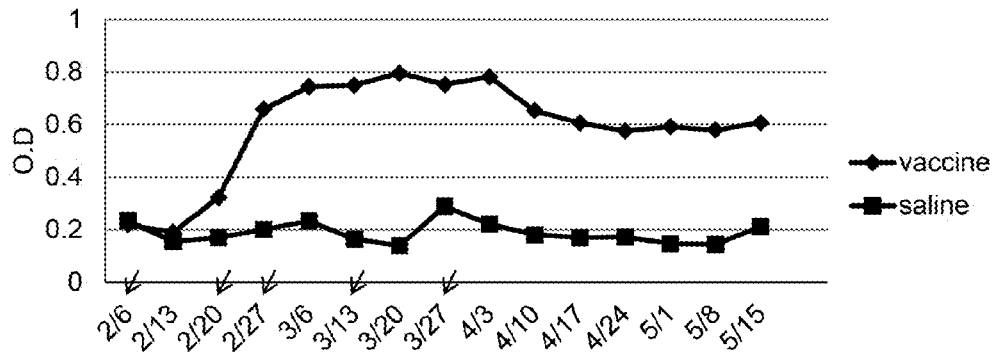
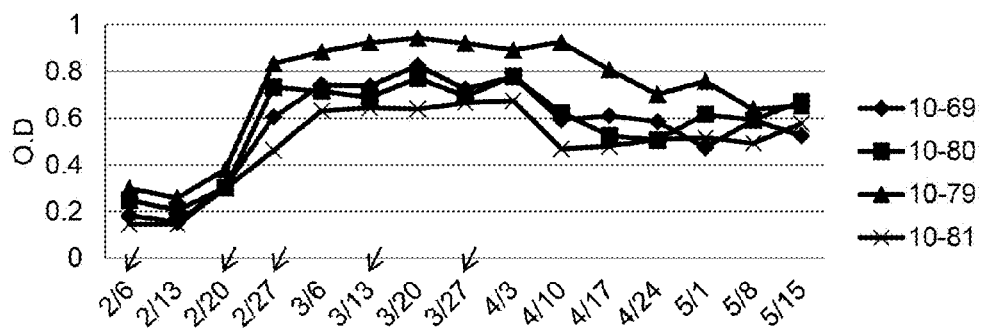
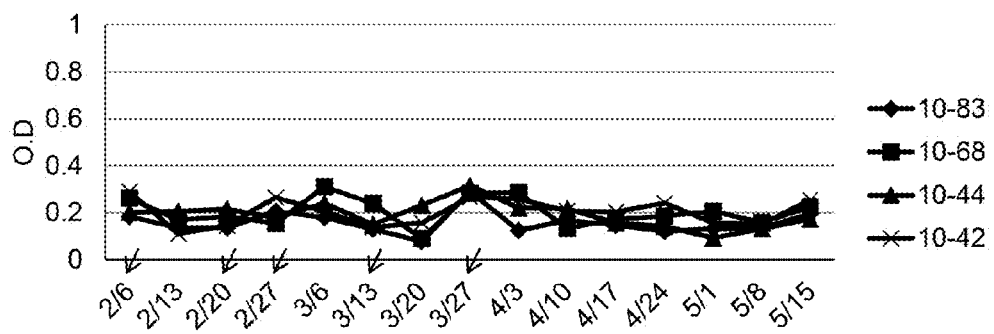

Fig. 26
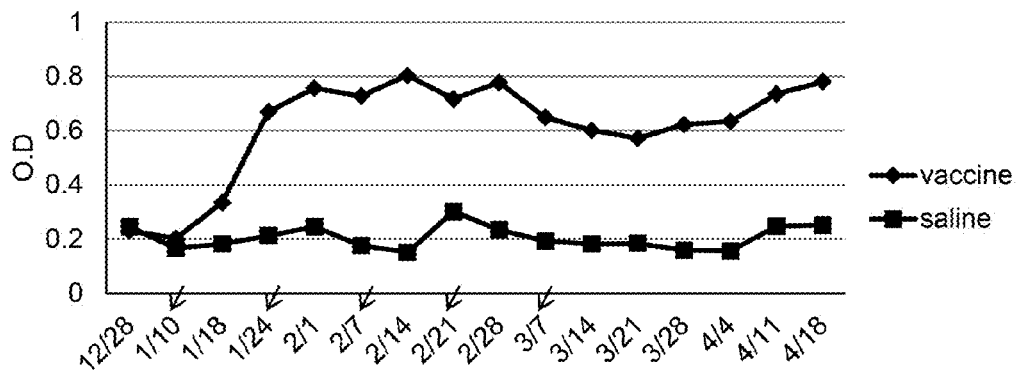
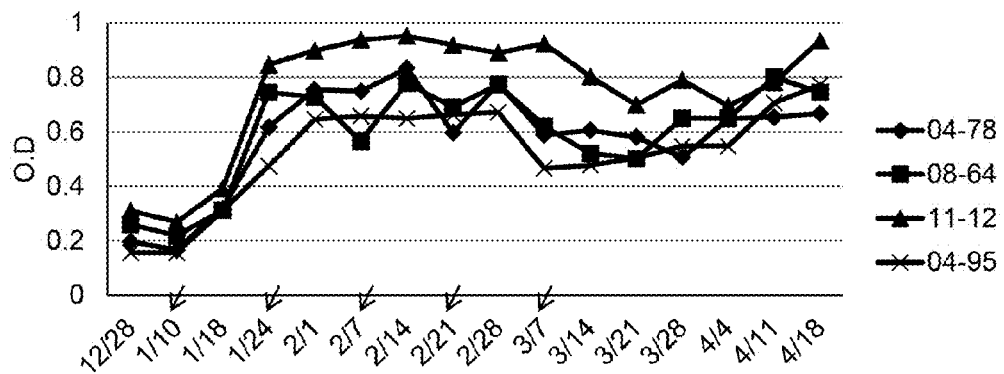
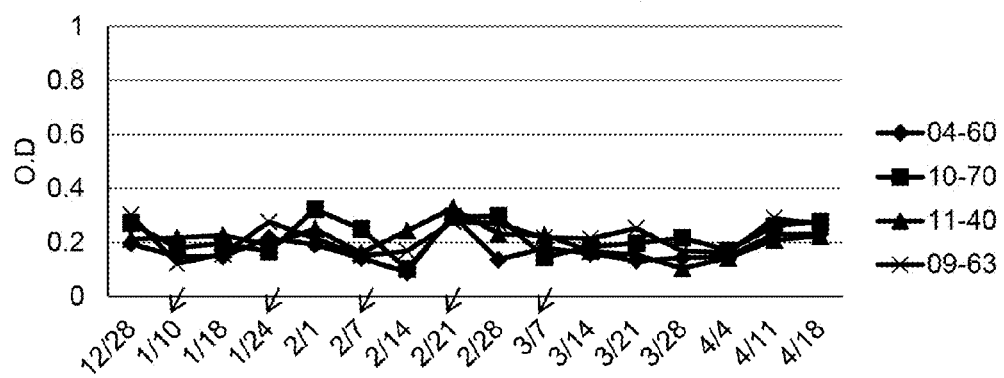

Fig. 27
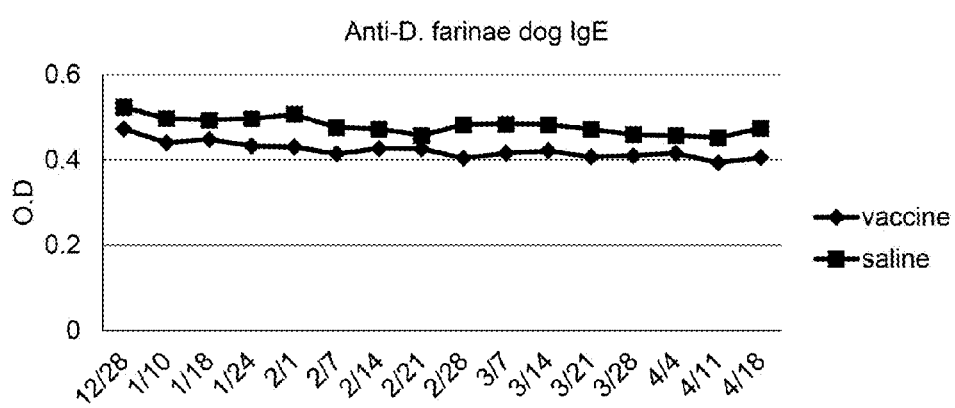
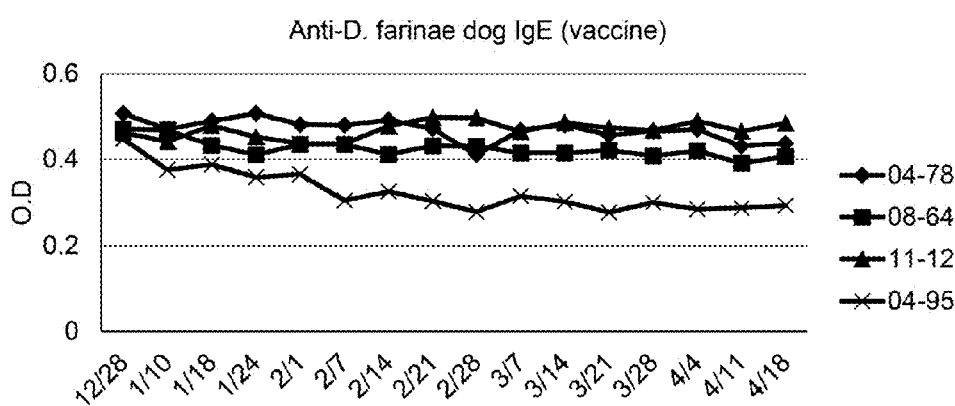
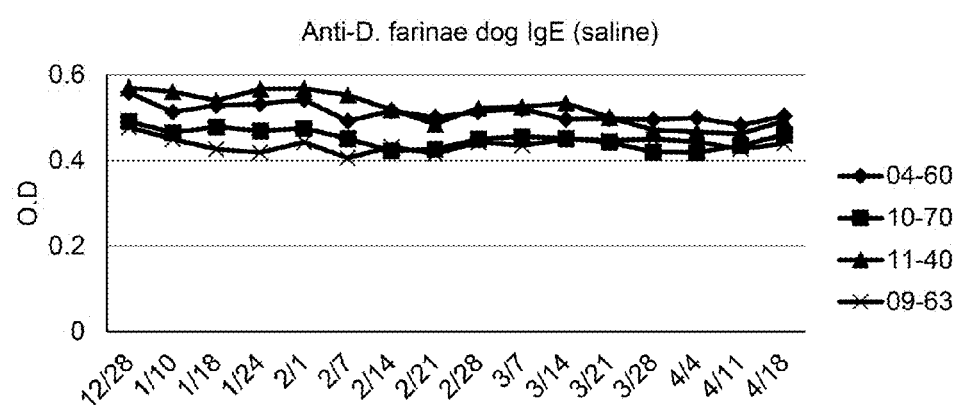

IGE PEPTIDE VACCINE

TECHNICAL FIELD

The present invention relates to a partial peptide of mouse IgE that can be used in the prevention or treatment of allergic diseases, and an IgE peptide vaccine comprising the same.

BACKGROUND ART

Peptide vaccine therapy involves administering an antigen (e.g., tumor antigen) or its epitope portion together with an adjuvant, thereby inducing both cell-mediated immunity and humoral immunity against the antigen (e.g., tumor antigen), and is currently under clinical application.

IgE is involved in allergy, particularly, type I allergy. In recent years, an increasing number of dogs raised as pet animals suffer from allergic diseases, as in humans.

A possible method for treating type I allergy is the utilization of a compound that binds to IgE in serum and thereby inhibits the binding of IgE to mast cells. It has been suggested that an antibody binding to the Fc region of IgE can be used for such a purpose (see Patent Literature 1).

It has been reported that: the peptide vaccine therapy is applied to the treatment of allergy; and an antigenic peptide induced from an IgE CH3 region is used as a peptide vaccine (see Patent Literature 2). For the treatment of allergy in dogs, however, an antigenic peptide of IgE derived from the same species has been used as a vaccine in order to induce an antibody against dog IgE.

CITATION LIST

Patent Literature

Patent Literature 1: JP Patent Publication (Kokai) No. 2006-151880 A (2006)
Patent Literature 2: JP Patent Publication (Kokai) No. 2005-102701 A (2005)

SUMMARY OF INVENTION

Technical Problem

An object of the present invention is to provide an IgE peptide vaccine that can be used in the prevention or treatment of allergic diseases in animals other than mice, such as humans or dogs.

Solution to Problem

The present inventors have conducted studies on a method for treating allergy in dogs. The present inventor et al. have first prepared anti-dog IgE rat monoclonal antibodies and found the presence of monoclonal antibodies recognizing dog IgE, mouse IgE, and cat IgE. This suggests that an antibody recognizing a particular epitope in, for example, mouse IgE, is capable of recognizing even IgE of other animal species. On the basis of this finding, the present inventor has considered the possibility of using a partial peptide of mouse IgE in the induction of antibodies against IgE of other animal species, i.e., using a partial peptide of mouse IgE as a peptide vaccine for allergy treatment intended to be administered to other animal species, and conducted diligent studies.

As a result, the present inventors have found that: when a partial peptide, which does not necessarily have high sequence identity to dog IgE, is administered to a dog, an antibody against the partial peptide is induced in vivo in the dog; and the antibody recognizes not only the peptide but IgE and further binds to the Fc region of IgE of the dog's own and thereby blocks the binding of this IgE to mast cells.

The present inventors have consequently found that the partial peptide of mouse IgE can be used as a vaccine for the treatment of IgE-mediated allergy, and completed the present invention.

The peptide can be used as a peptide vaccine not only against dogs but against animals (including humans) except for mice or rodents closely related to mice.

The peptide can be used as a vaccine through the subcutaneous administration of this peptide alone without the use of an adjuvant.

Specifically, the present invention is as follows:

[1] A peptide consisting of
(i) the amino acid sequence represented by SEQ ID NO: 28, or
(ii) an amino acid sequence consisting of at least 10 consecutive amino acids in the amino acid sequence represented by SEQ ID NO: 28, wherein
the peptide, when administered to an animal, is capable of specifically binding to a CH3 region of an IgE antibody of the animal and thereby blocking the binding of the IgE antibody to an IgE receptor.

[2] The peptide according to [1], the peptide consisting of
(i) the amino acid sequence represented by SEQ ID NO: 27, or
(ii) an amino acid sequence consisting of at least 10 consecutive amino acids in the amino acid sequence represented by SEQ ID NO: 27, wherein
the peptide, when administered to an animal, is capable of specifically binding to a CH3 region in an IgE antibody of the animal and thereby blocking the binding of the IgE antibody to an IgE receptor.

[3] The peptide according to [1], wherein the peptide consists of an amino acid sequence selected from the group consisting of SEQ ID NOs: 22, 23, 24, 25, and 26.

[4] The peptide according to [2], wherein the peptide consists of an amino acid sequence selected from SEQ ID NOs: 29 to 92.

[5] The peptide according to [4], wherein the peptide consists of an amino acid sequence selected from the group consisting of SEQ ID NOs: 29, 31, 34, 38, 43, 49, 56, 64, 72, 82, 30, 33, 37, 42, 48, 55, 63, 71, 81, and 92.

[6] The peptide according to [4], wherein the peptide consists of the amino acid sequence represented by SEQ ID NO: 45.

[7] A peptide consisting of an amino acid sequence derived from the amino acid sequence of a peptide according to any of [1] to [6] by the deletion, substitution, or addition of 1 to 3 amino acids, wherein the peptide, when administered to an animal, is capable of specifically binding to a CH3 region of an IgE antibody of the animal and thereby blocking the binding of the IgE antibody to an IgE receptor.

[8] A vaccine or therapeutic agent for an IgE-mediated disease, comprising a peptide according to any of [1] to [7].

[9] The vaccine or therapeutic agent according to [8], wherein the IgE-mediated disease is selected from the group consisting of atopic dermatitis, pollinosis, food allergy, allergic rhinitis, bronchial asthma, allergic conjunctivitis, mite allergy, hives, anaphylactic shock, and PIE (pulmonary infiltration with eosinophilia) syndrome.

[10] A method for preventing or treating an IgE-mediated disease, comprising administering a vaccine or therapeutic agent for an IgE-mediated disease, comprising a peptide according to any of [1] to [7], to a nonhuman animal.

[11] The method for preventing or treating an IgE-mediated disease according to [10], wherein the IgE-mediated disease is selected from the group consisting of atopic dermatitis, pollinosis, food allergy, allergic rhinitis, bronchial asthma, allergic conjunctivitis, mite allergy, hives, anaphylactic shock, and PIE (pulmonary infiltration with eosinophilia) syndrome.

The present specification encompasses the contents described in the specification and/or drawings of Japanese Patent Application No. 2012-136944 on which the priority of the present application is based.

Advantageous Effects of Invention

The peptide of the present invention can induce the formation of an anti-IgE antibody (IgG) in mammals other than mice, such as dogs or humans. The anti-IgE antibody can bind to IgE of the animal species with the induced antibody and thereby block the binding of this IgE to an IgE receptor on mast cells or basophils. The partial peptide of the mouse IgE CH3 region of the present invention can therefore be used as an IgE peptide vaccine for the prevention or treatment of IgE-mediated diseases (e.g., allergic diseases) which give rise to IgG antibodies against IgE.

BRIEF DESCRIPTION OF DRAWINGS

FIG. 1-1 is a diagram showing the map of synthetic peptides of the dog IgE CH3 region.

FIG. 1-2 is a diagram showing the alignment of dog IgE CH3 region and mouse IgE CH3 region amino acid sequences.

FIG. 2 is a diagram showing results of epitope analysis.

FIG. 3-1 is a diagram showing results of measuring peptide-specific IgG concentrations in serum.

FIG. 3-2 is a diagram showing results of measuring IgE-specific IgG concentrations in serum.

FIG. 6-1 is a diagram showing the presence or absence of the nonspecific reaction between an immobilized antigen and a detection antigen.

FIG. 6-2 is a diagram showing results of analyzing the reactivity between each antigen (IgE peptide and human IgE) and an anti-dog IgG antibody.

FIG. 6-3 is a diagram showing results of analyzing the reactivity between each antigen (IgE peptide, human IgE, and dog IgE) and an anti-dog IgG1 antibody.

FIG. 6-4 is a diagram showing results of analyzing the reactivity between each antigen (IgE peptide and human IgE) and an anti-dog IgG2 antibody.

FIG. 6-5 is a diagram showing results of analyzing the reactivity of Der f 2-specific IgE after administration of a peptide and subsequent immunization (artificial sensitization) with Der f 2 together with an alum adjuvant.

FIG. 6-6 is a diagram showing levels of human IgE-specific dog IgG, IgG1, and IgG2 in the serum of a dog immunized (artificially sensitized) with Der f 2 together with an alum adjuvant.

FIG. 9 is a diagram showing exemplary results of Prausnitz-Kustner (P-K) test. In the drawing, circled numbers 1 to 4 denote serum 1 to serum 4, respectively.

FIG. 10 is a diagram showing a reason why serum 1 and serum 2 having the same concentrations of Der f 2-specific IgE differed in score in the Prausnitz-Kustner (P-K) test.

FIG. 11-1 is a diagram showing the reactivity between the serum of a peptide-immunized (artificially sensitized) rabbit and dog IgE.

FIG. 11-2 is a diagram showing the reactivity between the serum of a peptide-immunized (artificially sensitized) rabbit and dog IgG.

FIG. 11-3 is a diagram showing the reactivity between the serum of a peptide-immunized (artificially sensitized) rabbit and mouse IgE.

FIG. 11-4 is a diagram showing the reactivity between the serum of a peptide-immunized (artificially sensitized) rabbit and human IgE.

FIG. 11-5 is a diagram showing the reactivity between the serum of a peptide-immunized (artificially sensitized) rabbit and cat recombinant CH3.

FIG. 12-1 is a diagram showing the vaccine effects of 20 types of peptides on rats.

FIG. 12-2 is a diagram showing the vaccine effects of peptide Nos. 1 to 4 among 20 types of peptides on rats (assayed using 100-fold diluted serum).

FIG. 12-3 is a diagram showing the vaccine effects of peptide Nos. 5 to 8 among 20 types of peptides on rats (assayed using 100-fold diluted serum).

FIG. 12-4 is a diagram showing the vaccine effects of peptide Nos. 9 to 12 among 20 types of peptides on rats (assayed using 100-fold diluted serum).

FIG. 12-5 is a diagram showing the vaccine effects of peptide Nos. 13 to 16 among 20 types of peptides on rats (assayed using 100-fold diluted serum).

FIG. 12-6 is a diagram showing the vaccine effects of peptide Nos. 17 to 20 among 20 types of peptides on rats (assayed using 100-fold diluted serum).

FIG. 14 is a diagram showing a rise in anti-IgE antibody titer when a peptide is intravenously administered to rats.

FIG. 17 is a diagram showing fluctuations exhibiting a rise in anti-IgE antibody titer and final antibody titers when a peptide is subcutaneously administered to rats.

FIG. 24 is a diagram showing a rise in anti-IgE antibody titer when a peptide was subcutaneously administered to dogs.

FIG. 26 is a diagram showing a rise in anti-IgE antibody titer when a peptide was subcutaneously administered to dogs artificially sensitized with *Dermatophagoides farinae*.

FIG. 27 is a diagram showing results of assaying *Dermatophagoides farinae* antigen-specific IgE when a peptide was subcutaneously administered to dogs artificially sensitized with *Dermatophagoides farinae*.

DESCRIPTION OF EMBODIMENTS

Figures 1, 3:
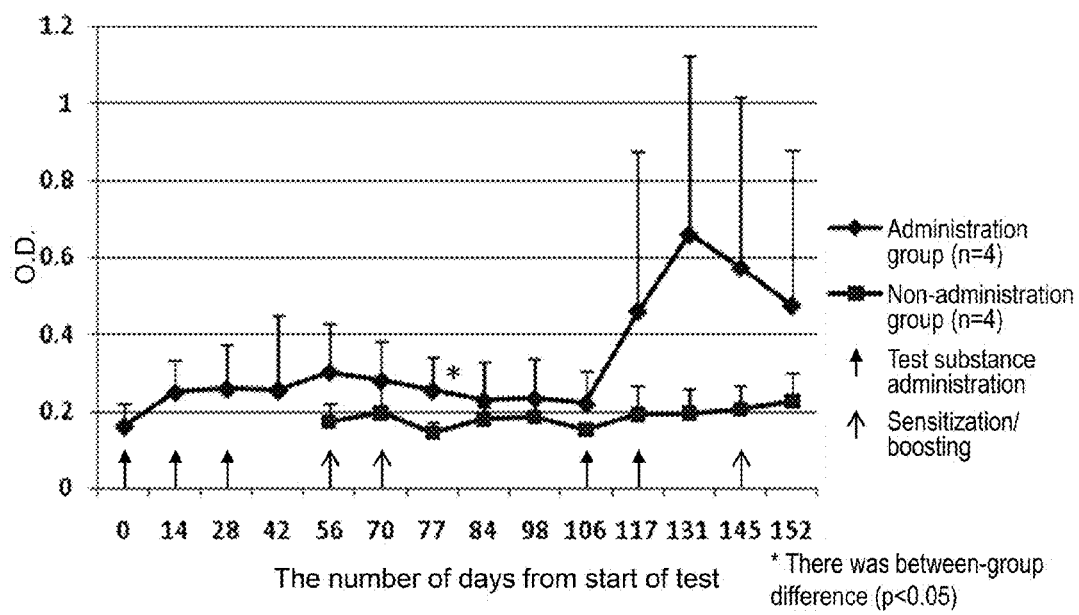

Hereinafter, the present invention will be described in detail.

The peptide for use in a peptide vaccine for the treatment of allergic diseases according to the present invention is a partial peptide of mouse IgE. Specifically, the peptide of the present invention is a peptide consisting of the amino acid sequence represented by NVTWNQEKKTSVSASQWYTKHHNNATTSITSILPV (SEQ ID NO: 28) in the CH3 (Cε3) region of a mouse IgE peptide, or a partial peptide of the peptide, the partial peptide consisting of an amino acid sequence of at least 6, 7, 8, or 9, preferably at least 10, 11, 12, 13, 14, 15, 16, 17, 18, 19, 20, 21, 22, 23, or 24, more preferably at least 25 consecutive amino acids. Examples of such partial peptides include partial peptides consisting of the amino acid sequences represented by SEQ ID NOs: 22 (NVTWNQEKKTSVSAS), 23 (QEKKTSVSASQWYTK), 24 (SVSASQWYTKHHNNA), 25 (QWYTKHHNNATTSIT), 26 (HHNNATTSITSILPV), and 27. Among them, a peptide consisting of the amino acid sequence represented by QEKKTSVSASQWYTKHHNNATTSIT (SEQ ID NO: 27), or a partial peptide of the peptide, the partial peptide consisting of an amino acid sequence of at least 6, preferably at least 10 consecutive amino acids, is preferred. Examples of such partial peptides include partial peptides consisting of the amino acid sequences represented by SEQ ID NOs: 23, 24, and 25. In addition, a partial peptide of the peptide consisting of the amino acid sequence represented by QEKKTSVSASQWYTKHHNNATTSIT (SEQ ID NO: 27), the partial peptide consisting of an amino acid sequence of 15 to 24 consecutive amino acids, can also be preferably used. Examples of the partial peptide of the peptide consisting of the amino acid sequence represented by QEKKTSVSASQWYTKHHNNATTSIT (SEQ ID NO: 27), the partial peptide consisting of an amino acid sequence of 15 to 24 consecutive amino acids, include peptides consisting of the following amino acid sequences:

QEKKTSVSASQWYTKHHNNATTSI, (SEQ ID NO: 29)

EKKTSVSASQWYTKHHNNATTSIT, (SEQ ID NO: 30)

QEKKTSVSASQWYTKHHNNATTS, (SEQ ID NO: 31)

EKKTSVSASQWYTKHHNNATTSI, (SEQ ID NO: 32)

KKTSVSASQWYTKHHNNATTSIT, (SEQ ID NO: 33)

QEKKTSVSASQWYTKHHNNATT, (SEQ ID NO: 34)

EKKTSVSASQWYTKHHNNATTS, (SEQ ID NO: 35)

KKTSVSASQWYTKHHNNATTSI, (SEQ ID NO: 36)

KTSVSASQWYTKHHNNATTSIT, (SEQ ID NO: 37)

QEKKTSVSASQWYTKHHNNAT, (SEQ ID NO: 38)

EKKTSVSASQWYTKHHNNATT, (SEQ ID NO: 39)

KKTSVSASQWYTKHHNNATTS, (SEQ ID NO: 40)

KTSVSASQWYTKHHNNATTSI, (SEQ ID NO: 41)

TSVSASQWYTKHHNNATTSIT, (SEQ ID NO: 42)

QEKKTSVSASQWYTKHHNNA, (SEQ ID NO: 43)

EKKTSVSASQWYTKHHNNAT, (SEQ ID NO: 44)

KKTSVSASQWYTKHHNNATT, (SEQ ID NO: 45)

KTSVSASQWYTKHHNNATTS, (SEQ ID NO: 46)

TSVSASQWYTKHHNNATTSI, (SEQ ID NO: 47)

SVSASQWYTKHHNNATTSIT, (SEQ ID NO: 48)

QEKKTSVSASQWYTKHHNN, (SEQ ID NO: 49)

EKKTSVSASQWYTKHHNNA, (SEQ ID NO: 50)

KKTSVSASQWYTKHHNNAT, (SEQ ID NO: 51)

KTSVSASQWYTKHHNNATT, (SEQ ID NO: 52)

TSVSASQWYTKHHNNATTS, (SEQ ID NO: 53)

SVSASQWYTKHHNNATTSI, (SEQ ID NO: 54)

VSASQWYTKHHNNATTSIT, (SEQ ID NO: 55)

QEKKTSVSASQWYTKHHN, (SEQ ID NO: 56)

EKKTSVSASQWYTKHHNN, (SEQ ID NO: 57)

KKTSVSASQWYTKHHNNA, (SEQ ID NO: 58)

KTSVSASQWYTKHHNNAT, (SEQ ID NO: 59)

TSVSASQWYTKHHNNATT, (SEQ ID NO: 60)

SVSASQWYTKHHNNATTS, (SEQ ID NO: 61)

VSASQWYTKHHNNATTSI, (SEQ ID NO: 62)

SASQWYTKHHNNATTSIT, (SEQ ID NO: 63)

QEKKTSVSASQWYTKHH, (SEQ ID NO: 64)

EKKTSVSASQWYTKHHN, (SEQ ID NO: 65)

KKTSVSASQWYTKHHNN, (SEQ ID NO: 66)

KTSVSASQWYTKHHNNA, (SEQ ID NO: 67)

SVSASQWYTKHHNNATT, (SEQ ID NO: 68)

VSASQWYTKHHNNATTS, (SEQ ID NO: 69)

SASQWYTKHHNNATTSI, (SEQ ID NO: 70)

ASQWYTKHHNNATTSIT, (SEQ ID NO: 71)

QEKKTSVSASQWYTKH, (SEQ ID NO: 72)

EKKTSVSASQWYTKHH, (SEQ ID NO: 73)

KKTSVSASQWYTKHHN, (SEQ ID NO: 74)

KTSVSASQWYTKHHNN, (SEQ ID NO: 75)

TSVSASQWYTKHHNNA, (SEQ ID NO: 76)

SVSASQWYTKHHNNAT, (SEQ ID NO: 77)

VSASQWYTKHHNNATT, (SEQ ID NO: 78)

SASQWYTKHHNNATTS, (SEQ ID NO: 79)

ASQWYTKHHNNATTSI, (SEQ ID NO: 80)

SQWYTKHHNNATTSIT, (SEQ ID NO: 81)

QEKKTSVSASQWYTK, (SEQ ID NO: 82)

EKKTSVSASQWYTKH, (SEQ ID NO: 83)

KKTSVSASQWYTKHH, (SEQ ID NO: 84)

KTSVSASQWYTKHHN, (SEQ ID NO: 85)

TSVSASQWYTKHHNN, (SEQ ID NO: 86)

SVSASQWYTKHHNNA, (SEQ ID NO: 87)

VSASQWYTKHHNNAT, (SEQ ID NO: 88)

SASQWYTKHHNNATT, (SEQ ID NO: 89)

ASQWYTKHHNNATTS, (SEQ ID NO: 90)

SQWYTKHHNNATTSI, (SEQ ID NO: 91)

and

QWYTKHHNNATTSIT. (SEQ ID NO: 92)

These partial peptides each comprise an amino acid sequence constituting an epitope in IgE.

All of these partial peptides can be used as a peptide vaccine for the treatment of allergic diseases. For example, the following peptides are preferred:

(1)
QEKKTSVSASQWYTKHHNNATTSI (SEQ ID NO: 29)

(2)
QEKKTSVSASQWYTKHHNNATTS (SEQ ID NO: 31)

(3)
QEKKTSVSASQWYTKHHNNATT (SEQ ID NO: 34)

(4)
QEKKTSVSASQWYTKHHNNAT (SEQ ID NO: 38)

(5)
QEKKTSVSASQWYTKHHNNA (SEQ ID NO: 43)

(6)
QEKKTSVSASQWYTKHHNN (SEQ ID NO: 49)

(7)
QEKKTSVSASQWYTKHHN (SEQ ID NO: 56)

(8)
QEKKTSVSASQWYTKHH (SEQ ID NO: 64)

(9)
QEKKTSVSASQWYTKH (SEQ ID NO: 72)

(10)
QEKKTSVSASQWYTK (SEQ ID NO: 82)

(11)
EKKTSVSASQWYTKHHNNATTSIT (SEQ ID NO: 30)

(12)
KKTSVSASQWYTKHHNNATTSIT (SEQ ID NO: 33)

(13)
KTSVSASQWYTKHHNNATTSIT (SEQ ID NO: 37)

(14)
TSVSASQWYTKHHNNATTSIT (SEQ ID NO: 42)

(15)
SVSASQWYTKHHNNATTSIT (SEQ ID NO: 48)

(16)
VSASQWYTKHHNNATTSIT (SEQ ID NO: 55)

(17)
SASQWYTKHHNNATTSIT (SEQ ID NO: 63)

(18)
ASQWYTKHHNNATTSIT (SEQ ID NO: 71)

(19)
SQWYTKHHNNATTSIT (SEQ ID NO: 81)

(20)
QWYTKHHNNATTSIT (SEQ ID NO: 92)

The following peptides are more preferred:
(1)
QEKKTSVSASQWYTKHHNNATTSI (SEQ ID NO: 29)

(2)
QEKKTSVSASQWYTKHHNNATTS (SEQ ID NO: 31)

(3)
QEKKTSVSASQWYTKHHNNATT (SEQ ID NO: 34)

(4)
QEKKTSVSASQWYTKHHNNAT (SEQ ID NO: 38)

(5)
QEKKTSVSASQWYTKHHNNA (SEQ ID NO: 43)

(7)
QEKKTSVSASQWYTKHHN (SEQ ID NO: 56)

(8)
QEKKTSVSASQWYTKHH (SEQ ID NO: 64)

(10)
QEKKTSVSASQWYTK (SEQ ID NO: 82)

(11)
EKKTSVSASQWYTKHHNNATTSIT (SEQ ID NO: 30)

(13)
KTSVSASQWYTKHHNNATTSIT (SEQ ID NO: 37)

(14)
TSVSASQWYTKHHNNATTSIT (SEQ ID NO: 42)

(15)
SVSASQWYTKHHNNATTSIT (SEQ ID NO: 48)

(16)
VSASQWYTKHHNNATTSIT (SEQ ID NO: 55)

A peptide consisting of an amino acid sequence derived from the amino acid sequence of the peptide consisting of the amino acid sequence represented by SEQ ID NO: 27, by the removal of 1 to 3, for example, 2 N-terminal amino acids or by the removal of 1 to 3, for example, 3 C-terminal amino acids can also be preferably used as a peptide vaccine. Examples of such peptides include a peptide consisting of the amino acid sequence represented by KKTS-VSASQWYTKHHNNATT (SEQ ID NO: 45).

The peptide of the present invention further encompasses a partial peptide consisting of an amino acid sequence derived from the amino acid sequence represented by NVTWNQEKKTSVSASQWYTKHHNNATTSITSILPV (SEQ ID NO: 28) or QEKKTSVSASQWYTKHHN-NATTSIT (SEQ ID NO: 27), or any of the aforementioned partial amino acid sequences (of at least 6, preferably at least 10 consecutive amino acids) of the amino acid sequence by the deletion, substitution, or addition of 1 to 3, preferably 1 or 2, more preferably 1 amino acid(s).

The partial peptide of mouse IgE has low amino acid sequence identity to IgE of other animals (e.g., dogs or humans) affected by allergic diseases, but exhibits cross reactivity therewith. In short, an antibody against the partial peptide of mouse IgE recognizes and binds to even dog IgE or human IgE.

Because of this low sequence identity, the partial peptide of mouse IgE, for example, when administered to a dog, induces the production of an IgE-specific IgG antibody against mouse IgE in vivo in the dog without being recognized as a self-antigen. The produced IgG antibody binds to the CH3 region of the dog's own IgE in the dog body and thereby blocks the binding of this IgE to an IgE receptor on mast cells or basophils so that the occurrence of allergy symptoms is prevented. Thus, the partial peptide can be used as an IgE peptide vaccine for the prevention or treatment of allergic diseases. The present invention encompasses an IgE peptide vaccine for the prevention or treatment of allergic diseases, comprising the partial peptide. The IgE peptide vaccine may comprise only one aforementioned partial peptide of mouse IgE or two or more aforementioned partial peptides of mouse IgE. The peptide vaccine of the present invention can exert vaccine effects through the administration (e.g., subcutaneous administration) of the peptide alone without the use of an adjuvant.

Figures 2, 3:
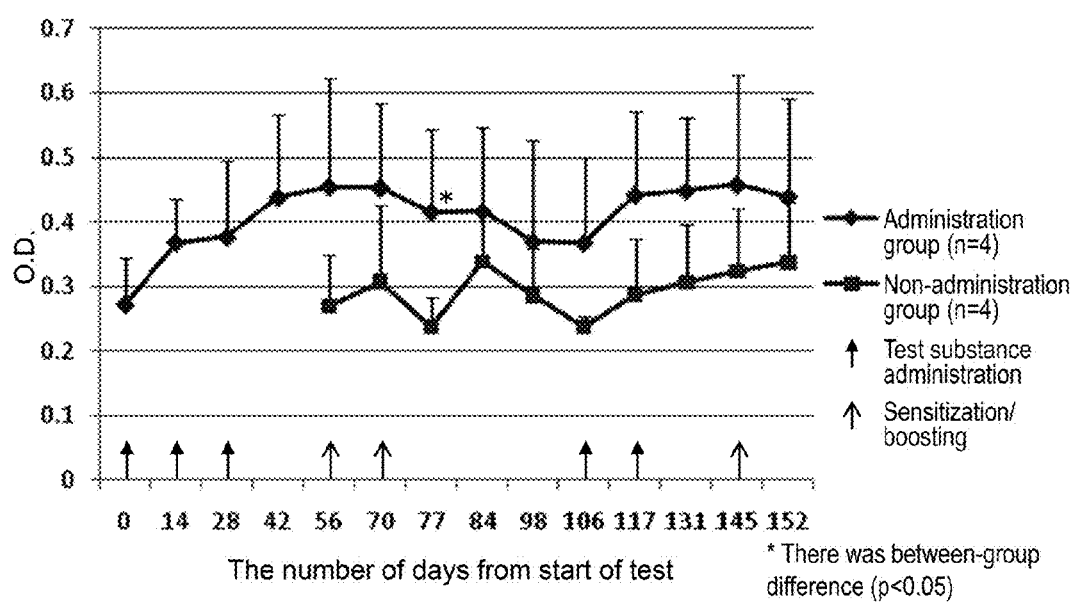

SEQ ID NO: 1 shows the amino acid sequence of the dog IgE CH3 region. SEQ ID NO: 21 shows the amino acid sequence of the mouse IgE CH3 region. The sequence represented by SEQ ID NO: 27 corresponds to an amino acid sequence of positions 45 to 70 in the amino acid sequence represented by SEQ ID NO: 21. FIG. 1-2 shows the alignment of these amino acid sequences.

The IgE peptide vaccine of the present invention can be administered to mammalian recipients other than mice, such as dogs, cats, or humans, which may be affected by IgE-mediated diseases such as allergic diseases.

Some allergic diseases are IgE-mediated and others are not. Examples of the IgE-mediated allergic diseases include allergic dermatitis, atopic dermatitis, pollinosis, food allergy, allergic rhinitis, bronchial asthma, allergic conjunctivitis, mite (house dust mite) allergic disease, hives, anaphylactic shock, and PIE (pulmonary infiltration with eosinophilia) syndrome. Examples of the mite allergy include mite allergy caused by *Dermatophagoides farinae*, *Dermatophagoides pteronyssinus*, or the like belonging to the genus *Dermatophagoides* of the family Pyroglyphidae.

The dose of the IgE peptide vaccine of the present invention can vary depending on an animal species as a recipient and is dozens of ng to a few mg per dose. The IgE peptide vaccine of the present invention may be administered in a single dose or may be administered in several doses at 2-day to 8-week intervals.

The IgE peptide vaccine of the present invention may be in the form of a sterile aqueous or nonaqueous solution, suspension, or emulsion. The IgE peptide vaccine of the present invention may further contain, for example, a pharmaceutically acceptable diluent, auxiliary, or carrier including salts, buffers, and adjuvants. The vaccine can be inoculated through each route such as an oral, transnasal, transmucosal, intramuscular, subcutaneous, intranasal, intratracheal, dermal, percutaneous, intracutaneous, or intravenous route. Among them, oral inoculation, transnasal inoculation, transmucosal inoculation, subcutaneous administration, or intravenous administration is preferred. Examples of the adjuvant that may be used include complete or incomplete Freund's adjuvants as well as adjuvants known in the art such as bacteria and their cell components, mycobacteria, Gram-negative bacteria and their cell components, Gram-positive bacteria and their cell components, non-bacterial substances, plant or fungus polysaccharides, fat-soluble vitamins, and mineral oils. Examples of the non-bacterial substances include an alum (aluminum hydroxide) adjuvant, a calcium phosphate adjuvant, an aluminum phosphate adjuvant, and alum. Alternatively, the vaccine of the present invention may be administered in a state contained in drinking water or feed to animals such as dogs. The present invention also encompasses drinking water and feed comprising the vaccine.

The present invention further encompasses a method for preventing or treating an IgE-mediated allergic disease in an animal, preferably a nonhuman animal, comprising administering the IgE peptide vaccine to the animal to allow the animal to produce an IgG antibody specifically binding to IgE of the animal, thereby blocking the binding of this IgE to mast cells or basophils.

EXAMPLES

Hereinafter, the present invention will be described specifically with reference to Examples. However, the present invention is not intended to be limited by these Examples.

Example 1 Analysis of IgE CH3 Region Peptide

Epitope analysis was conducted on mouse monoclonal antibodies binding to a dog IgE antibody and rat monoclonal antibodies binding to dog and mouse IgE antibodies. Mouse anti-dog IgE antibodies (clone name: CCH3-4, CCH5-5, CCH3-12, CCH3-13, CCH3-14, and CCH3-15) were prepared from mice immunized with the dog IgE CH3 (Cε3) region gene. Also, anti-IgE monoclonal antibodies (clone name: X-1, X-2, CCH3-21, and CCH3-22) were prepared from rats immunized with the dog and mouse IgE CH3 (Cε3) region genes. These antibodies were used as samples to synthesize synthetic peptides (SEQ ID NOs: 2 to 20 and 22 to 26) of the dog and mouse IgE peptide CH3 (Cε3) regions consisting of the sequences shown in FIG. 1-1. The epitope analysis was conducted by ELISA. Clones X-1 and X-2 prepared using rats were confirmed to react with both mouse IgE and dog IgE. Each peptide was immobilized at a concentration of 100 ng/well onto an ELISA plate and reacted with the anti-dog IgE mouse monoclonal antibodies (CCH3-4, CCH5-5, CCH3-12, CCH3-13, CCH3-14, and CCH3-15 shown in FIG. 2), the anti-dog/mouse IgE rat monoclonal antibodies (X-1 and X-2 shown in FIG. 2), and the anti-dog IgE rat monoclonal antibodies (CCH3-21 and CCH3-22 shown in FIG. 2). The anti-dog IgE monoclonal antibodies that responded to the peptide were detected using secondary antibodies (anti-mouse IgG HRP (horseradish peroxidase)-labeled antibody for the anti-dog IgE antibodies prepared using mice, and anti-rat IgG HRP-labeled antibody for the anti-dog IgE antibodies prepared using rats).

FIG. 2 shows exemplary results of the epitope analysis. Dog IgE was found to contain epitopes at underlined sites of SEQ ID NOs: 9 to 15 in the sequences of FIG. 1-1. Also, mouse IgE was found to contain epitopes at underlined sites of SEQ ID NOs: 22 to 26 in the sequences of FIG. 1-1.

These results demonstrated that a peptide consisting of the amino acid sequence represented by QEKKTSVSASQWYTKHHNNATTSIT (SEQ ID NO: 27) in the CH3 (Cε3) region of the mouse IgE peptide is a peptide of an epitope region.

Example 2 Antibody Response of IgE Peptide Vaccine in Dog (1) Peptide

The peptide used was MOUSE CH3-4-17-11 (mouse CH3 region amino acid sequence) (SEQ ID NO: 27). 2 mL (500 µg) of a solution of the peptide (concentration: 250 µg/mL) and 2 mL of a complete adjuvant (DIFCO ADJUVANT COMPLETE FREUND, Becton, Dickinson and Company Japan) were dispensed to microtubes. Liquids (4 mL per animal) emulsified by shaking for 15 minutes in a high-speed shaker were used as IgE peptide vaccines.

(2) Administration of Vaccine

The animals used were 1 male and 7 females of 5- to 7-month-old beagles and were divided into an administration group (n=4; 08-33, 08-42, 08-43, and 08-44) and a non-administration group (n=4; 08-45, 08-46, 08-47, and 08-48).

The peptide was administered at days 0 (test start date), 14, and 28 in the first course and further at days 106 and 117 in the second course. The test substance was subcutaneously administered to the necks of the 4 animals in the administration group. The non-administration group was untreated.

(3) Artificial Sensitization with House Dust Mite Antigen (Der f 2)

Four weeks after the completion of the peptide administration of the first course (days 56 and 70 into the test), all of the animals were artificially sensitized. A mixed liquid (4.0 mL per animal) of 300 µg of Der f 2 (Lot No. 3, 1465 µg/mL, prepared by a drug research team) and 50 mg of an alum adjuvant (SIGMA® Aluminium hydrate IgE1, 13 mg/mL) was used as a sensitizing solution and administered intraperitoneally for the first shot and subcutaneously to the necks for the second shot.

(4) Boosting of Artificial Sensitization

Four weeks after the completion of the peptide administration of the second course (day 145 into the test), the artificial sensitization was boosted. A 1-mL solution prepared from Der f 2 (Lot No. 3: 0.205 mL of 1465 µg/mL: 300 µg) with saline was subcutaneously administered to the necks of all of the animals.

(5) Measurement of IgG Concentration in Serum

IgG concentrations in the serum of the dog subjects thus given the peptide and artificially sensitized were measured by the method described below.

At days 0, 14, 28, 42, 56, 70, 77, 84, 98, 106, 117, 131, 145, and 152 (4 time points (0, 14, 28, and 42) were excluded for the non-administration group), blood was collected from the jugular vein of each individual using a syringe. After separation of serum, the serum was used to measure peptide-specific IgG concentrations and IgE-specific IgG concentrations in the serum.

Each antigenic protein (MOUSE CH3-4-17-11 for peptide-specific IgG assay, and human IgE for IgE-specific IgG assay) was prepared at 1 µg/mL in an immobilization buffer (0.05 M carbonate buffer, pH 9.6), then added at a concentration of 100 µL/well to an ELISA plate, and left overnight at 4° C. The immobilization plate was washed once with PBS-T (0.05%). A blocking solution (4× Block Ace, Snow Brand Milk Products Co., Ltd.; UK-B80) was added thereto at a concentration of 200 µL/well. The plate was blocked by incubation at 37° C. for 1.5 hours. The serum was diluted 5000-fold with a diluent (PBS-T:Block Ace=9:1) and used. The plate was reacted with the serum at 37° C. for 1.5 hours and washed three times with PBS-T (0.05%). An anti-dog IgG antibody (Bethyl Laboratories, Inc.; A40-118P) was diluted 5000-fold with a diluent and added thereto as a secondary antibody at a concentration of 100 µL/well. After reaction at 37° C. for 1.5 hours, the plate was washed three times with PBS-T (0.05%). A substrate solution (citrate buffer supplemented with one TMBZ tablet (Sigma-Aldrich Corp.; T-3405) and further supplemented, immediately before use, with 2 µL of 30% $H_2O_2$) was added at a concentration of 100 µL/well to the plate and reacted therewith for 10 minutes. The reaction was terminated by the addition of 2 N sulfuric acid at a concentration of 50 µL/well. Then, the measurement was performed using a plate reader (Bio-Rad Laboratories, Inc.; model 680) (dual: measurement: 450 nm, control: 570 nm).

In this context, if dog IgE is used as an immobilized antibody for the ELISA measurement of IgE-specific IgG concentrations, the dog IgG-specific polyclonal antibody used as a secondary antibody may bind to the immobilized antibody to cause nonspecific reaction. For this reason, human IgE was used as the immobilized antibody.

Serum obtained at days 70, 77, 106, 117, 131, 145, and 152 were used in the measurement of Der f 2-specific IgE concentrations in the serum, which was consigned to AAC Laboratories Inc.

(6) Results

FIG. 3-1 shows the results (O.D. values) of measuring peptide-specific IgG concentrations in serum. At days 0 through 106, the average of the administration group fluctuated in a range from 0.16 to 0.30. At day 117 or later (second course), only one animal (08-44) exhibited a value of 1.0 or larger, and the average of the administration group fluctuated in a range from 0.46 to 0.66. The average of the non-administration group fluctuated in a range from 0.14 to 0.23. At day 77, the average of the administration group was significantly higher than that of the non-administration group ($p<0.05$).

FIG. 3-2 shows the results (O.D. values) of measuring IgE-specific IgG concentrations in serum. The average of the administration group fluctuated in a range from 0.27 to 0.46. The average of the non-administration group fluctuated in a range from 0.24 to 0.34. At day 77, the average of the administration group was significantly higher than that of the non-administration group ($p<0.05$).

Figure 4:
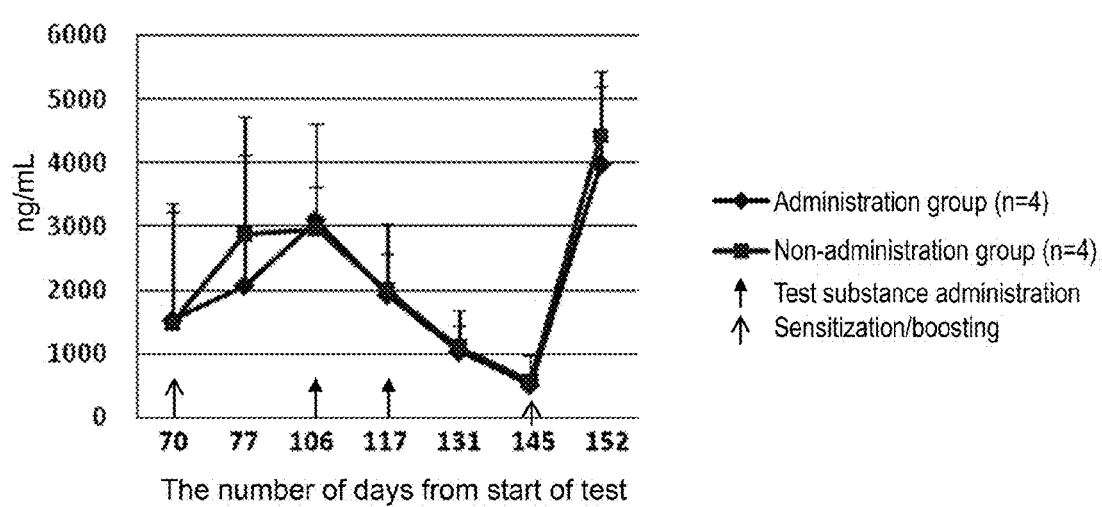
FIG. 4 is a diagram showing results of measuring Der f 2-specific IgE concentrations in serum.

FIG. 4 shows the results of measuring Der f 2-specific IgE concentrations in serum. At day 70 (2 weeks after the first sensitization), the administration group had a concentration of 1528.8±1823.6 ng/mL (2 animals had a concentration of 0), whereas the non-administration group had a concentration of 1486.3±1736.1 ng/mL (2 animals had a concentration of 0). At days 77 and 106, both of the administration group and the non-administration group exhibited a rise in concentration, which peaked at day 106 at 3091.8±1542.6 ng/mL in the administration group and 2968.3±649.8 ng/mL in the non-administration group and then decreased until day 145. At day 152 (7 days after the boosting), the concentration elevated again to 3972.5±1216.5 ng/mL in the administration group and 4426.7±1015.7 ng/mL in the non-administration group. At all of the time points, no significant difference was observed between the administration group and the non-administration group.

As a result of measuring peptide-specific IgG concentrations in serum, the peptide-specific IgG concentration was significantly higher at day 77 in the administration group than in the non-administration group, showing that the dog given the IgE peptide vaccine produced peptide-specific IgG into its serum. In the second course, peptide-specific IgG sharply elevated in one animal (08-44) in the administration group, suggesting that the test substance administered in the second course to this one animal exerted boosting effects.

In the measurement of IgE-specific IgG concentrations in serum, the IgE-specific IgG concentration tended to be high in the administration group compared with the non-administration group and was significantly higher at day 77 in the administration group than in the non-administration group, suggesting that peptide-specific IgG produced in the administration group is an antibody that cross-recognizes the peptide and an IgE CH3 region structurally similar thereto.

Figure 5:
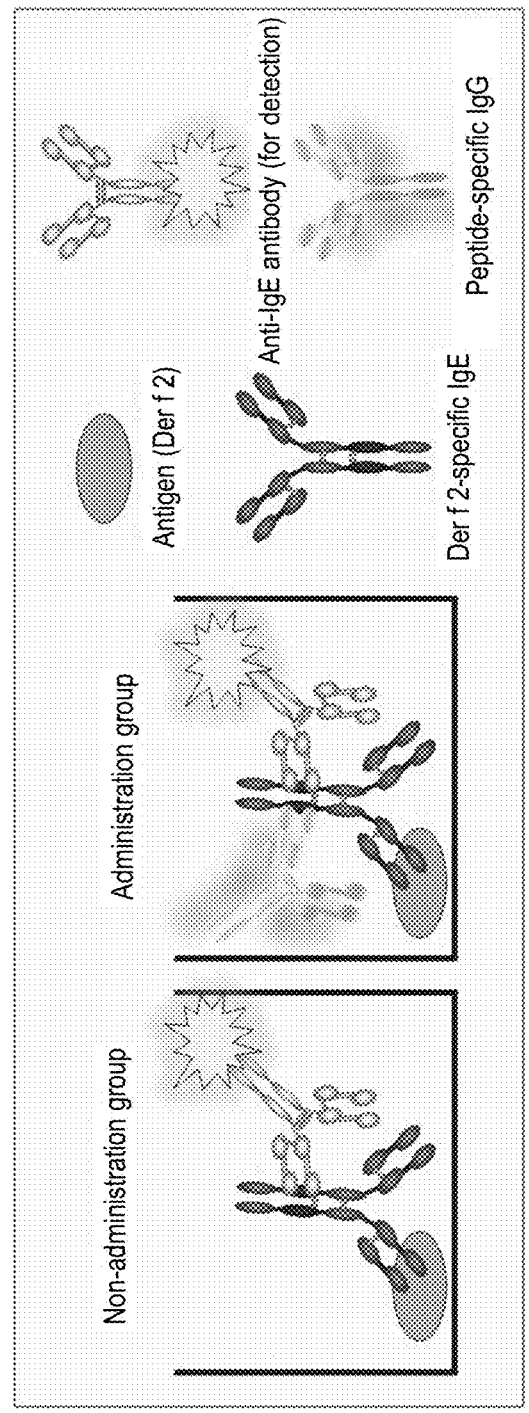
FIG. 5 is a diagram showing reaction patterns of ELISA reaction systems of peptide non-administration and administration groups in the measurement of IgE concentrations in serum.

As a result of measuring Der f 2-specific IgE concentrations in serum, no significant difference was observed between the administration group and the non-administration group. A possible reason why no significant difference in Der f 2-specific IgE concentration in serum was observed between the administration group and the non-administration group, in spite of the indication that anti-peptide IgG was produced in the serum of the administration group and bound to IgE in this serum, was that one IgE molecule has two CH3 regions; thus, even if one CH3 region was blocked by IgG, the anti-dog IgE antibody (antibody recognizing the IgE CH3 region) used in the detection was still capable of binding to another CH3 region, resulting in no observable color difference in ELISA (FIG. 5).

The results of this Example revealed the following:

1) An anti-peptide antibody (IgG) was produced by the administration of an IgE peptide vaccine prepared with a mouse CH3 region as a template.

2) This antibody recognized and bound to the CH3 region of dog IgE. Thus, the antibody was considered to bind to Der f 2-specific IgE produced by sensitization with Der f 2. An IgE-IgG complex was detected by an ELISA system used in this test. No between-group difference from the non-administration group was observed in Der f 2-specific IgE concentration in serum.

3) In an attempt to confirm effects by an intracutaneous reactivity test at this time, it would appear that the elevated level of Der f 2-specific IgE in serum allows IgE to bind to the surface of mast cells in the skin and to have reactivity against the antigen for a few month. Thus, even if the intracutaneous reactivity test is carried out at this time, no between-group difference may be observed.

4) It was believed that the formation of an IgE-IgG complex can be proven in vivo by Prausnitz-Kustner (P-K) test (using unsensitized dogs) capable of qualitatively evaluating IgE irrespective of the state of mast cells in dogs under test.

The maximum Der f 2-specific IgE concentration in serum in this test was as high as 5000 ng/mL or higher. When the test substance was administered to individuals having a serum concentration of Der f 2-specific IgE equivalent to that in allergy-affected animals (approximately 10 to 1000 ng/mL), IgG in serum bound to IgE at a higher rate, suggesting that a difference may be observed in an IgE detection system used in this test.

Subsequently, the reactivity between each immobilized antigen (IgE peptide and IgE) and each detection antigen (anti-dog IgG antibody, anti-dog IgG1 antibody, and anti-dog IgG2 antibody) was analyzed to confirm analytes having no nonspecific reaction (circle in FIG. 6-1) and analytes having nonspecific reaction (x-mark in FIG. 6-1). The combination of analytes free from nonspecific reaction was examined for their reactivity.

Figure 6:
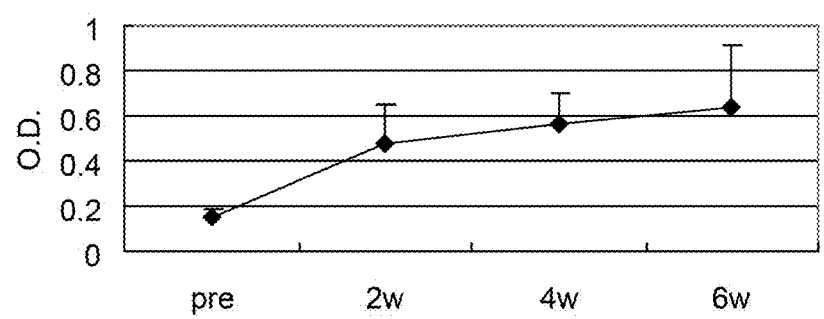
Figure 2:
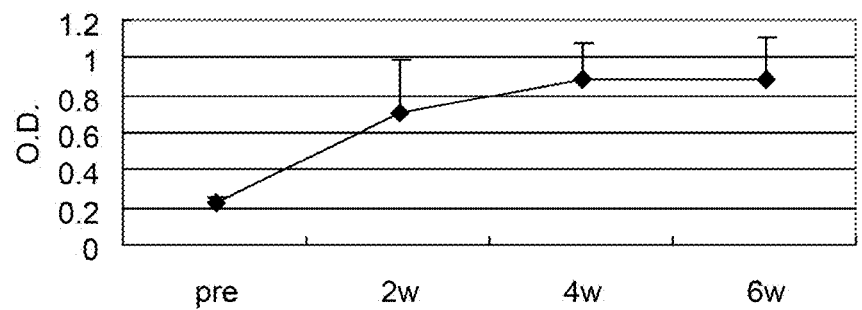
Figure 6:
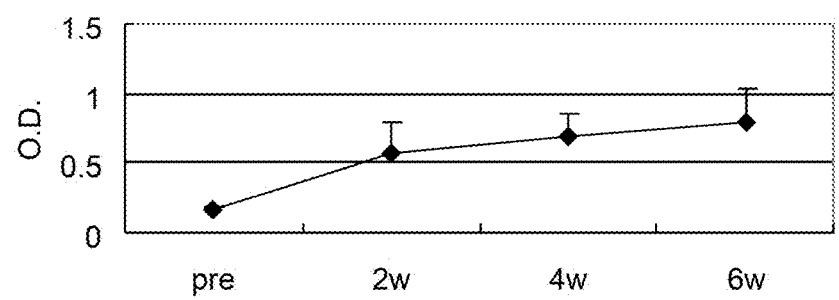
Figure 4:
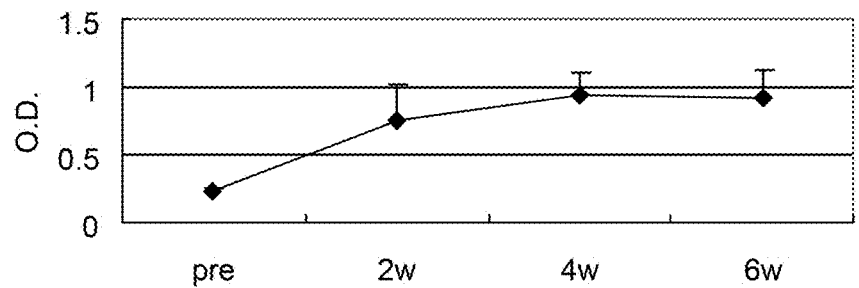
Figures 5, 6:
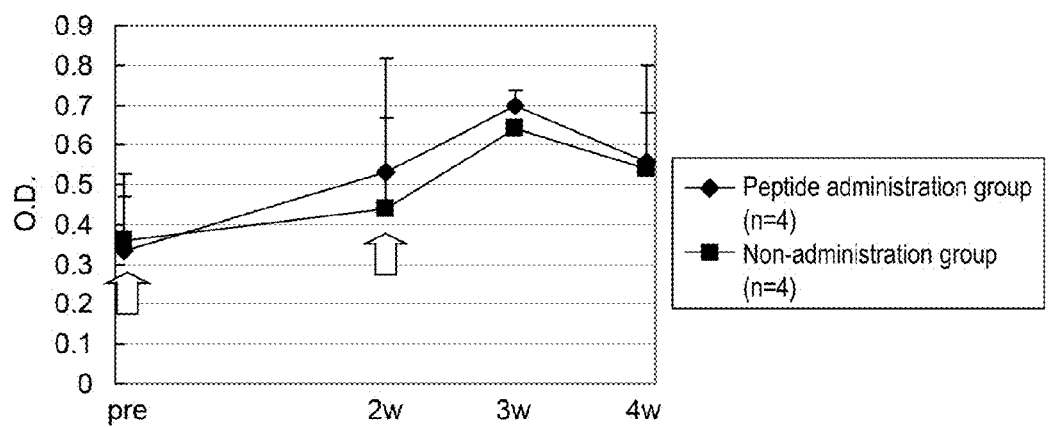

FIG. 6-2 shows the results of analyzing the reactivity between each antigen (IgE peptide and human IgE) and the anti-dog IgG antibody. FIG. 6-3 shows the results of analyzing the reactivity between each antigen (IgE peptide, human IgE, and dog IgE) and the anti-dog IgG1 antibody. FIG. 6-4 shows the results of analyzing the reactivity between each antigen (IgE peptide and human IgE) and the anti-dog IgG2 antibody. FIG. 6-5 shows the results of analyzing the reactivity of Der f 2-specific IgE after administration of the peptide and subsequent immunization (artificial sensitization) with Der f 2 together with an alum adjuvant. FIG. 6-6 shows levels of human IgE-specific dog IgG, IgG1, and IgG2 in the serum of a dog immunized (artificially sensitized) with Der f 2 together with an alum adjuvant, and shows the comparison of the results about the peptide vaccine administration and non-administration groups. This diagram also shows results about the serum of untreated healthy dogs.

These results demonstrated that: the administration of the peptide vaccine increased both the levels of an IgG antibody against the peptide and an IgG antibody against IgE in dogs; and in the case of the subsequent production of IgE, the administration of the peptide vaccine inhibited the production of IgE.

Example 3 Study on Effect of IgE Peptide Vaccine

In IgE Example 2, no significant difference in Der f 2-specific IgE concentration in serum was observed between the administration group and the non-administration group, in spite of the indication that IgG capable of binding to IgE was produced in the serum of the peptide vaccine administration group and bound to Der f 2-specific IgE produced by sensitization. A possible reason therefor was that IgG-bound IgE was detected similarly to unbound IgE in the ELISA method of Example 2. Even if an intracutaneous reactivity test is carried out at this time, no difference may be observed.

Thus, in order to prove the binding of IgG to Der f 2-specific IgE in the serum of the administration group, the Prausnitz-Kustner (P-K) test was planned. This test was carried out in the expectation that, in the serum of the administration group, IgG bound with IgE inhibits the binding of this IgE to the surface of mast cells so that flare is unlikely to occur (degranulation may be inhibited) in the P-K test.

(1) Summary of P-K Test

The P-K test refers to a method for qualitatively evaluating antigen-specific IgE in test serum and employs additional antigen-unsensitized individuals. The test is summarized as follows:

1) Antigen-unsensitized animals are prepared as animals subjected to the P-K test.

2) Test serum or serum of a healthy animal (control) is intracutaneously administered to the animals subjected to the P-K test. When antigen-specific IgE is present in the test serum, the IgE binds to the surface of mast cells in the skins of the animals subjected to the P-K test within 48 hours after the administration.

3) 48 hours after the serum administration, an antigen solution is intracutaneously administered to the same sites as above. When antigen-specific IgE is present in the test serum, the antigen binds to the antigen-specific IgE bound with the surface of mast cells to form IgE cross-linking. This triggers the degranulation of the mast cells, resulting in flare confirmed in the skins.

(2) Material

The administration group and the non-administration group differed most largely in their serum Der f 2-specific IgE concentrations at day 77 (7 days after the second sensitization) when the effects of the test substance were thus confirmed to be maximized. The animal 08-43 in the administration group, however, was excluded from the P-K test of this Example, because the effects of the test substance were confirmed to be absent in view of its markedly high serum concentration of Der f 2-specific IgE which was two times or more the average of the group. Thus, the pooled serum of the other animals in the administration group was used in this test. As for the non-administration group, the pooled serum of all of the animals was used. In order to compare IgE functions, the Der f 2-specific IgE in the serum of the non-administration group was adjusted so as to have the same concentration as that of the administration group.

Serum collected in Example 1 and healthy dog serum
Serum 1: pooled serum (day 77) of the non-administration group (adjusted with saline so as to have a Der f 2-specific IgE concentration equal to that of serum 2)
Serum 1 was prepared as follows: the average of Der f 2-specific IgE concentrations in the serum of the administration group (3 animals; excluding 08-43) was 1352.3 ng/mL, while the average of the non-administration group (4 animals) was 2879.3 ng/mL. The pooled serum of the non-administration group was diluted with saline to adjust the Der f 2-specific IgE concentration to 1352.3 ng/mL.
Serum 2: pooled serum (day 77) of the administration group (excluding 08-43)
Serum 3: pooled serum (day 77) of the non-administration group
Serum 4: pooled serum of 10 healthy dogs Serum 1 to serum 4 mentioned above were diluted 5-fold and 10-fold with saline to prepare reagents for the study of optimum conditions. The antigen solution (undiluted) used was a 1465 µg/mL solution prepared from Der f 2 Lot No. 3.

(3) Dog Subjected to P-K Test

Two males (02-97 and 03-48) and 1 female (04-14) of 5- to 6-year-old beagles that had not previously been subjected to Der f 2-related tests were used. Before the test, the absence of nonspecific reaction caused by intracutaneous administration was confirmed. For this purpose, Der f 2 was diluted with saline ("Saline V Injection Solution for Animals"; Nippon Zenyaku Kogyo Co., Ltd.), and 0.05 mL of the 10 μg/mL solution thus prepared was intracutaneously administered to each dog to confirm that no flare occurred.

(4) P-K Test Method (i) Administration of Serum

The serum was administered 2 days before administration of the antigen solution. A mixture of medetomidine hydrochloride ("Domitor®"; Nippon Zenyaku Kogyo Co., Ltd., 0.03 mL/kg) and midazolam ("Dormicum®"; Yamanouchi Pharmaceutical Co., Ltd., 0.06 mL/kg) was intramuscularly administered for sedation treatment to the hips of the dogs subjected to the P-K test. The side of the abdomens was shaved with a hair clipper, and the administration sites were marked using oil-based marker pen.

Figure 7:
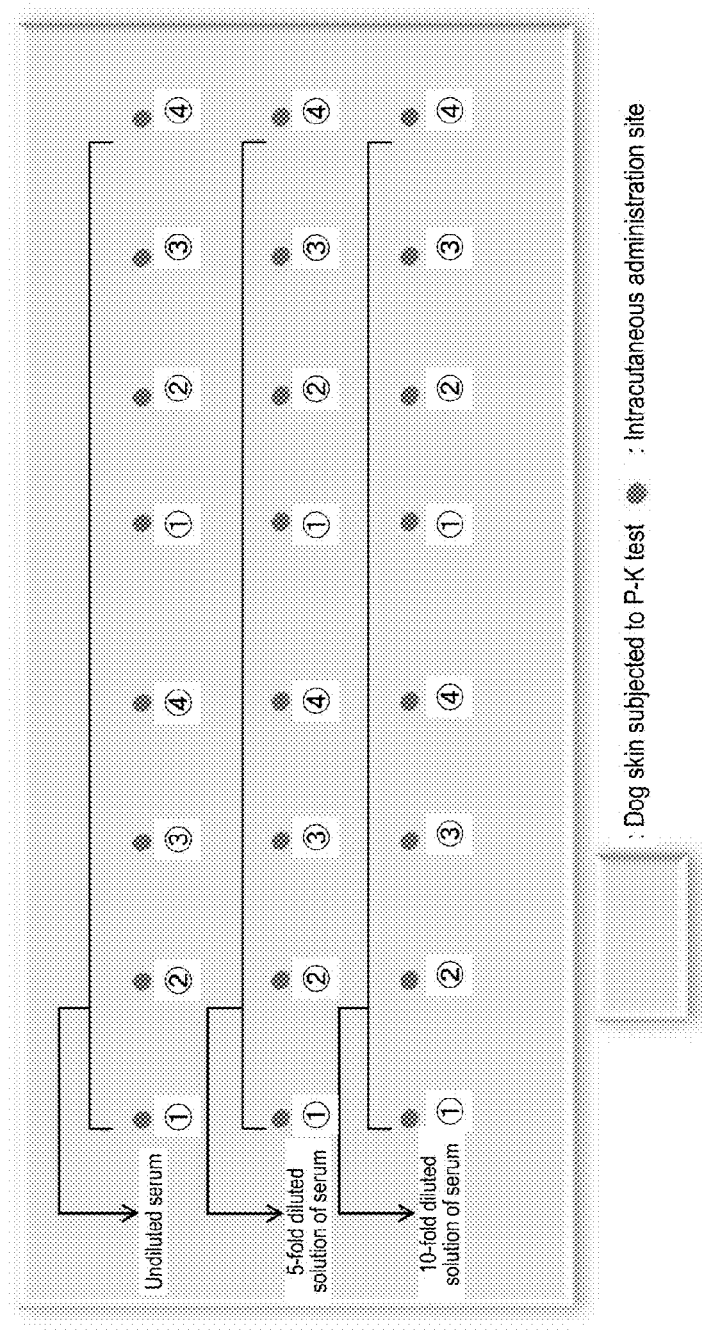
FIG. 7 is a diagram showing a serum administration method in Prausnitz-Kustner (P-K) test. In the drawing, circled numbers 1 to 4 denote serum 1 to serum 4, respectively.

The undiluted, 5-fold diluted, and 10-fold diluted solutions of serum 1 to serum 4 were intracutaneously administered at a dose of 0.05 mL×2 sites using B-D disposable syringe for trace amount (Becton, Dickinson and Company Japan) (FIG. 7).

The individuals that finished the administration were awaken by the intramuscular administration of atipamezole hydrochloride ("Antisedan®"; Nippon Zenyaku Kogyo Co., Ltd., 0.03 mL/kg) to the hips.

(ii) Administration of Antigen Solution and Assessment

Figure 8:
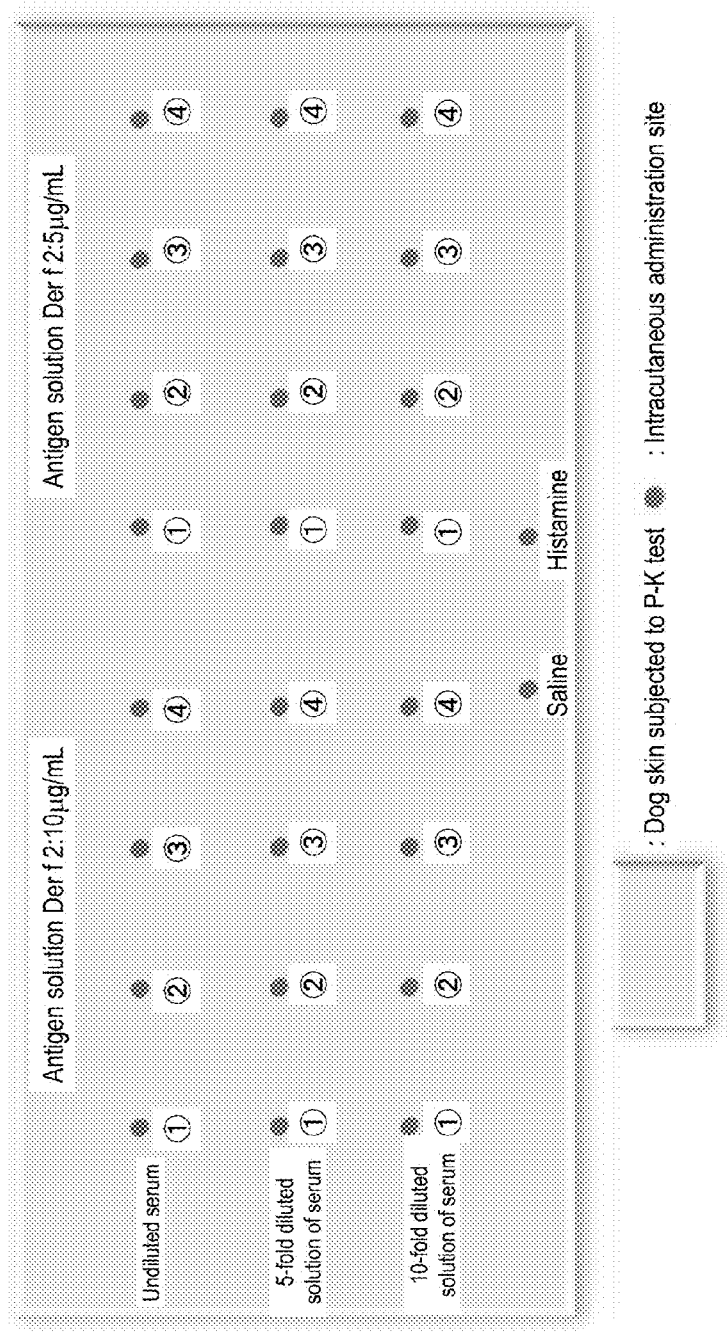
FIG. 8 is a diagram showing administration methods of an antigen solution and positive and negative controls in Prausnitz-Kustner (P-K) test. In the drawing, circled numbers 1 to 4 denote serum 1 to serum 4, respectively.

Two days after the serum administration, each antigen solution was intracutaneously administered to the same sites as the serum administration sites. Sedation and awakening treatments were performed in the same way as in the preceding paragraph (i). The antigen solutions used were 10 μg/mL and 5 μg/mL solutions prepared from Der f 2 with saline, and each intracutaneously administered to the serum administration sites described in the paragraph (i). A histamine solution (0.0275 mg/mL) and saline were intracutaneously administered as a positive control and a negative control, respectively, to different sites (FIG. 8).

The diameters of flare portions were temporally measured up to 15 minutes after the administration of the antigen solutions, and the portions were photographed. Assessment was made when the macroscopically clearest flare occurred. The flare was scored according to the following criteria:

Scoring Criteria for Flare Diameter

+++ . . . Equivalent to or larger than the diameter of flare in the positive control group ++ . . . Equivalent to or larger than the average of the positive control and negative control groups + . . . Smaller than the average of the positive control and negative control groups and larger than the diameter of flare in the negative control group − . . . Equal to or smaller than the diameter of flare in the negative control group (iii) Setting of Optimum Condition In order to set the optimum conditions for studying the difference between the administration group and the non-administration group, 6 conditions involving varying serum dilution ratios and Der f 2 solution concentrations were studied.

Undiluted serum+10 μg/mL Der f 2
Undiluted serum+5 μg/mL Der f 2
5-fold diluted serum solution+10 μg/mL Der f 2
5-fold diluted serum solution+5 μg/mL Der f 2
10-fold diluted serum solution+10 μg/mL Der f 2
10-fold diluted serum solution+5 μg/mL Der f 2

Of these conditions, conditions that satisfied criteria given below in 2 or more out of 3 dogs subjected to the P-K test were adopted.

1) The administration sites given the serum of healthy dogs (serum 4) get the score of −.

2) The administration sites given the serum of the non-administration group (serum 1 and serum 3) get the score of + or greater.

(5) Results

The results are shown in Tables 1 to 6.

Also, the results about 03-48 among the taken photographs are representatively shown in FIG. 9.

TABLE 1

P-K test results (undiluted serum + 10 μg/mL Der f 2)

| | | Intracutaneously administered antigen Der f 2 10 μg/mL | | | |
|---|---|---|---|---|---|
| Serum | | ① | ② | ③ | ④ |
| Dog subjected to P-K test | 02-97 | ++ | ++ | ++ | − |
| | 03-48 | ++ | ++ | ++ | − |
| | 04-14 | − | − | ++ | − |

TABLE 2

P-K test results (undiluted serum + 5 μg/mL Der f 2)

| | | Intracutaneously administered antigen Der f 2 5 μg/mL | | | |
|---|---|---|---|---|---|
| Serum | | ① | ② | ③ | ④ |
| Dog subjected to P-K test | 02-97 | ++ | − | + | − |
| | 03-48 | ++ | − | ++ | − |
| | 04-14 | − | − | − | − |

TABLE 3

P-K test results (5-fold diluted serum solution + 10 μg/mL Der f 2)

| | | Intracutaneously administered antigen Der f 2 10 μg/mL | | | |
|---|---|---|---|---|---|
| Serum | | ① | ② | ③ | ④ |
| Dog subjected to P-K test | 02-97 | ++ | − | ++ | − |
| | 03-48 | ++ | − | ++ | − |
| | 04-14 | ++ | − | − | − |

TABLE 4

P-K test results (5-fold diluted serum solution + 5 μg/mL Der f 2)

| | | Intracutaneously administered antigen Der f 2 5 μg/mL | | | |
|---|---|---|---|---|---|
| Serum | | ① | ② | ③ | ④ |
| Dog subjected to P-K test | 02-97 | − | − | − | − |
| | 03-48 | − | − | + | − |
| | 04-14 | − | − | − | − |

TABLE 5

P-K test results (10-fold diluted serum solution + 10 μg/mL Der f 2)

| | | Intracutaneously administered antigen Der f 2 10 μg/mL | | | |
|---|---|---|---|---|---|
| Serum | | ① | ② | ③ | ④ |
| Dog subjected to P-K test | 02-97 | − | − | ++ | − |
| | 03-48 | − | − | ++ | − |
| | 04-14 | − | − | − | − |

TABLE 6

P-K test results (10-fold diluted serum solution + 5 μg/mL Der f 2)

|  |  | Intracutaneously administered antigen Der f 2 5 μg/mL | | | |
|---|---|---|---|---|---|
| Serum |  | ① | ② | ③ | ④ |
| Dog subjected to P-K test | 02-97 | – | – | – | – |
|  | 03-48 | – | – | – | – |
|  | 04-14 | – | – | – | – |

In Tables 1 to 6, circled numbers 1 to 4 denote serum 1 to serum 4, respectively.

(i) Setting of Optimum Condition

The results obtained from the 6 conditions were checked against the criteria shown in "(iii) Setting of optimum condition" of the paragraph (4).

1) The administration sites given the serum of healthy dogs (serum 4) get the score of –.

All of the 6 conditions fell under this criterion.

2) The administration sites given the serum of the non-administration group (serum 1 and serum 3) get the score of + or greater.

Three conditions ["undiluted serum+10 μg/mL Der f 2" (Table 1), "undiluted serum+5 μg/mL Der f 2" (Table 2), and "5-fold diluted serum solution+10 μg/mL Der f 2" (Table 3)] fell under this criterion.

Under the condition "undiluted serum+10 μg/mL Der f 2", no difference was observed between the scores of serum 1 and serum 2 in all of the 3 dogs subjected to the P-K test. Although the reason therefor is unknown, this condition involved undiluted serum and high concentration of the antigen solution (10 μg/mL Der f 2) in combination and might nonspecifically cause flare. Thus, this condition might fail to yield proper evaluation and therefore, was also rejected.

Thus, the results about two conditions ("undiluted serum+5 μg/mL Der f 2" and "5-fold diluted serum solution+10 μg/mL Der f 2" were discussed.

(ii) Results about Undiluted Serum+5 μg/mL Der f 2 (Table 2)

02-97 and 03-48 given serum 1 and serum 3 got the score of + or greater. 02-97 and 03-48 given serum 2 and serum 4 got the score of –. 04-14 given serum 1 to serum 4 got the score of – in all cases.

(iii) Results about 5-Fold Diluted Serum Solution+10 μg/mL Der f 2 (Table 3)

02-97 and 03-48 given serum 1 and serum 3 got the score of ++. 02-97 and 03-48 given serum 2 and serum 4 got the score of –. 04-14 given serum 1 got the score of ++. 04-14 given serum 2 to serum 4 got the score of –.

(6) Discussion

The serum 1 (serum of the non-administration group) and serum 2 (serum of the administration group) administration sites got the scores of ++ and –, respectively, in 2 out of the 3 dogs subjected to the P-K test under the condition "undiluted serum+5 μg/mL Der f 2" and in all of these 3 dogs under the condition "5-fold diluted serum solution+10 μg/mL Der f 2". FIG. 5 shows a reason why serum 1 and serum 2 having the same concentrations of Der f 2-specific IgE differed in score. At the serum 1 administration site, administered IgE highly frequently bound to mast cells present in the skin of each dog subjected to the P-K test to thereby establish Der f 2-mediated IgE cross-linking so that the mast cells were degranulated. By contrast, at the serum 2 administration site, IgG bound to the CH3 region of IgE and thereby blocked the binding of this IgE to mast cells. This seemed to hinder Der f 2-mediated IgE cross-linking and IgE response (FIG. 10).

Of the dogs subjected to the P-K test, 04-14 exhibited flare only by serum 3 under the condition "undiluted serum+ 10 μg/mL Der f 2", only by serum 1 under the condition "5-fold diluted serum solution+10 μg/mL Der f 2", and no flare under the remaining 4 conditions. Accordingly, 04-14 was found to have weaker flare reaction in the skin compared with other individuals.

These results demonstrated that: a dog given the IgE peptide vaccine composed of MOUSE CH3-4-17-11 produces, in its serum, IgG that cross-recognizes the peptide and dog IgE; and this IgG blocks the binding of the IgE to mast cells.

Example 4

2 mL of the 250 μg/mL peptide (a total of 500 μg) used in Example 2 was mixed with an equal amount of a complete adjuvant (a total of 4 mL). Each rabbit was immunized with this mixture by the subcutaneous administration (amount of the peptide: 500 μg) at day 0 and weeks 2, 4, 6, and 8. Blood was collected 5 weeks after the week-8 administration (week 13 counted from day 0). Booster immunization was performed at week 14 counted from day 0, and blood was further collected 2 weeks thereafter (week 16 counted from day 0). Antibody titers in the collected blood were measured by ELISA. The serum of a rabbit that received no peptide was used as a control.

ELISA was performed by the following method: each 1000 μg/mL recombinant CH3 solution of dog IgE, human IgE, mouse IgE, dog IgG, and cat IgE was immobilized at a concentration of 100 μL/well (100 ng/well) to a plate. The serum collected from the immunized rabbit was used (×200 to ×102400) as a primary antibody. An enzyme-labeled anti-rabbit IgG antibody (Zymed Laboratories Inc.) was used as a secondary antibody.

Figures 1, 11:
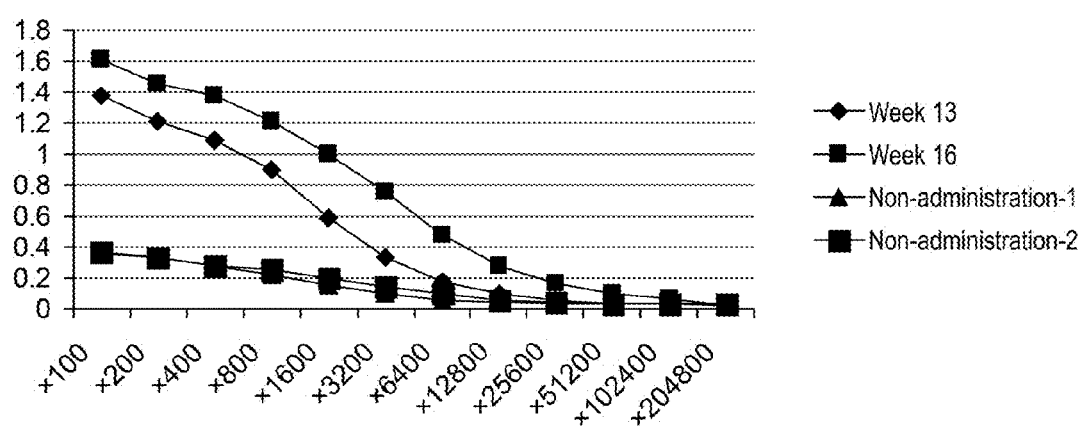
Figures 2, 11:
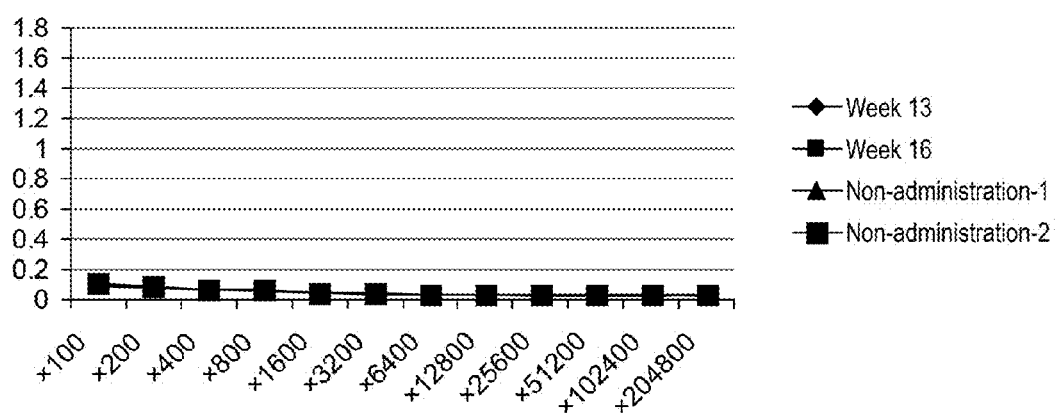
Figures 3, 11:
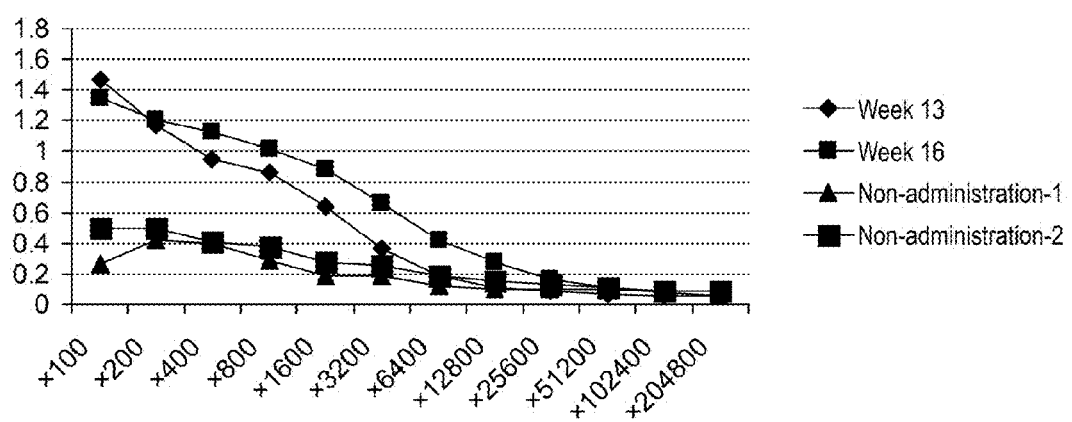
Figures 4, 11:
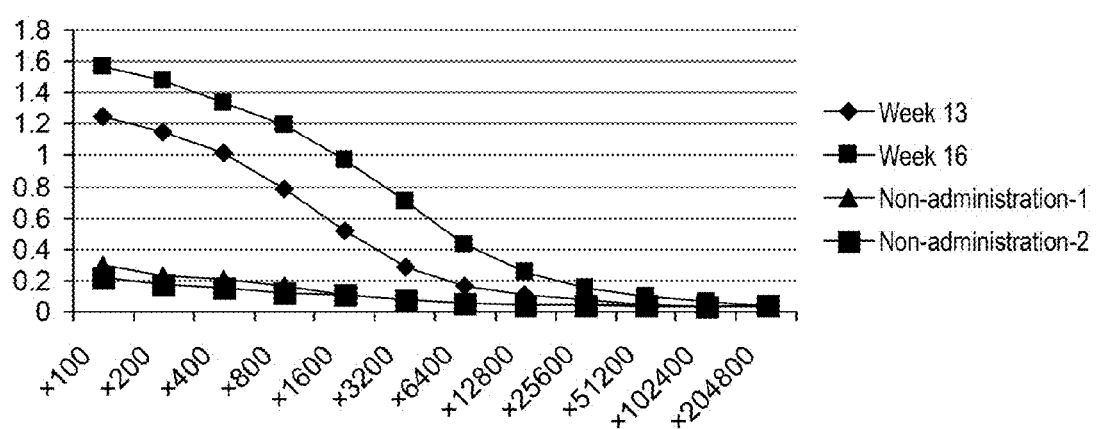
Figures 5, 11:
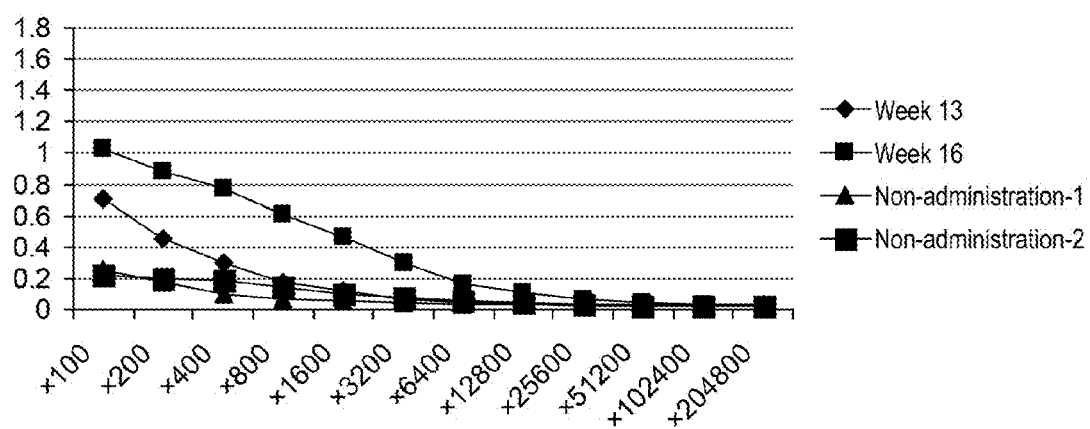

FIG. 11-1 shows the results about dog IgE. FIG. 11-2 shows the results about dog IgG. FIG. 11-3 shows the results about mouse IgE. FIG. 11-4 shows the results about human IgE. FIG. 11-5 shows the results about cat CH3.

Dog IgG used as the immobilized antigen responded to neither of the peptide-administered rabbit serum nor the peptide-non-administered rabbit serum. Dog IgE, human IgE, mouse IgE, or cat IgE used as the immobilized antigen responded to the peptide-administered rabbit serum, but did not respond to the peptide-non-administered rabbit serum.

The results of this Example demonstrated that the peptide of the present invention is useful as a peptide vaccine against a wide range of animal species.

Example 5 Study on Vaccine Effects of Various Peptides

The tests up to Example 4 implied that the peptide sequence (QEKKTSVSASQWYTKHHNNATTSIT: SEQ ID NO: 27, M 4-17-11) was important.

For the purpose of further narrowing the scope of the sequence, the following peptides were synthesized: 20 types of peptides derived from the peptide by the truncation of 10 N-terminal or C-terminal residues. Rats were immunized with these 20 types of peptides and evaluated for antibody response to dog IgE.

Synthesized peptides (number in the first parentheses represents peptide number):

(1)
(SEQ ID NO: 29)
QEKKTSVSASQWYTKHHNNATTSI (2)
(SEQ ID NO: 31)
QEKKTSVSASQWYTKHHNNATTS (3)
(SEQ ID NO: 34)
QEKKTSVSASQWYTKHHNNATT (4)
(SEQ ID NO: 38)
QEKKTSVSASQWYTKHHNNAT (5)
(SEQ ID NO: 43)
QEKKTSVSASQWYTKHHNNA (6)
(SEQ ID NO: 49)
QEKKTSVSASQWYTKHHNN (7)
(SEQ ID NO: 56)
QEKKTSVSASQWYTKHHN (8)
(SEQ ID NO: 64)
QEKKTSVSASQWYTKHH (9)
(SEQ ID NO: 72)
QEKKTSVSASQWYTKH

(10)
(SEQ ID NO: 82)
QEKKTSVSASQWYTK

(11)
(SEQ ID NO: 30)
EKKTSVSASQWYTKHHNNATTSIT

(12)
(SEQ ID NO: 33)
KKTSVSASQWYTKHHNNATTSIT

(13)
(SEQ ID NO: 37)
KTSVSASQWYTKHHNNATTSIT

(14)
(SEQ ID NO: 42)
TSVSASQWYTKHHNNATTSIT

(15)
(SEQ ID NO: 48)
SVSASQWYTKHHNNATTSIT

(16)
(SEQ ID NO: 55)
VSASQWYTKHHNNATTSIT

(17)
(SEQ ID NO: 63)
SASQWYTKHHNNATTSIT

(18)
(SEQ ID NO: 71)
ASQWYTKHHNNATTSIT

(19)
(SEQ ID NO: 81)
SQWYTKHHNNATTSIT

(20)
(SEQ ID NO: 92)
QWYTKHHNNATTSIT

Animal Under Test:

Forty rats (Wistar-ST/7w/female) were used and divided into 20 groups each involving 2 individuals.

Immunization:

200 μg (500 μg/mL) of each synthesized peptide (KLH-conjugated) was mixed with an equal amount of a complete adjuvant, and this mixture was subcutaneously administered twice at a 2-week interval to each rat.

Evaluation Method:

Two weeks after the second immunization, serum was collected, and an IgG antibody against dog IgE was evaluated by ELISA.

The Protocol of ELISA was as Follows:

The dog IgE protein (Bethyl Laboratories, Inc.; P115), the mouse IgE protein (BD Biosciences, San Jose, Calif., USA), and the human IgE protein (Athens Research And Technology, Inc.; 16-16-090705-ML) were each prepared at 1 μg/mL, 500 ng/mL, 250 ng/mL, 125 ng/mL, 62.5 ng/mL, 31.2 ng/mL, 15.6 ng/mL, 7.8 ng/mL, 3.9 ng/mL, 1.95 ng/mL, and 0.97 ng/mL in an immobilization buffer (0.05 M carbonate buffer, pH 9.6), then added at a concentration of 100 μL/well to an ELISA plate, and left overnight at 4° C. The immobilization plate was washed once with PBS-T (0.05%). A blocking solution (4× Block Ace, Snow Brand Milk Products Co., Ltd.; UK-B80) was added thereto at a concentration of 200 μL/well. The plate was blocked by incubation at 37° C. for 1.5 hours. The serum was diluted 2000-fold with a diluent (PBS-T:Block Ace=9:1) and used. The serum of an unimmunized rat was similarly diluted and used as a negative control. The plate was reacted with the serum at 37° C. for 1.5 hours and washed three times with PBS-T (0.05%). A HRP-labeled anti-rat IgG antibody (Invitrogen Corp., 619520) was diluted 2000-fold with a diluent and added thereto as a secondary antibody at a concentration of 100 μL/well. After reaction at 37° C. for 1.5 hours, the plate was washed three times with PBS-T (0.05%). A substrate solution (citrate buffer supplemented with one TMBZ tablet (Sigma-Aldrich Corp.; T-3405) and further supplemented, immediately before use, with 2 μL of 30% $H_2O_2$) was added at a concentration of 100 μL/well to the plate and reacted therewith for 10 minutes. The reaction was terminated by the addition of 2 N sulfuric acid at a concentration of 50 μL/well. Then, the measurement was performed using a plate reader (Bio-Rad Laboratories, Inc.; model 680) (dual: measurement: 450 nm, control: 570 nm).

Figures 3, 12:
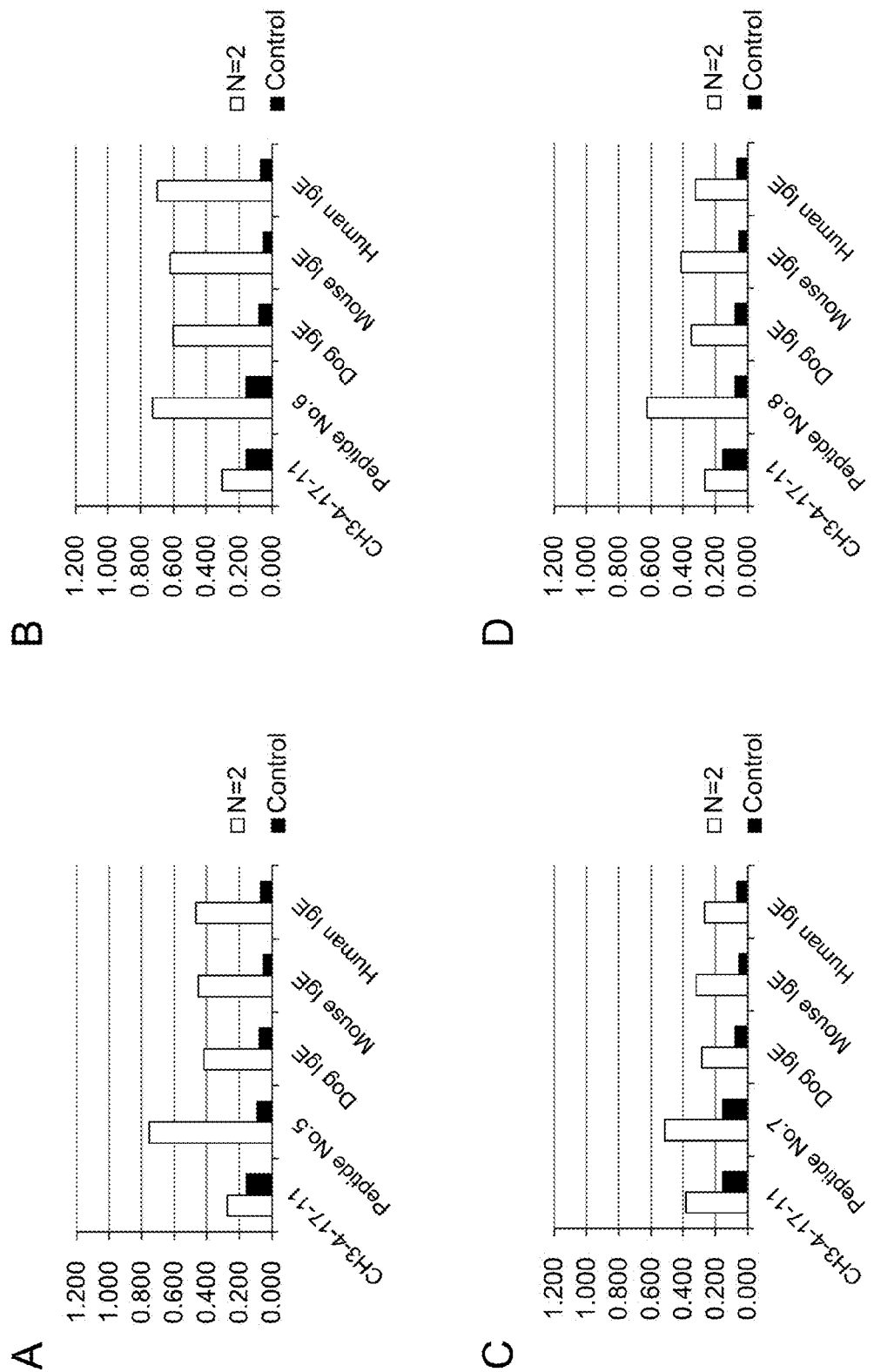
Figures 4, 12:
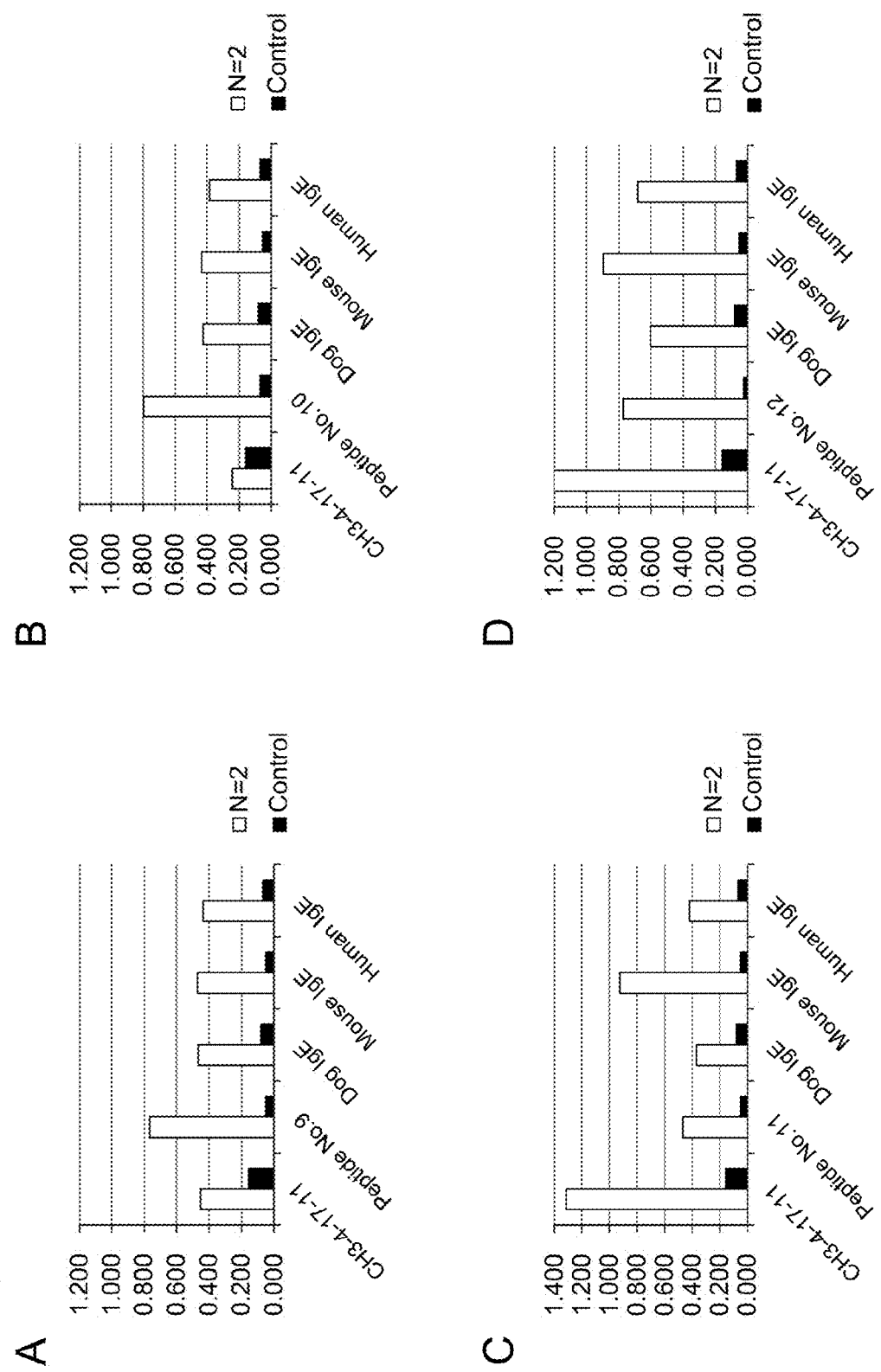
Figures 5, 12:
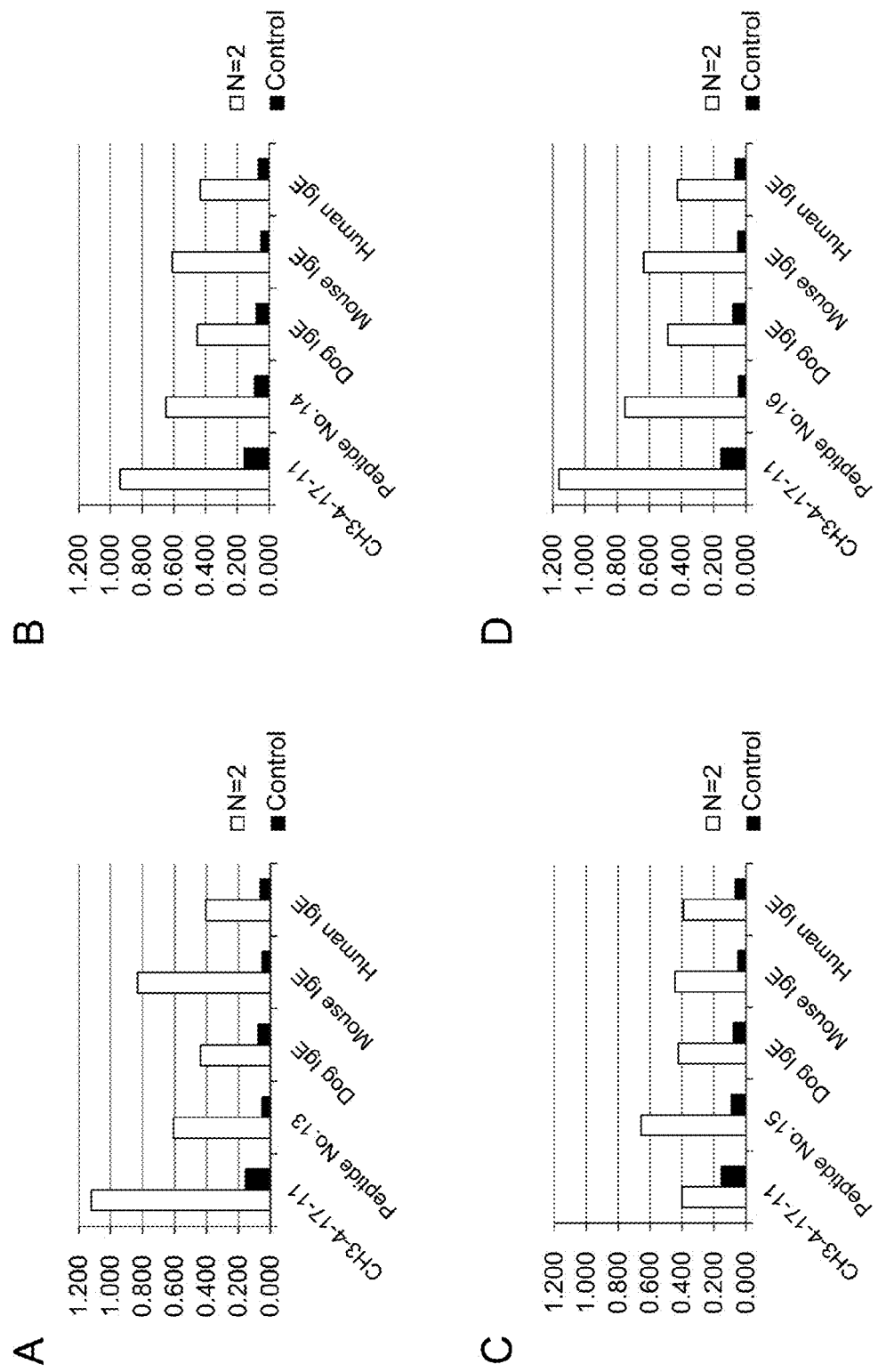
Figures 6, 12:
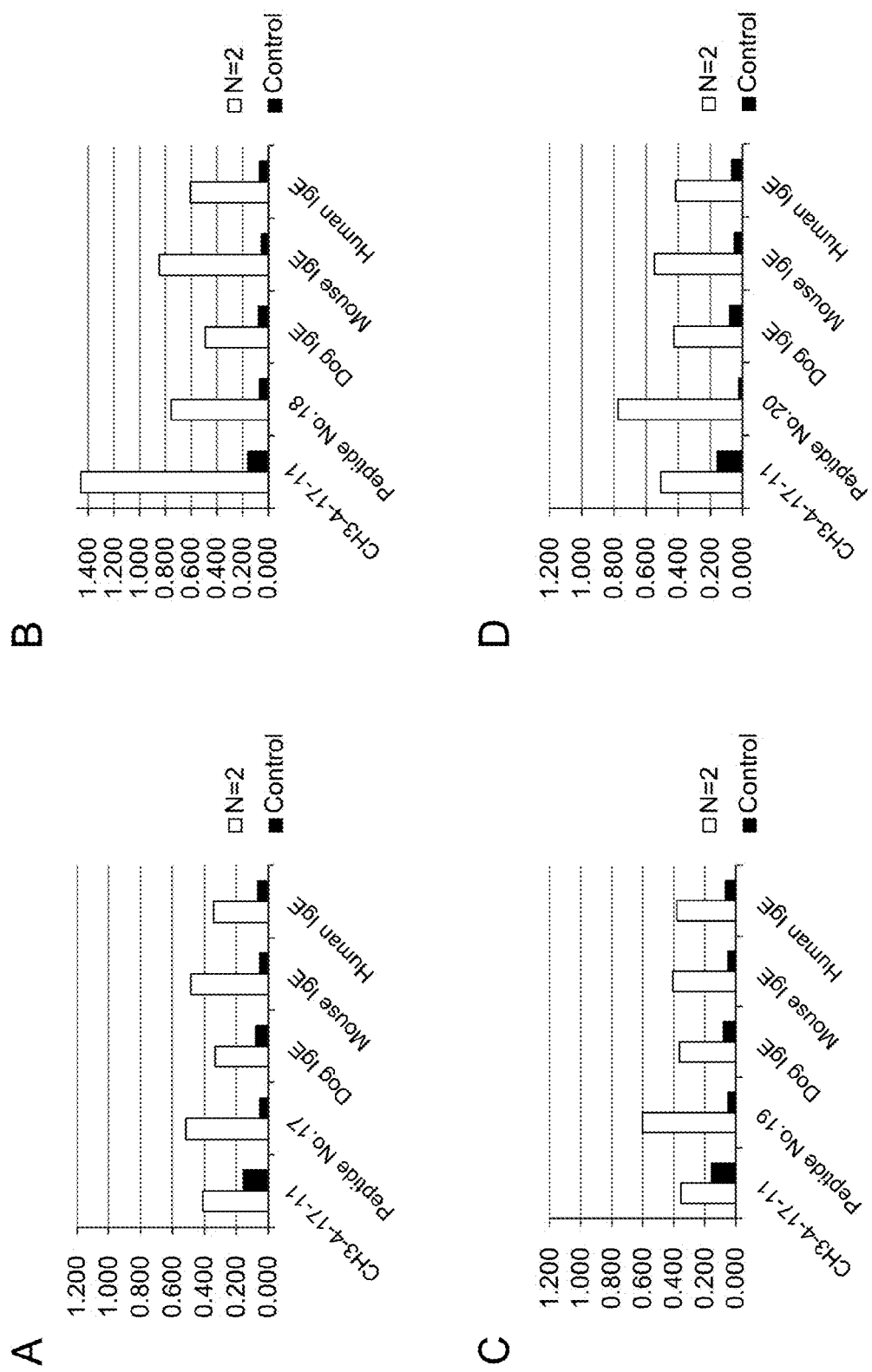

Results:

The results are shown in FIG. 12-1. FIG. 12-1A shows the results about peptide Nos. 1 to 10 among the 20 types of peptides. FIG. 12-1B shows the results about peptide Nos. 11 to 20. The sequences of the peptides used are shown below the graphs of FIGS. 12-1A and 12-1B. The ordinates of the graphs of FIGS. 12-1A and 12-1B represent OD values, and the abscissas thereof represent the amount of dog IgE immobilized. FIGS. 12-2 to 12-6 show the reactivity of 100-fold diluted serum of rats immunized with each peptide (peptide of SEQ ID NO: 27, immunization peptide itself, dog IgE, mouse IgE, and human IgE). FIG. 12-2 shows the results about peptide Nos. 1 to 4 (in the diagram, A to D, respectively). FIG. 12-3 shows the results about peptide Nos. 5 to 8 (in the diagram, A to D, respectively). FIG. 12-4 shows the results about peptide Nos. 9 to 12 (in the diagram, A to D, respectively). FIG. 12-5 shows the results about peptide Nos. 13 to 16 (in the diagram, A to D, respectively). FIG. 12-6 shows the results about peptide Nos. 17 to 20 (in the diagram, A to D, respectively). The immunization with any of these peptides at a high concentration (100-fold dilution) was confirmed to induce the production of an IgG antibody against IgE in serum. In FIGS. 12-2 to 12-6, the CH3-4-17-11 peptide is a peptide consisting of the amino acid sequence represented by SEQ ID NO: 27.

As shown in FIGS. 12-1 to 12-6, the N-terminal truncation weakened antibody response to dog IgE, suggesting that the N-terminal region contains a presumably important sequence.

Example 6 Intravenous Administration Test Using Rat

In light of the results of Example 5, a peptide of 20 residues was synthesized by the truncation of 2 N-terminal residues and 3 C-terminal residues from the peptide of SEQ ID NO: 27 (QEKKTSVSASQWYTKHHNNATTSIT).

The newly synthesized peptide sequence (peptide name: M4-7-11) was KKTSVSASQWYTKHHNNATT (SEQ ID NO: 45).

This peptide was used in the immunization of rats without the use of an adjuvant, and antibody response to dog IgE was evaluated.

Figure 13:
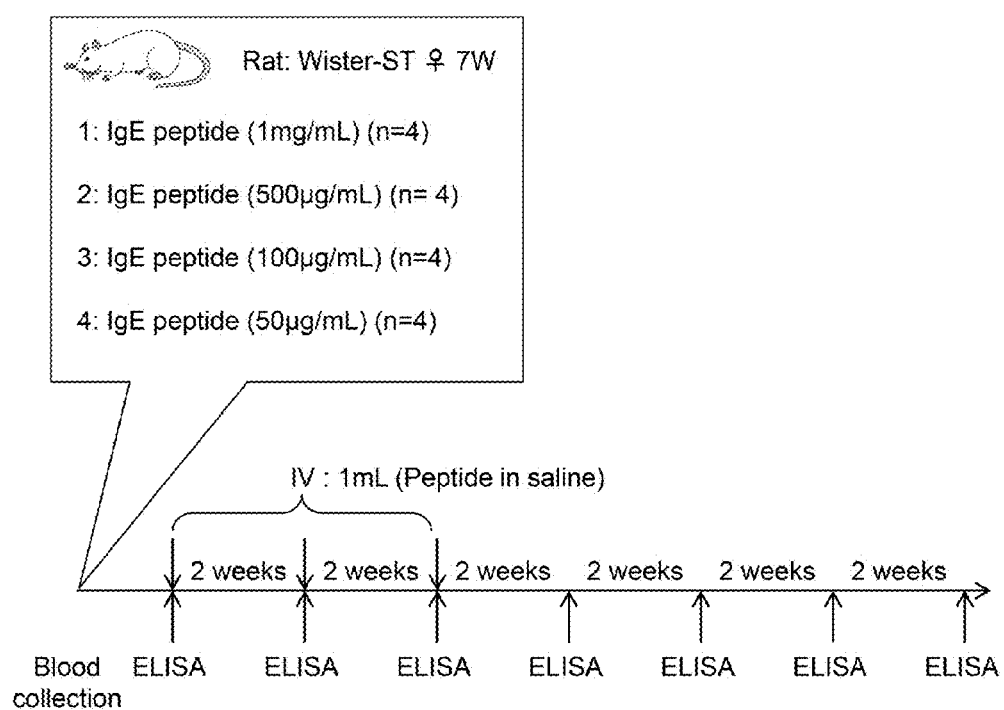
FIG. 13 is a diagram showing the protocol of an intravenous administration test using rats.

Animal Under Test:

Twenty rats (Wistar-ST/7w/female) were used and divided into 4 groups each involving 4 individuals (FIG. 13).

Immunization:

The peptide M4-7-11 (KKTSVSASQWYTKHHNNATT) (SEQ ID NO: 45) (not conjugated with KLH) was concentration-adjusted to 1 mg/mL, 500 µg/mL, 100 µg/mL, and 50 µg/mL with saline and intravenously administered at a dose of 1 mL/animal three times at 2-week intervals.

Evaluation Method:

Blood was collected every 2 weeks from the administer start date up to 8 weeks after the third immunization. Serum was collected, and an IgG antibody against dog IgE was evaluated by ELISA (FIG. 13).

ELISA used in the assay of IgG against dog IgE was performed in the same way as in Example 6.

IgE against the house dust mite allergen Der f 2 was assayed by the following method:

Der f 2 was prepared at 1 µg/mL in an immobilization buffer (0.05 M carbonate buffer, pH 9.6), then added at a concentration of 100 µL/well to an ELISA plate, and left overnight at 4° C. The immobilization plate was washed once with PBS-T (0.05%). A blocking solution (4× Block Ace, Snow Brand Milk Products Co., Ltd.; UK-B80) was added thereto at a concentration of 200 µL/well. The plate was blocked by incubation at 37° C. for 1.5 hours. The serum was diluted 20-fold with a diluent (PBS-T:Block Ace=9:1) and used. The plate was reacted with the serum at 37° C. for 1.5 hours and washed three times with PBS-T (0.05%). An anti-rat IgE antibody (Rabbit anti-Rat IgE HRP; Invitrogen Corp., 61-9520) was diluted 1000-fold with a diluent and added thereto as a secondary antibody at a concentration of 100 µL/well. After reaction at 37° C. for 1.5 hours, the plate was washed three times with PBS-T (0.05%). A substrate solution (citrate buffer supplemented with one TMBZ tablet (Sigma-Aldrich Corp.; T-3405) and further supplemented, immediately before use, with 2 µL of 30% $H_2O_2$) was added at a concentration of 100 µL/well to the plate and reacted therewith for 10 minutes. The reaction was terminated by the addition of 2 N sulfuric acid at a concentration of 50 µL/well. Then, the measurement was performed using a plate reader (Bio-Rad Laboratories, Inc.; model 680) (dual: measurement: 450 nm, control: 570 nm).

Results:

The results are shown in FIG. 14. FIG. 14A shows a time-dependent rise in the level of a rat IgG antibody. In FIG. 14B, the pictures of syringes represent that the peptide was administered at this point in time. FIG. 14B shows IgE antibody titers. As shown in FIG. 14, a rise in the level of the IgG antibody against dog IgE was confirmed in all of the groups.

FIG. 14B shows anti-dog IgE IgG antibody titers in rat serum at the final day (8 weeks after the third vaccination day). The antibody titer was increased to 3000 times in all of the groups.

Example 7 Subcutaneous Administration Test Using Rat

A subcutaneous administration test was set in order to confirm that the rise in the level of an anti-dog IgE antibody in Example 6 was brought about by 3 shots of 50 µg and to confirm whether or not the antibody titer would elevate by subcutaneous administration, which is easy to achieve compared with the intravenous administration.

The peptide sequence (peptide name: M4-7-11) used in immunization was KKTSVSASQWYTKHHNNATT (SEQ ID NO: 45).

This peptide was used in the immunization of rats without the use of an adjuvant, and antibody response to dog IgE was evaluated.

Figure 15:
FIG. 15 is a diagram showing the protocol of a subcutaneous administration test using rats.

Animal Under Test:

Twelve rats (Wistar-ST/7w/female) were used and divided into 3 groups each involving 4 individuals (FIG. 15).

Figure 16:
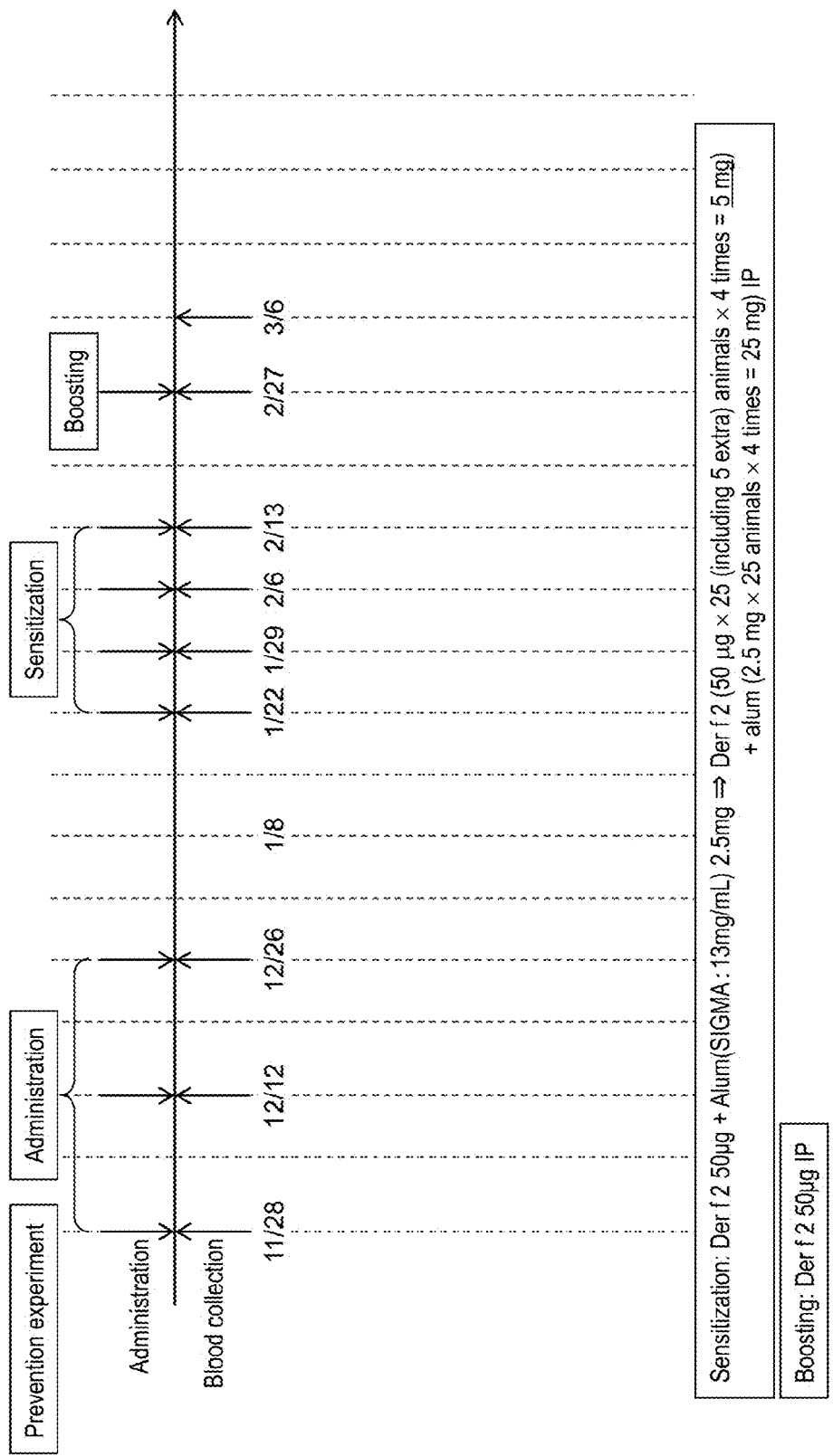
FIG. 16 is a diagram showing the protocol of a prevention experiment.

In this Example, a prevention experiment was conducted. The prevention experiment refers to a method which involves performing vaccination, then increasing IgE levels by immunization with a house dust mite antigen (Der f 2) together with an alum adjuvant, and evaluating the inhibition of this increase in IgE level (FIG. 16).

Immunization:

The peptide M4-7-11 (KKTSVSASQWYTKHHNNATT) (SEQ ID NO: 45) (not conjugated with KLH) was concentration-adjusted to 50 µg/mL with saline and intravenously and subcutaneously administered at a dose of 1 mL/animal three times at 2-week intervals.

Evaluation Method:

Blood was collected every 2 weeks from the administer start date. The house dust mite antigen (Der f 2: 50 µg) was intraperitoneally administered together with an alum adjuvant (2.5 mg; Sigma-Aldrich Corp.) four times at 1-week intervals for 4 weeks after the third immunization. Two weeks after the fourth sensitization, 50 µg of Der f 2 was intraperitoneally administered alone. Blood was collected up to. Serum was collected, and an IgG antibody against dog IgE was evaluated by ELISA (FIG. 16). ELISA was performed in the same way as in Example 5.

Results:

FIG. 17 shows the results of confirming a rise in the level of a rat IgG antibody against dog IgE. FIG. 17A shows a time-dependent rise in the level of the rat IgG antibody. In FIG. 17A, the pictures of syringes represent that the peptide was administered at this point in time. FIG. 17B shows IgE antibody titers. As shown in FIG. 17, the level of the rat IgG antibody against dog IgE was confirmed to elevate by the intravenous and subcutaneous administration of the peptide vaccine (M4-7-11).

Figure 18:
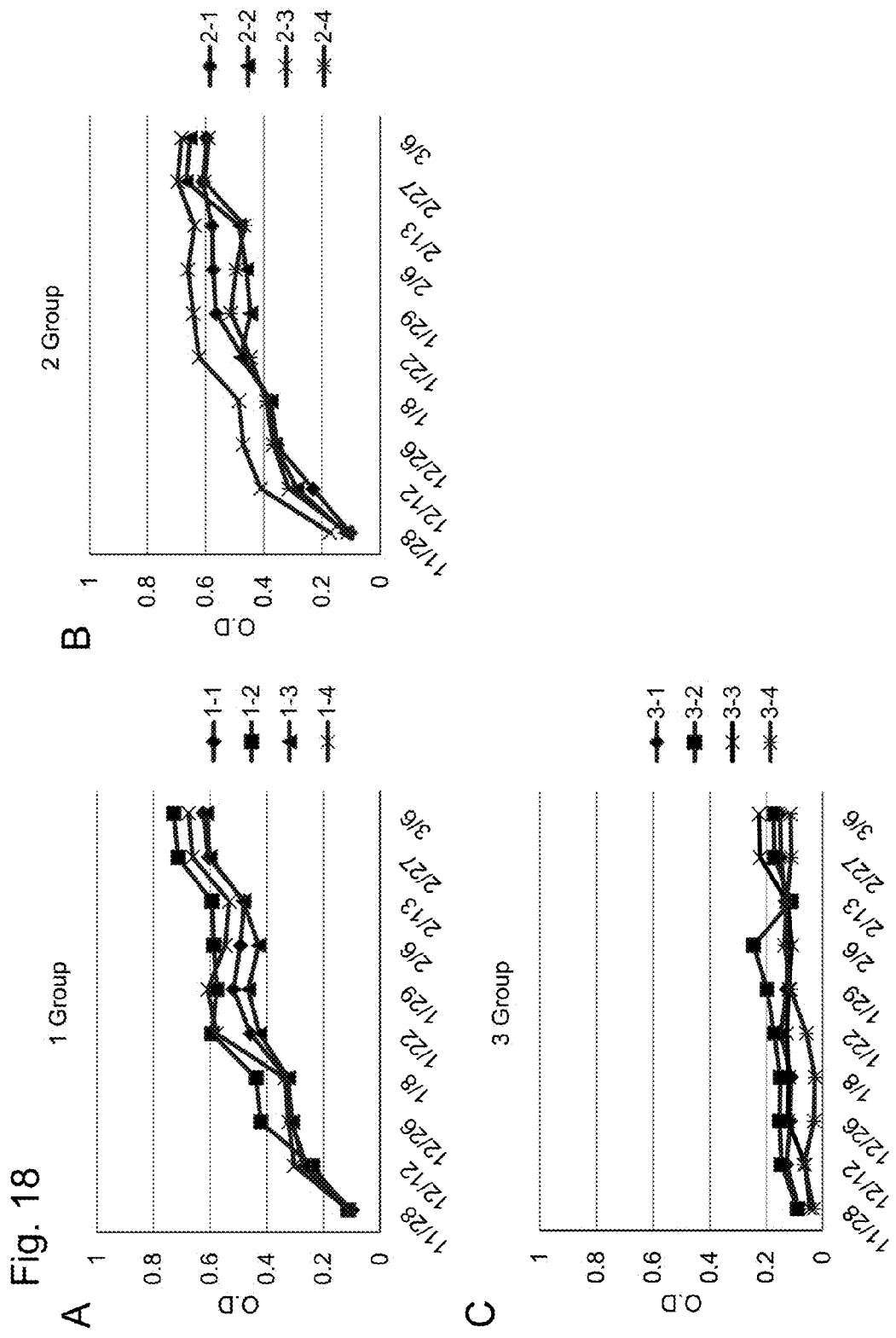
FIG. 18 is a diagram showing a rise in anti-IgE antibody titer per individual when a peptide is subcutaneously administered to rats.

FIG. 18 shows data on an individual basis in each group. FIGS. 18A, 18B, and 18C show the results about groups 1, 2, and 3, respectively.

Figure 19:
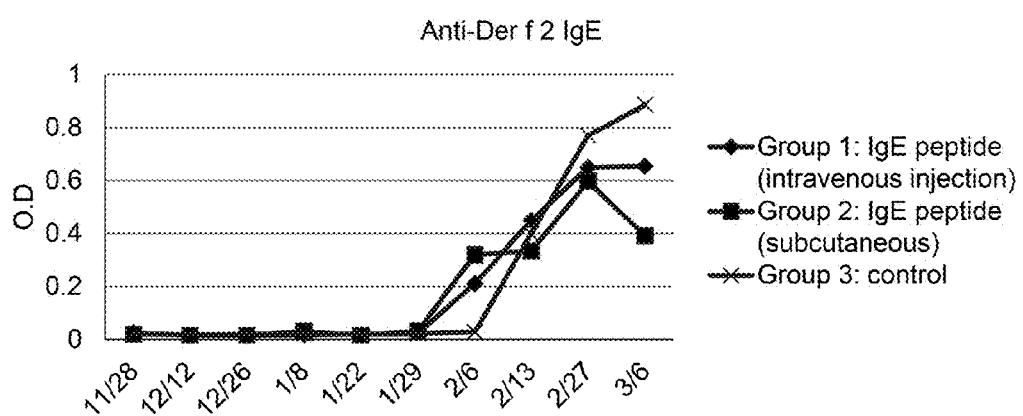
FIG. 19 is a diagram showing results of assaying Der f 2-specific IgE when a peptide is subcutaneously administered to rats.

FIG. 19 shows the results (average of each group) of assaying Der f 2-specific IgE.

Figure 20:
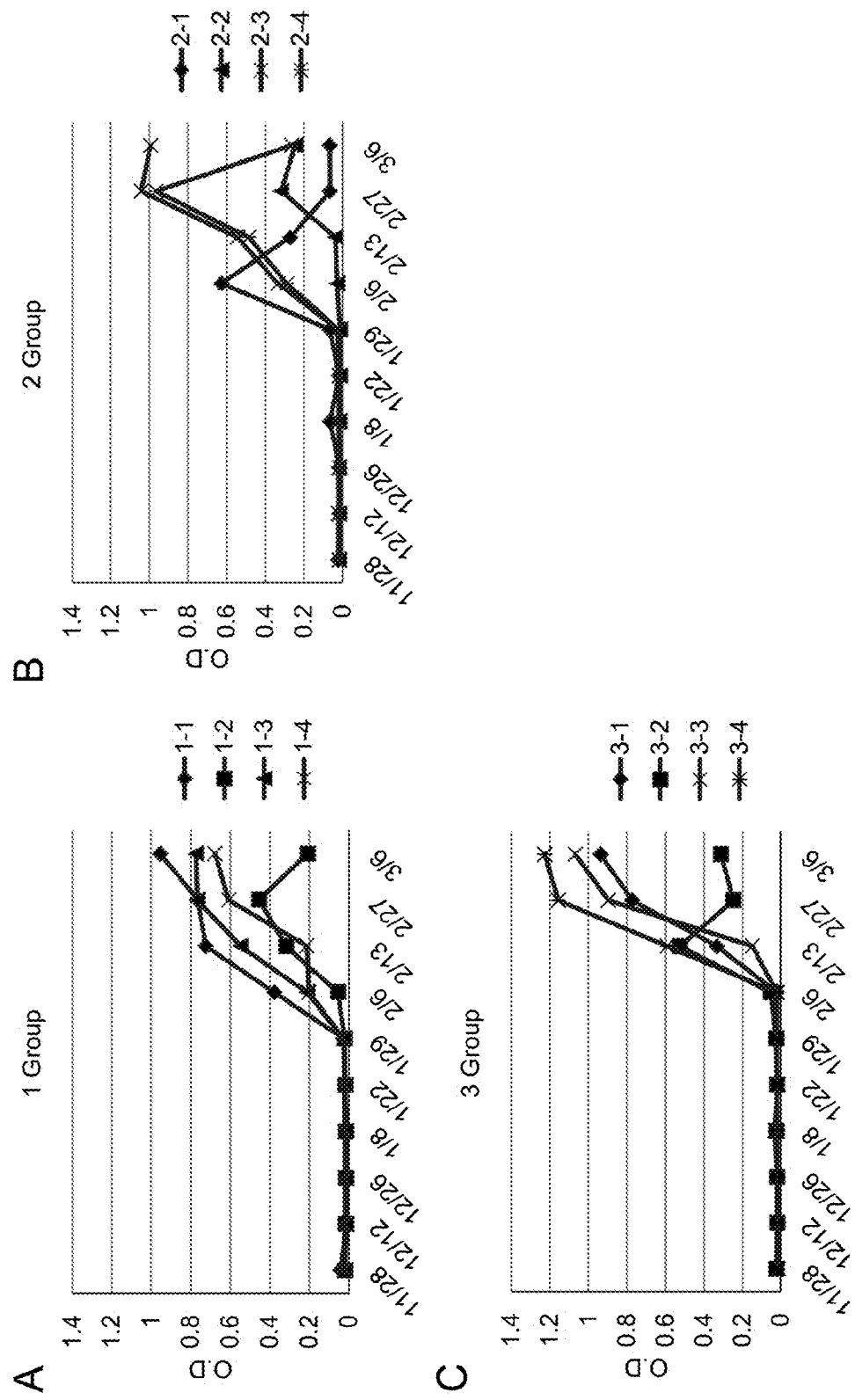
FIG. 20 is a diagram showing results of assaying Der f 2-specific IgE per individual when a peptide is subcutaneously administered to rats.

FIG. 20 shows the results on an individual basis. FIGS. 20A, 20B, and 20C show the results about groups 1, 2, and 3, respectively. As shown in FIGS. 19 and 20, the inhibition of IgE production was confirmed in the groups intravenously or subcutaneously given the peptide vaccine (M4-7-11) compared with the control group (saline). The inhibition of IgE production was remarkably confirmed in the subcutaneous administration group (group 2).

Example 8 Test Using Dog (Part 1)

Since a rise in the level of the IgG antibody against dog IgE was confirmed by the subcutaneous administration test using rats, a test was carried out using dogs.

The peptide (M4-7-11) was concentration-adjusted to 2 mg/mL with saline, dispensed in an amount of 500 μL, and used as a vaccine. The peptide had a purity of 98.1%, and its synthesis was consigned to Hokkaido System Science Co., Ltd. The vaccine was confirmed to be not contaminated with endotoxin. The vaccine administration method was subcutaneous administration of 1 mg per dose, which was performed five times at 2-week intervals. Another purpose of this test was to study the frequency of administration of the vaccine.

Testing Method:

Dog: 4 healthy beagles (8 months old; 2 males and 2 females) were used.

Vaccine: the M4-7-11 peptide was used alone without being conjugated.

Administration method: 1 mg (500 μl, of 2 mg/mL) per dose was subcutaneously administered five times at 2-week intervals.

Evaluation: serum was collected approximately once per week, and an IgG antibody against human IgE was assayed by ELISA. Since dog IgE nonspecifically reacts with an anti-dog IgG antibody, human IgE having no nonspecific reaction was used in ELISA.

Figure 21:
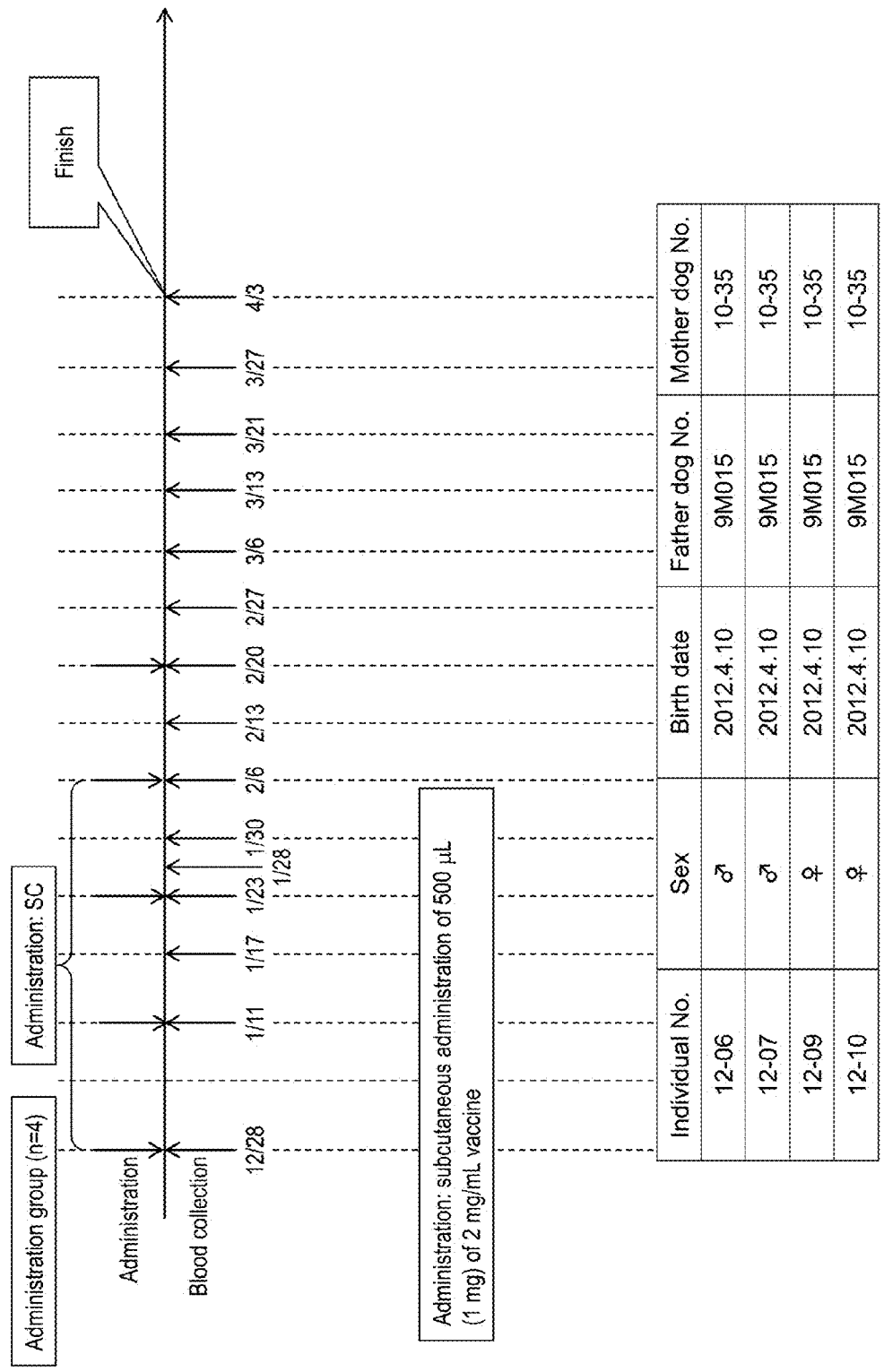
FIG. 21 is a diagram showing the protocol of a peptide administration test (Part 1) using dogs.

The test schedule is shown in FIG. 21.

The ELISA method was as follows:

Human IgE (Athens Research And Technology, Inc.; IgE, human Myeloma Plasma) was prepared at 1 μg/mL in an immobilization buffer (0.05 M carbonate buffer, pH 9.6), then added at a concentration of 100 μL/well to an ELISA plate, and left overnight at 4° C. The immobilization plate was washed once with PBS-T (0.05%). A blocking solution (4× Block Ace, Snow Brand Milk Products Co., Ltd.; UK-B80) was added thereto at a concentration of 200 μL/well. The plate was blocked by incubation at 37° C. for 1.5 hours. The serum was diluted 1000-fold with a diluent (PBS-T:Block Ace=9:1) and used. The plate was reacted with the serum at 37° C. for 1.5 hours and washed three times with PBS-T (0.05%). An anti-dog IgG antibody (Sheep anti-Dog IgG HRP, Bethyl Laboratories, Inc.; A40-118P) was diluted 2000-fold with a diluent and added thereto as a secondary antibody at a concentration of 100 μL/well. After reaction at 37° C. for 1.5 hours, the plate was washed three times with PBS-T (0.05%). A substrate solution (citrate buffer supplemented with one TMBZ tablet (Sigma-Aldrich Corp.; T-3405) and further supplemented, immediately before use, with 2 μL of 30% $H_2O_2$) was added at a concentration of 100 μL/well to the plate and reacted therewith for 10 minutes. The reaction was terminated by the addition of 2 N sulfuric acid at a concentration of 50 μL/well. Then, the measurement was performed using a plate reader (Bio-Rad Laboratories, Inc.; model 680) (dual: measurement: 450 nm, control: 570 nm).

In this context, if dog IgE is used as an immobilized antibody for the ELISA measurement of IgE-specific IgG concentrations, the dog IgG-specific polyclonal antibody used as a secondary antibody may bind to the immobilized antibody to cause nonspecific reaction. For this reason, human IgE was used as the immobilized antibody.

Figure 22:
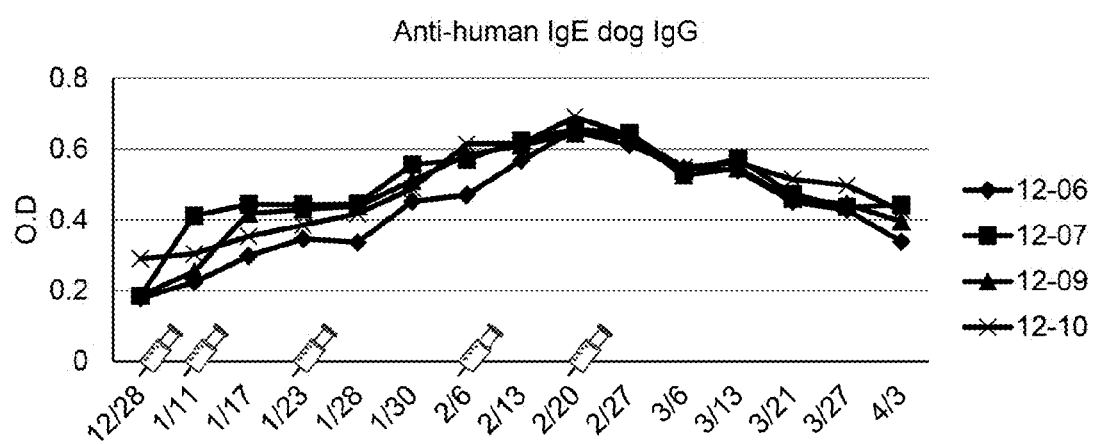
FIG. 22 is a diagram showing a rise in anti-IgE antibody titer when a peptide was subcutaneously administered to dogs.

Results:

FIG. 22 shows the results of evaluating the production of an IgG antibody against IgE by ELISA when the peptide vaccine (M4-7-11) was subcutaneously administered to dogs. In FIG. 22, the pictures of syringes represent that the peptide was administered at this point in time. As shown in FIG. 22, the level of the IgG antibody against IgE was confirmed to elevate in the dogs by the administration of the vaccine. The results of FIG. 22 also suggested that 4 or less shots suffice for the frequency of administration.

Example 9 Test Using Dog (Part 2)

In Example 8, the vaccine (M4-11-17) was administered to 4 dogs to confirm a rise in the level of the IgG antibody against IgE. In order to confirm reproducibility, a test was carried out using 8 dogs including a control group (saline). The dogs used in this test were 2-year-old or older adult dogs.

The testing method was as follows:

Dog: 8 healthy beagles (24 months old; 4 males and 4 females) were used.

Vaccine: the M4-7-11 peptide was used alone without being conjugated.

Administration method: 1 mg (500 μL of 2 mg/mL) per dose was subcutaneously administered five times at 2-week intervals.

Figure 23:
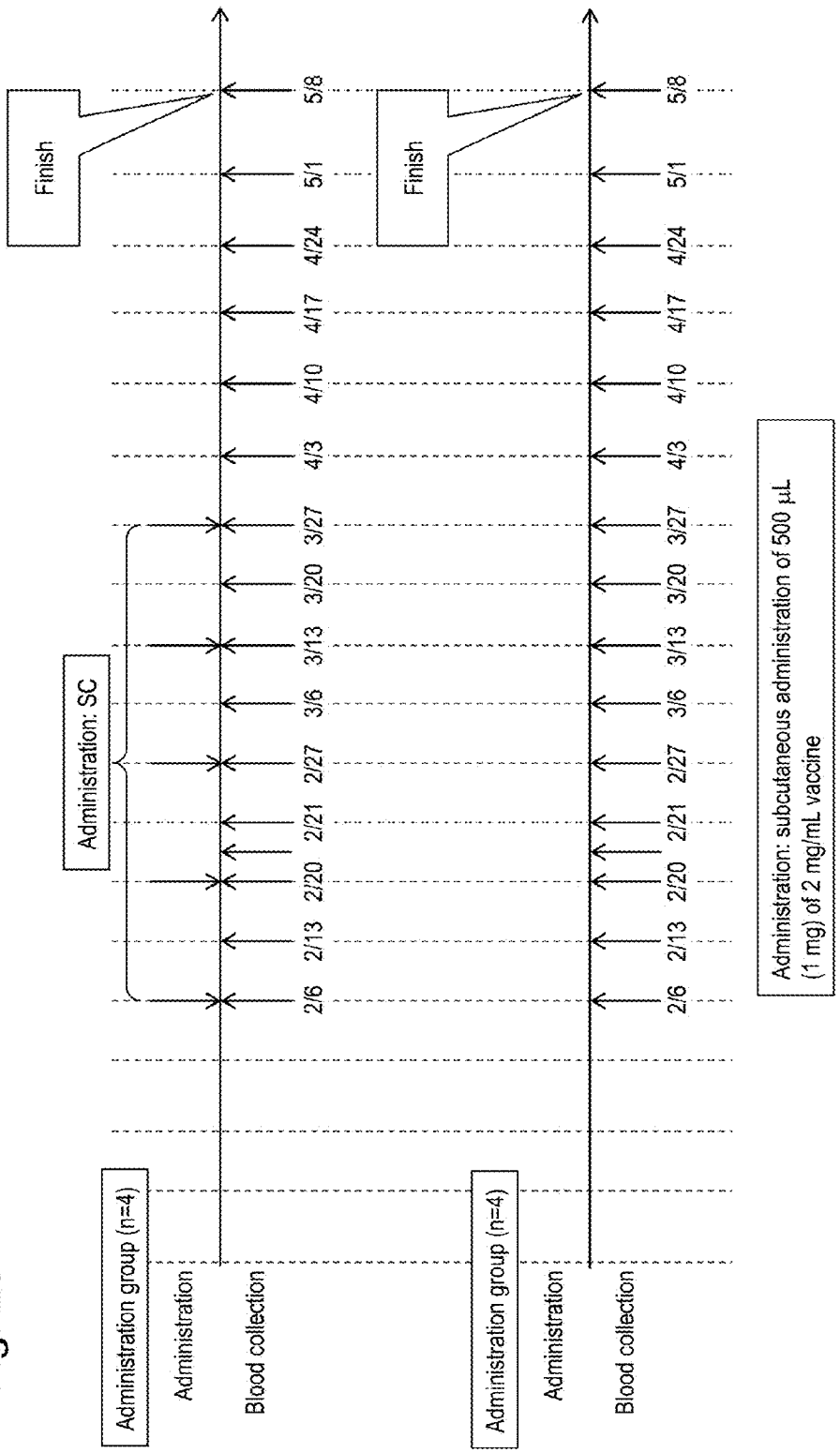
FIG. 23 is a diagram showing the protocol of a peptide administration test (Part 2) using dogs.

Evaluation: serum was collected approximately once per week, and an IgG antibody against human IgE was assayed by ELISA. Since dog IgE nonspecifically reacts with an anti-dog IgG antibody, human IgE having no nonspecific reaction was used in ELISA. The test schedule is shown in FIG. 23. ELISA was performed in the same way as in Example 8.

Results:

FIG. 24 shows the results of evaluating the production of an IgG antibody against IgE by ELISA when the peptide vaccine (M4-7-11) was subcutaneously administered to dogs. FIG. 24A shows the average antibody titers of the peptide vaccine administration group and the control group. FIG. 24B and FIG. 24C show the antibody titer of each individual in the vaccine administration group and the control group (non-administration group), respectively.

As shown in FIG. 24, the level of the IgG antibody against IgE was confirmed to elevate in the dogs by the administration of the vaccine. This elevated level was also confirmed in adult dogs as in Example 8. In addition, 4 or less shots were confirmed again to suffice for the frequency of administration.

Example 10 Treatment Experiment Using Artificially Sensitized Dog

In Examples 8 and 9, the production of an IgG antibody against IgE by the subcutaneous administration of the peptide vaccine (M4-7-11) was confirmed using healthy dogs.

Thus, a treatment experiment was conducted using dogs artificially sensitized with *Dermatophagoides farinae*.

The testing method was as follows:

Testing method:

Dog: 8 artificially sensitized beagles (1 to 8 years old; 4 males and 4 females) were used. The ages and numbers of these 8 dogs were as follows:

8 years old: 04-78 (administration group), 04-95 (administration group), and 04-60 (control group)

5 years old: 08-64 (administration group)

4 years old: 09-63 (control group)

2 years old: 10-70 (control group)

1 year old: 11-12 (administration group) and 11-40 (control group)

Artificial sensitization: 400 μg of a *Dermatophagoides farinae* antigen (GREER) and 1 mg of an alum adjuvant (LSL) were subcutaneously administered at a 2-week interval, and IgE against the *Dermatophagoides farinae* antigen was confirmed by ELISA.

Grouping: on the basis of the ELISA results of IgE, the dogs were divided into 2 groups each involving 4 individuals uniformly distributed in terms of their IgE levels and ages.

Vaccine: the M4-7-11 peptide was used alone without being conjugated.

Administration method: 1 mg (500 μL of 2 mg/mL) per dose was subcutaneously administered five times at 2-week intervals.

Evaluation: serum was collected, and an IgG antibody against human IgE was assayed by ELISA. Since dog IgE nonspecifically reacts with an anti-dog IgG antibody, human IgE having no nonspecific reaction was used in ELISA. The IgE antibody against *Dermatophagoides farinae* was evaluated by ELISA.

Figure 25:
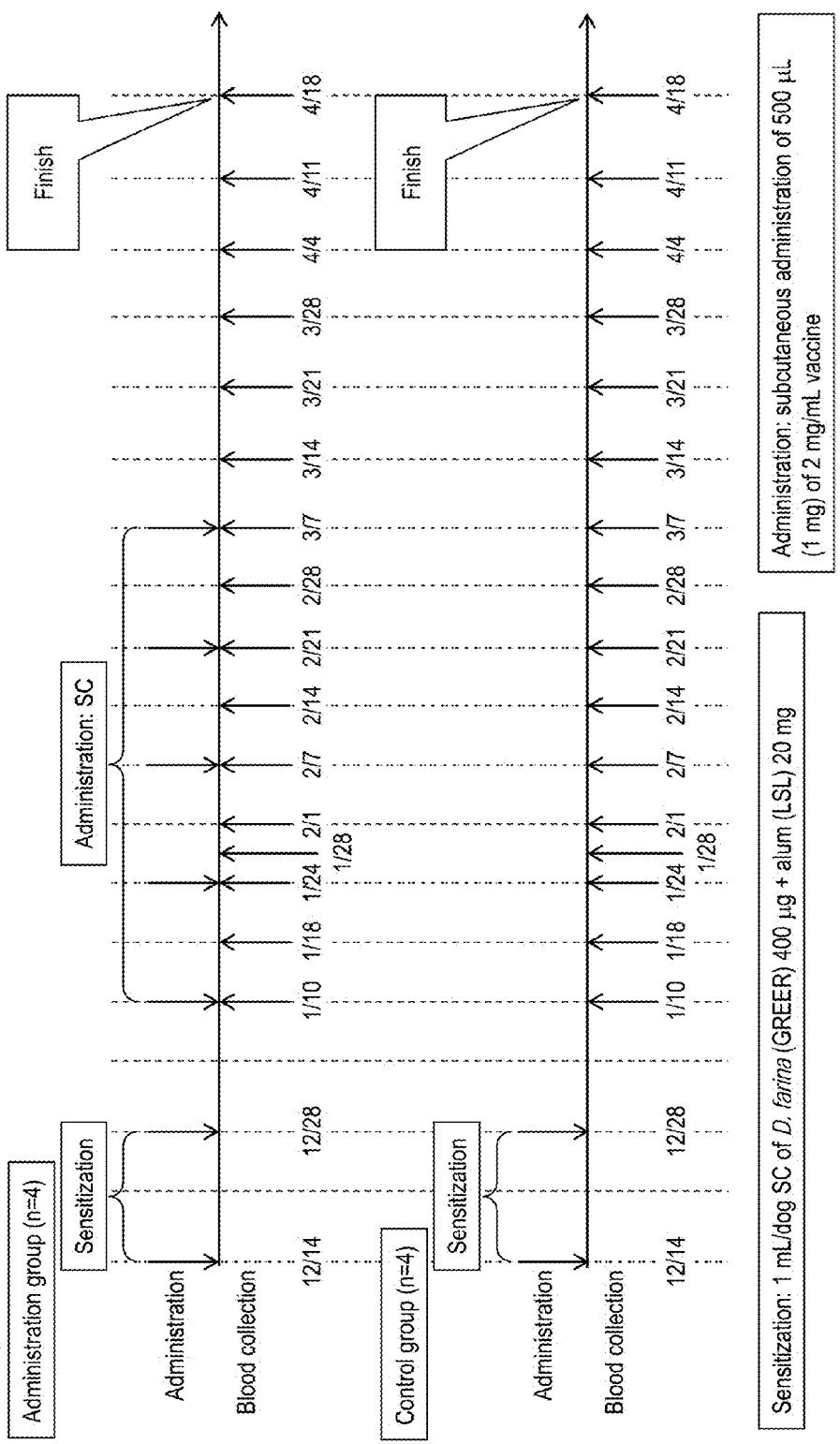
FIG. 25 is a diagram showing the protocol of a treatment experiment using dogs artificially sensitized with *Dermatophagoides farinae*.

The test schedule is shown in FIG. 25.

The ELISA methods were performed as mentioned below.

The method for assaying IgG against IgE was performed in the same way as in Examples 8 and 9.

The method for assaying dog IgE against the *Dermatophagoides farinae* antigen was as follows:

The *Dermatophagoides farinae* antigen was prepared at 5 μg/mL in an immobilization buffer (0.05 M carbonate buffer, pH 9.6), then added at a concentration of 100 μL/well to an ELISA plate, and left overnight at 4° C. The immobilization plate was washed once with PBS-T (0.05%). A blocking solution (4× Block Ace, Snow Brand Milk Products Co., Ltd.; UK-B80) was added thereto at a concentration of 200 μL/well. The plate was blocked by incubation at 37° C. for 1.5 hours. The serum was diluted 20-fold with a diluent (PBS-T:Block Ace=9:1) and used. The plate was reacted with the serum at 37° C. for 1.5 hours and washed three times with PBS-T (0.05%). An anti-dog IgE antibody (Goat anti-Dog IgE HRP, Bethyl Laboratories, Inc.; A40-125P) was diluted 2000-fold with a diluent and added thereto as a secondary antibody at a concentration of 100 μL/well. After reaction at 37° C. for 1.5 hours, the plate was washed three times with PBS-T (0.05%). A substrate solution (citrate buffer supplemented with one TMBZ tablet (Sigma-Aldrich Corp.; T-3405) and further supplemented, immediately before use, with 2 μL of 30% $H_2O_2$) was added at a concentration of 100 μL/well to the plate and reacted therewith for 10 minutes. The reaction was terminated by the addition of 2 N sulfuric acid at a concentration of 50 μL/well. Then, the measurement was performed using a plate reader (Bio-Rad Laboratories, Inc.; model 680) (dual: measurement: 450 nm, control: 570 nm).

Results:

FIG. 26 shows the results of evaluating the production of an IgG antibody against IgE by ELISA when the peptide vaccine (M4-7-11) was subcutaneously administered to dogs. FIG. 26A shows the average antibody titers of the peptide vaccine administration group and the control group. FIG. 26B and FIG. 26C show the antibody titer of each individual in the vaccine administration group and the control group (non-administration group), respectively. As shown in FIG. 26, the level of the IgG antibody against IgE was confirmed to elevate in the dogs (artificially sensitized adult dogs as in test 4 and test 5) by the administration of the vaccine. In addition, 4 or less shots were also confirmed to suffice for the frequency of administration, as in the foregoing tests.

FIG. 27 shows the results of assaying *Dermatophagoides farinae* antigen-specific IgE by ELISA. FIG. 27A shows the average antibody titers of the peptide vaccine administration group and the control group. FIG. 27B and FIG. 27C show the antibody titer of each individual in the vaccine administration group and the control group (non-administration group), respectively. As shown in FIG. 27, reduction in the serum concentration of IgE was confirmed in one individual (04-95) in the vaccine (M4-7-11) administration group. This suggests that the serum concentration of IgE may be reduced by the administration of the vaccine (M4-7-11).

INDUSTRIAL APPLICABILITY

The partial peptide of mouse IgE of the present invention can be used as a drug for preventing or treating IgE-mediated allergic diseases in animals.

All publications, patents, and patent applications are incorporated herein by reference in their entirety.

The invention claimed is:

1. A vaccine or therapeutic agent for an IgE-mediated disease in a human or dog comprising:
   A) an adjuvant; and
   B) a peptide consisting of the amino acid sequence represented by SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 38, SEQ ID NO: 42, SEQ ID NO: 45, or SEQ ID NO: 55.

2. The vaccine according to claim 1, wherein the adjuvant is selected from the group consisting of Fruend's adjuvants, bacteria and their cell components, mycobacteria, gram-negative bacteria and their cell components, gram-positive bacteria and their cell components, plant or fungus polysaccharides, fat-soluble vitamins, mineral oils, calcium phosphate adjuvant, aluminum phosphate adjuvant, and alum.

3. The vaccine or therapeutic agent according to claim 1, wherein the IgE-mediated disease is selected from the group consisting of atopic dermatitis, pollinosis, food allergy, allergic rhinitis, bronchial asthma, allergic conjunctivitis, mite allergy, hives, anaphylactic shock, and PIE (pulmonary infiltration with eosinophilia) syndrome.

4. A method for treating an IgE-mediated disease, comprising administering the vaccine according to claim 1 to a mammal other than a mouse.

5. The method for treating an IgE-mediated disease according to claim 4, wherein the IgE-mediated disease is selected from the group consisting of atopic dermatitis, pollinosis, food allergy, allergic rhinitis, bronchial asthma, allergic conjunctivitis, mite allergy, hives, anaphylactic shock, and PIE (pulmonary infiltration with eosinophilia) syndrome.

6. A vaccine or therapeutic agent for an IgE-mediated disease in a human or dog comprising:
   A) an adjuvant; and
   B) a peptide consisting of
      (i) the amino acid sequence represented by SEQ ID NO: 28.

* * * * *

SEQUENCE LISTING

```
<160> NUMBER OF SEQ ID NOS: 92

<210> SEQ ID NO 1
<211> LENGTH: 107
<212> TYPE: PRT
<213> ORGANISM: Canis lupus familiaris

<400> SEQUENCE: 1

Glu Ser Asp Pro Arg Gly Val Ser Ser Tyr Leu Ser Pro Pro Ser Pro
1               5                   10                  15

Leu Asp Leu Tyr Val His Lys Ala Pro Lys Ile Thr Cys Leu Val Val
            20                  25                  30
```

Asp Leu Ala Thr Met Glu Gly Met Asn Leu Thr Trp Tyr Arg Glu Ser
            35                  40                  45

Lys Glu Pro Val Asn Pro Gly Pro Leu Asn Lys Lys Asp His Phe Asn
 50                  55                  60

Gly Thr Ile Thr Val Thr Ser Thr Leu Pro Val Asn Thr Asn Asp Trp
 65                  70                  75                  80

Ile Glu Gly Glu Thr Tyr Tyr Cys Arg Val Thr His Pro His Leu Pro
                 85                  90                  95

Lys Asp Ile Val Arg Ser Ile Ala Lys Ala Pro
            100                 105

<210> SEQ ID NO 2
<211> LENGTH: 15
<212> TYPE: PRT
<213> ORGANISM: Canis lupus familiaris

<400> SEQUENCE: 2

Glu Ser Asp Pro Arg Gly Val Ser Ser Tyr Leu Ser Pro Pro Ser
 1               5                  10                  15

<210> SEQ ID NO 3
<211> LENGTH: 15
<212> TYPE: PRT
<213> ORGANISM: Canis lupus familiaris

<400> SEQUENCE: 3

Gly Val Ser Ser Tyr Leu Ser Pro Pro Ser Pro Leu Asp Leu Tyr
 1               5                  10                  15

<210> SEQ ID NO 4
<211> LENGTH: 15
<212> TYPE: PRT
<213> ORGANISM: Canis lupus familiaris

<400> SEQUENCE: 4

Leu Ser Pro Pro Ser Pro Leu Asp Leu Tyr Val His Lys Ala Pro
 1               5                  10                  15

<210> SEQ ID NO 5
<211> LENGTH: 15
<212> TYPE: PRT
<213> ORGANISM: Canis lupus familiaris

<400> SEQUENCE: 5

Pro Leu Asp Leu Tyr Val His Lys Ala Pro Lys Ile Thr Cys Leu
 1               5                  10                  15

<210> SEQ ID NO 6
<211> LENGTH: 15
<212> TYPE: PRT
<213> ORGANISM: Canis lupus familiaris

<400> SEQUENCE: 6

Val His Lys Ala Pro Lys Ile Thr Cys Leu Val Val Asp Leu Ala
 1               5                  10                  15

<210> SEQ ID NO 7
<211> LENGTH: 15
<212> TYPE: PRT
<213> ORGANISM: Canis lupus familiaris

<400> SEQUENCE: 7

Lys Ile Thr Cys Leu Val Val Asp Leu Ala Thr Met Glu Gly Met

```
1               5                   10                  15
```

<210> SEQ ID NO 8
<211> LENGTH: 15
<212> TYPE: PRT
<213> ORGANISM: Canis lupus familiaris

<400> SEQUENCE: 8

```
Val Val Asp Leu Ala Thr Met Glu Gly Met Asn Leu Thr Trp Tyr
1               5                   10                  15
```

<210> SEQ ID NO 9
<211> LENGTH: 15
<212> TYPE: PRT
<213> ORGANISM: Canis lupus familiaris

<400> SEQUENCE: 9

```
Thr Met Glu Gly Met Asn Leu Thr Trp Tyr Arg Glu Ser Lys Glu
1               5                   10                  15
```

<210> SEQ ID NO 10
<211> LENGTH: 15
<212> TYPE: PRT
<213> ORGANISM: Canis lupus familiaris

<400> SEQUENCE: 10

```
Asn Leu Thr Trp Tyr Arg Glu Ser Lys Glu Pro Val Asn Pro Gly
1               5                   10                  15
```

<210> SEQ ID NO 11
<211> LENGTH: 15
<212> TYPE: PRT
<213> ORGANISM: Canis lupus familiaris

<400> SEQUENCE: 11

```
Arg Glu Ser Lys Glu Pro Val Asn Pro Gly Pro Leu Asn Lys Lys
1               5                   10                  15
```

<210> SEQ ID NO 12
<211> LENGTH: 15
<212> TYPE: PRT
<213> ORGANISM: Canis lupus familiaris

<400> SEQUENCE: 12

```
Pro Val Asn Pro Gly Pro Leu Asn Lys Lys Asp His Phe Asn Gly
1               5                   10                  15
```

<210> SEQ ID NO 13
<211> LENGTH: 15
<212> TYPE: PRT
<213> ORGANISM: Canis lupus familiaris

<400> SEQUENCE: 13

```
Pro Leu Asn Lys Lys Asp His Phe Asn Gly Thr Ile Thr Val Thr
1               5                   10                  15
```

<210> SEQ ID NO 14
<211> LENGTH: 15
<212> TYPE: PRT
<213> ORGANISM: Canis lupus familiaris

<400> SEQUENCE: 14

```
Asp His Phe Asn Gly Thr Ile Thr Val Thr Ser Thr Leu Pro Val
1               5                   10                  15
```

<210> SEQ ID NO 15
<211> LENGTH: 15
<212> TYPE: PRT
<213> ORGANISM: Canis lupus familiaris

<400> SEQUENCE: 15

Thr Ile Thr Val Thr Ser Thr Leu Pro Val Asn Thr Asn Asp Trp
1               5                   10                  15

<210> SEQ ID NO 16
<211> LENGTH: 15
<212> TYPE: PRT
<213> ORGANISM: Canis lupus familiaris

<400> SEQUENCE: 16

Ser Thr Leu Pro Val Asn Thr Asn Asp Trp Ile Glu Gly Glu Thr
1               5                   10                  15

<210> SEQ ID NO 17
<211> LENGTH: 15
<212> TYPE: PRT
<213> ORGANISM: Canis lupus familiaris

<400> SEQUENCE: 17

Asn Thr Asn Asp Trp Ile Glu Gly Glu Thr Tyr Tyr Cys Arg Val
1               5                   10                  15

<210> SEQ ID NO 18
<211> LENGTH: 15
<212> TYPE: PRT
<213> ORGANISM: Canis lupus familiaris

<400> SEQUENCE: 18

Ile Glu Gly Glu Thr Tyr Tyr Cys Arg Val Thr His Pro His Leu
1               5                   10                  15

<210> SEQ ID NO 19
<211> LENGTH: 15
<212> TYPE: PRT
<213> ORGANISM: Canis lupus familiaris

<400> SEQUENCE: 19

Tyr Tyr Cys Arg Val Thr His Pro His Leu Pro Lys Asp Ile Val
1               5                   10                  15

<210> SEQ ID NO 20
<211> LENGTH: 17
<212> TYPE: PRT
<213> ORGANISM: Canis lupus familiaris

<400> SEQUENCE: 20

Thr His Pro His Leu Pro Lys Asp Ile Val Arg Ser Ile Ala Lys Ala
1               5                   10                  15

Pro

<210> SEQ ID NO 21
<211> LENGTH: 107
<212> TYPE: PRT
<213> ORGANISM: Mus musculus

<400> SEQUENCE: 21

His Glu Pro Arg Gly Val Ile Thr Tyr Leu Ile Pro Pro Ser Pro Leu
1               5                   10                  15

Asp Leu Tyr Gln Asn Gly Ala Pro Lys Leu Thr Cys Leu Val Val Asp
            20                  25                  30

Leu Glu Ser Glu Lys Asn Val Asn Val Thr Trp Asn Gln Glu Lys Lys
        35                  40                  45

Thr Ser Val Ser Ala Ser Gln Trp Tyr Thr Lys His His Asn Asn Ala
    50                  55                  60

Thr Thr Ser Ile Thr Ser Ile Leu Pro Val Val Ala Lys Asp Trp Ile
65                  70                  75                  80

Glu Gly Tyr Gly Tyr Gln Cys Ile Val Asp His Pro Asp Phe Pro Lys
                85                  90                  95

Pro Ile Val Arg Ser Ile Thr Lys Thr Pro Gln
            100                 105

<210> SEQ ID NO 22
<211> LENGTH: 15
<212> TYPE: PRT
<213> ORGANISM: Mus musculus

<400> SEQUENCE: 22

Asn Val Thr Trp Asn Gln Glu Lys Lys Thr Ser Val Ser Ala Ser
1               5                   10                  15

<210> SEQ ID NO 23
<211> LENGTH: 15
<212> TYPE: PRT
<213> ORGANISM: Mus musculus

<400> SEQUENCE: 23

Gln Glu Lys Lys Thr Ser Val Ser Ala Ser Gln Trp Tyr Thr Lys
1               5                   10                  15

<210> SEQ ID NO 24
<211> LENGTH: 15
<212> TYPE: PRT
<213> ORGANISM: Mus musculus

<400> SEQUENCE: 24

Ser Val Ser Ala Ser Gln Trp Tyr Thr Lys His His Asn Asn Ala
1               5                   10                  15

<210> SEQ ID NO 25
<211> LENGTH: 15
<212> TYPE: PRT
<213> ORGANISM: Mus musculus

<400> SEQUENCE: 25

Gln Trp Tyr Thr Lys His His Asn Asn Ala Thr Thr Ser Ile Thr
1               5                   10                  15

<210> SEQ ID NO 26
<211> LENGTH: 15
<212> TYPE: PRT
<213> ORGANISM: Mus musculus

<400> SEQUENCE: 26

His His Asn Asn Ala Thr Thr Ser Ile Thr Ser Ile Leu Pro Val
1               5                   10                  15

<210> SEQ ID NO 27
<211> LENGTH: 25
<212> TYPE: PRT
<213> ORGANISM: Mus musculus

```
<400> SEQUENCE: 27

Gln Glu Lys Lys Thr Ser Val Ser Ala Ser Gln Trp Tyr Thr Lys His
1               5                   10                  15

His Asn Asn Ala Thr Thr Ser Ile Thr
            20                  25

<210> SEQ ID NO 28
<211> LENGTH: 35
<212> TYPE: PRT
<213> ORGANISM: Mus musculus

<400> SEQUENCE: 28

Asn Val Thr Trp Asn Gln Glu Lys Lys Thr Ser Val Ser Ala Ser Gln
1               5                   10                  15

Trp Tyr Thr Lys His His Asn Asn Ala Thr Thr Ser Ile Thr Ser Ile
            20                  25                  30

Leu Pro Val
        35

<210> SEQ ID NO 29
<211> LENGTH: 24
<212> TYPE: PRT
<213> ORGANISM: Mus musculus

<400> SEQUENCE: 29

Gln Glu Lys Lys Thr Ser Val Ser Ala Ser Gln Trp Tyr Thr Lys His
1               5                   10                  15

His Asn Asn Ala Thr Thr Ser Ile
            20

<210> SEQ ID NO 30
<211> LENGTH: 24
<212> TYPE: PRT
<213> ORGANISM: Mus musculus

<400> SEQUENCE: 30

Glu Lys Lys Thr Ser Val Ser Ala Ser Gln Trp Tyr Thr Lys His His
1               5                   10                  15

Asn Asn Ala Thr Thr Ser Ile Thr
            20

<210> SEQ ID NO 31
<211> LENGTH: 23
<212> TYPE: PRT
<213> ORGANISM: Mus musculus

<400> SEQUENCE: 31

Gln Glu Lys Lys Thr Ser Val Ser Ala Ser Gln Trp Tyr Thr Lys His
1               5                   10                  15

His Asn Asn Ala Thr Thr Ser
            20

<210> SEQ ID NO 32
<211> LENGTH: 23
<212> TYPE: PRT
<213> ORGANISM: Mus musculus

<400> SEQUENCE: 32

Glu Lys Lys Thr Ser Val Ser Ala Ser Gln Trp Tyr Thr Lys His His
1               5                   10                  15

Asn Asn Ala Thr Thr Ser Ile
```

20

<210> SEQ ID NO 33
<211> LENGTH: 23
<212> TYPE: PRT
<213> ORGANISM: Mus musculus

<400> SEQUENCE: 33

Lys Lys Thr Ser Val Ser Ala Ser Gln Trp Tyr Thr Lys His His Asn
1               5                   10                  15

Asn Ala Thr Thr Ser Ile Thr
            20

<210> SEQ ID NO 34
<211> LENGTH: 22
<212> TYPE: PRT
<213> ORGANISM: Mus musculus

<400> SEQUENCE: 34

Gln Glu Lys Lys Thr Ser Val Ser Ala Ser Gln Trp Tyr Thr Lys His
1               5                   10                  15

His Asn Asn Ala Thr Thr
            20

<210> SEQ ID NO 35
<211> LENGTH: 22
<212> TYPE: PRT
<213> ORGANISM: Mus musculus

<400> SEQUENCE: 35

Glu Lys Lys Thr Ser Val Ser Ala Ser Gln Trp Tyr Thr Lys His His
1               5                   10                  15

Asn Asn Ala Thr Thr Ser
            20

<210> SEQ ID NO 36
<211> LENGTH: 22
<212> TYPE: PRT
<213> ORGANISM: Mus musculus

<400> SEQUENCE: 36

Lys Lys Thr Ser Val Ser Ala Ser Gln Trp Tyr Thr Lys His His Asn
1               5                   10                  15

Asn Ala Thr Thr Ser Ile
            20

<210> SEQ ID NO 37
<211> LENGTH: 22
<212> TYPE: PRT
<213> ORGANISM: Mus musculus

<400> SEQUENCE: 37

Lys Thr Ser Val Ser Ala Ser Gln Trp Tyr Thr Lys His His Asn Asn
1               5                   10                  15

Ala Thr Thr Ser Ile Thr
            20

<210> SEQ ID NO 38
<211> LENGTH: 21
<212> TYPE: PRT
<213> ORGANISM: Mus musculus

<400> SEQUENCE: 38

Gln Glu Lys Lys Thr Ser Val Ser Ala Ser Gln Trp Tyr Thr Lys His
1               5                   10                  15

His Asn Asn Ala Thr
            20

<210> SEQ ID NO 39
<211> LENGTH: 21
<212> TYPE: PRT
<213> ORGANISM: Mus musculus

<400> SEQUENCE: 39

Glu Lys Lys Thr Ser Val Ser Ala Ser Gln Trp Tyr Thr Lys His His
1               5                   10                  15

Asn Asn Ala Thr Thr
            20

<210> SEQ ID NO 40
<211> LENGTH: 21
<212> TYPE: PRT
<213> ORGANISM: Mus musculus

<400> SEQUENCE: 40

Lys Lys Thr Ser Val Ser Ala Ser Gln Trp Tyr Thr Lys His His Asn
1               5                   10                  15

Asn Ala Thr Thr Ser
            20

<210> SEQ ID NO 41
<211> LENGTH: 21
<212> TYPE: PRT
<213> ORGANISM: Mus musculus

<400> SEQUENCE: 41

Lys Thr Ser Val Ser Ala Ser Gln Trp Tyr Thr Lys His His Asn Asn
1               5                   10                  15

Ala Thr Thr Ser Ile
            20

<210> SEQ ID NO 42
<211> LENGTH: 21
<212> TYPE: PRT
<213> ORGANISM: Mus musculus

<400> SEQUENCE: 42

Thr Ser Val Ser Ala Ser Gln Trp Tyr Thr Lys His His Asn Asn Ala
1               5                   10                  15

Thr Thr Ser Ile Thr
            20

<210> SEQ ID NO 43
<211> LENGTH: 20
<212> TYPE: PRT
<213> ORGANISM: Mus musculus

<400> SEQUENCE: 43

Gln Glu Lys Lys Thr Ser Val Ser Ala Ser Gln Trp Tyr Thr Lys His
1               5                   10                  15

His Asn Asn Ala
            20

<210> SEQ ID NO 44

<211> LENGTH: 20
<212> TYPE: PRT
<213> ORGANISM: Mus musculus

<400> SEQUENCE: 44

Glu Lys Lys Thr Ser Val Ser Ala Ser Gln Trp Tyr Thr Lys His His
1               5                   10                  15

Asn Asn Ala Thr
            20

<210> SEQ ID NO 45
<211> LENGTH: 20
<212> TYPE: PRT
<213> ORGANISM: Mus musculus

<400> SEQUENCE: 45

Lys Lys Thr Ser Val Ser Ala Ser Gln Trp Tyr Thr Lys His His Asn
1               5                   10                  15

Asn Ala Thr Thr
            20

<210> SEQ ID NO 46
<211> LENGTH: 20
<212> TYPE: PRT
<213> ORGANISM: Mus musculus

<400> SEQUENCE: 46

Lys Thr Ser Val Ser Ala Ser Gln Trp Tyr Thr Lys His His Asn Asn
1               5                   10                  15

Ala Thr Thr Ser
            20

<210> SEQ ID NO 47
<211> LENGTH: 20
<212> TYPE: PRT
<213> ORGANISM: Mus musculus

<400> SEQUENCE: 47

Thr Ser Val Ser Ala Ser Gln Trp Tyr Thr Lys His His Asn Asn Ala
1               5                   10                  15

Thr Thr Ser Ile
            20

<210> SEQ ID NO 48
<211> LENGTH: 20
<212> TYPE: PRT
<213> ORGANISM: Mus musculus

<400> SEQUENCE: 48

Ser Val Ser Ala Ser Gln Trp Tyr Thr Lys His His Asn Asn Ala Thr
1               5                   10                  15

Thr Ser Ile Thr
            20

<210> SEQ ID NO 49
<211> LENGTH: 19
<212> TYPE: PRT
<213> ORGANISM: Mus musculus

<400> SEQUENCE: 49

Gln Glu Lys Lys Thr Ser Val Ser Ala Ser Gln Trp Tyr Thr Lys His
1               5                   10                  15

His Asn Asn

<210> SEQ ID NO 50
<211> LENGTH: 19
<212> TYPE: PRT
<213> ORGANISM: Mus musculus

<400> SEQUENCE: 50

Glu Lys Lys Thr Ser Val Ser Ala Ser Gln Trp Tyr Thr Lys His His
1               5                   10                  15

Asn Asn Ala

<210> SEQ ID NO 51
<211> LENGTH: 19
<212> TYPE: PRT
<213> ORGANISM: Mus musculus

<400> SEQUENCE: 51

Lys Lys Thr Ser Val Ser Ala Ser Gln Trp Tyr Thr Lys His His Asn
1               5                   10                  15

Asn Ala Thr

<210> SEQ ID NO 52
<211> LENGTH: 19
<212> TYPE: PRT
<213> ORGANISM: Mus musculus

<400> SEQUENCE: 52

Lys Thr Ser Val Ser Ala Ser Gln Trp Tyr Thr Lys His His Asn Asn
1               5                   10                  15

Ala Thr Thr

<210> SEQ ID NO 53
<211> LENGTH: 19
<212> TYPE: PRT
<213> ORGANISM: Mus musculus

<400> SEQUENCE: 53

Thr Ser Val Ser Ala Ser Gln Trp Tyr Thr Lys His His Asn Asn Ala
1               5                   10                  15

Thr Thr Ser

<210> SEQ ID NO 54
<211> LENGTH: 19
<212> TYPE: PRT
<213> ORGANISM: Mus musculus

<400> SEQUENCE: 54

Ser Val Ser Ala Ser Gln Trp Tyr Thr Lys His His Asn Asn Ala Thr
1               5                   10                  15

Thr Ser Ile

<210> SEQ ID NO 55
<211> LENGTH: 19
<212> TYPE: PRT
<213> ORGANISM: Mus musculus

<400> SEQUENCE: 55

Val Ser Ala Ser Gln Trp Tyr Thr Lys His His Asn Asn Ala Thr Thr
1               5                   10                  15

Ser Ile Thr

```
<210> SEQ ID NO 56
<211> LENGTH: 18
<212> TYPE: PRT
<213> ORGANISM: Mus musculus

<400> SEQUENCE: 56

Gln Glu Lys Lys Thr Ser Val Ser Ala Ser Gln Trp Tyr Thr Lys His
1               5                   10                  15

His Asn

<210> SEQ ID NO 57
<211> LENGTH: 18
<212> TYPE: PRT
<213> ORGANISM: Mus musculus

<400> SEQUENCE: 57

Glu Lys Lys Thr Ser Val Ser Ala Ser Gln Trp Tyr Thr Lys His His
1               5                   10                  15

Asn Asn

<210> SEQ ID NO 58
<211> LENGTH: 18
<212> TYPE: PRT
<213> ORGANISM: Mus musculus

<400> SEQUENCE: 58

Lys Lys Thr Ser Val Ser Ala Ser Gln Trp Tyr Thr Lys His His Asn
1               5                   10                  15

Asn Ala

<210> SEQ ID NO 59
<211> LENGTH: 18
<212> TYPE: PRT
<213> ORGANISM: Mus musculus

<400> SEQUENCE: 59

Lys Thr Ser Val Ser Ala Ser Gln Trp Tyr Thr Lys His His Asn Asn
1               5                   10                  15

Ala Thr

<210> SEQ ID NO 60
<211> LENGTH: 18
<212> TYPE: PRT
<213> ORGANISM: Mus musculus

<400> SEQUENCE: 60

Thr Ser Val Ser Ala Ser Gln Trp Tyr Thr Lys His His Asn Asn Ala
1               5                   10                  15

Thr Thr

<210> SEQ ID NO 61
<211> LENGTH: 18
<212> TYPE: PRT
<213> ORGANISM: Mus musculus

<400> SEQUENCE: 61

Ser Val Ser Ala Ser Gln Trp Tyr Thr Lys His His Asn Asn Ala Thr
1               5                   10                  15

Thr Ser
```

```
<210> SEQ ID NO 62
<211> LENGTH: 18
<212> TYPE: PRT
<213> ORGANISM: Mus musculus

<400> SEQUENCE: 62

Val Ser Ala Ser Gln Trp Tyr Thr Lys His His Asn Asn Ala Thr Thr
1               5                   10                  15

Ser Ile

<210> SEQ ID NO 63
<211> LENGTH: 18
<212> TYPE: PRT
<213> ORGANISM: Mus musculus

<400> SEQUENCE: 63

Ser Ala Ser Gln Trp Tyr Thr Lys His His Asn Asn Ala Thr Thr Ser
1               5                   10                  15

Ile Thr

<210> SEQ ID NO 64
<211> LENGTH: 17
<212> TYPE: PRT
<213> ORGANISM: Mus musculus

<400> SEQUENCE: 64

Gln Glu Lys Lys Thr Ser Val Ser Ala Ser Gln Trp Tyr Thr Lys His
1               5                   10                  15

His

<210> SEQ ID NO 65
<211> LENGTH: 17
<212> TYPE: PRT
<213> ORGANISM: Mus musculus

<400> SEQUENCE: 65

Glu Lys Lys Thr Ser Val Ser Ala Ser Gln Trp Tyr Thr Lys His His
1               5                   10                  15

Asn

<210> SEQ ID NO 66
<211> LENGTH: 17
<212> TYPE: PRT
<213> ORGANISM: Mus musculus

<400> SEQUENCE: 66

Lys Lys Thr Ser Val Ser Ala Ser Gln Trp Tyr Thr Lys His His Asn
1               5                   10                  15

Asn

<210> SEQ ID NO 67
<211> LENGTH: 17
<212> TYPE: PRT
<213> ORGANISM: Mus musculus

<400> SEQUENCE: 67

Lys Thr Ser Val Ser Ala Ser Gln Trp Tyr Thr Lys His His Asn Asn
1               5                   10                  15

Ala
```

```
<210> SEQ ID NO 68
<211> LENGTH: 17
<212> TYPE: PRT
<213> ORGANISM: Mus musculus

<400> SEQUENCE: 68

Ser Val Ser Ala Ser Gln Trp Tyr Thr Lys His His Asn Asn Ala Thr
 1               5                  10                  15
Thr

<210> SEQ ID NO 69
<211> LENGTH: 17
<212> TYPE: PRT
<213> ORGANISM: Mus musculus

<400> SEQUENCE: 69

Val Ser Ala Ser Gln Trp Tyr Thr Lys His His Asn Asn Ala Thr Thr
 1               5                  10                  15
Ser

<210> SEQ ID NO 70
<211> LENGTH: 17
<212> TYPE: PRT
<213> ORGANISM: Mus musculus

<400> SEQUENCE: 70

Ser Ala Ser Gln Trp Tyr Thr Lys His His Asn Asn Ala Thr Thr Ser
 1               5                  10                  15
Ile

<210> SEQ ID NO 71
<211> LENGTH: 17
<212> TYPE: PRT
<213> ORGANISM: Mus musculus

<400> SEQUENCE: 71

Ala Ser Gln Trp Tyr Thr Lys His His Asn Asn Ala Thr Thr Ser Ile
 1               5                  10                  15
Thr

<210> SEQ ID NO 72
<211> LENGTH: 16
<212> TYPE: PRT
<213> ORGANISM: Mus musculus

<400> SEQUENCE: 72

Gln Glu Lys Lys Thr Ser Val Ser Ala Ser Gln Trp Tyr Thr Lys His
 1               5                  10                  15

<210> SEQ ID NO 73
<211> LENGTH: 16
<212> TYPE: PRT
<213> ORGANISM: Mus musculus

<400> SEQUENCE: 73

Glu Lys Lys Thr Ser Val Ser Ala Ser Gln Trp Tyr Thr Lys His His
 1               5                  10                  15

<210> SEQ ID NO 74
<211> LENGTH: 16
<212> TYPE: PRT
<213> ORGANISM: Mus musculus
```

```
<400> SEQUENCE: 74

Lys Lys Thr Ser Val Ser Ala Ser Gln Trp Tyr Thr Lys His His Asn
1               5                   10                  15

<210> SEQ ID NO 75
<211> LENGTH: 16
<212> TYPE: PRT
<213> ORGANISM: Mus musculus

<400> SEQUENCE: 75

Lys Thr Ser Val Ser Ala Ser Gln Trp Tyr Thr Lys His His Asn Asn
1               5                   10                  15

<210> SEQ ID NO 76
<211> LENGTH: 16
<212> TYPE: PRT
<213> ORGANISM: Mus musculus

<400> SEQUENCE: 76

Thr Ser Val Ser Ala Ser Gln Trp Tyr Thr Lys His His Asn Asn Ala
1               5                   10                  15

<210> SEQ ID NO 77
<211> LENGTH: 16
<212> TYPE: PRT
<213> ORGANISM: Mus musculus

<400> SEQUENCE: 77

Ser Val Ser Ala Ser Gln Trp Tyr Thr Lys His His Asn Asn Ala Thr
1               5                   10                  15

<210> SEQ ID NO 78
<211> LENGTH: 16
<212> TYPE: PRT
<213> ORGANISM: Mus musculus

<400> SEQUENCE: 78

Val Ser Ala Ser Gln Trp Tyr Thr Lys His His Asn Asn Ala Thr Thr
1               5                   10                  15

<210> SEQ ID NO 79
<211> LENGTH: 16
<212> TYPE: PRT
<213> ORGANISM: Mus musculus

<400> SEQUENCE: 79

Ser Ala Ser Gln Trp Tyr Thr Lys His His Asn Asn Ala Thr Thr Ser
1               5                   10                  15

<210> SEQ ID NO 80
<211> LENGTH: 16
<212> TYPE: PRT
<213> ORGANISM: Mus musculus

<400> SEQUENCE: 80

Ala Ser Gln Trp Tyr Thr Lys His His Asn Asn Ala Thr Thr Ser Ile
1               5                   10                  15

<210> SEQ ID NO 81
<211> LENGTH: 16
<212> TYPE: PRT
<213> ORGANISM: Mus musculus

<400> SEQUENCE: 81
```

Ser Gln Trp Tyr Thr Lys His His Asn Asn Ala Thr Thr Ser Ile Thr
1               5                   10                  15

<210> SEQ ID NO 82
<211> LENGTH: 15
<212> TYPE: PRT
<213> ORGANISM: Mus musculus

<400> SEQUENCE: 82

Gln Glu Lys Lys Thr Ser Val Ser Ala Ser Gln Trp Tyr Thr Lys
1               5                   10                  15

<210> SEQ ID NO 83
<211> LENGTH: 15
<212> TYPE: PRT
<213> ORGANISM: Mus musculus

<400> SEQUENCE: 83

Glu Lys Lys Thr Ser Val Ser Ala Ser Gln Trp Tyr Thr Lys His
1               5                   10                  15

<210> SEQ ID NO 84
<211> LENGTH: 15
<212> TYPE: PRT
<213> ORGANISM: Mus musculus

<400> SEQUENCE: 84

Lys Lys Thr Ser Val Ser Ala Ser Gln Trp Tyr Thr Lys His His
1               5                   10                  15

<210> SEQ ID NO 85
<211> LENGTH: 15
<212> TYPE: PRT
<213> ORGANISM: Mus musculus

<400> SEQUENCE: 85

Lys Thr Ser Val Ser Ala Ser Gln Trp Tyr Thr Lys His His Asn
1               5                   10                  15

<210> SEQ ID NO 86
<211> LENGTH: 15
<212> TYPE: PRT
<213> ORGANISM: Mus musculus

<400> SEQUENCE: 86

Thr Ser Val Ser Ala Ser Gln Trp Tyr Thr Lys His His Asn Asn
1               5                   10                  15

<210> SEQ ID NO 87
<211> LENGTH: 15
<212> TYPE: PRT
<213> ORGANISM: Mus musculus

<400> SEQUENCE: 87

Ser Val Ser Ala Ser Gln Trp Tyr Thr Lys His His Asn Asn Ala
1               5                   10                  15

<210> SEQ ID NO 88
<211> LENGTH: 15
<212> TYPE: PRT
<213> ORGANISM: Mus musculus

<400> SEQUENCE: 88

Val Ser Ala Ser Gln Trp Tyr Thr Lys His His Asn Asn Ala Thr
1               5                   10                  15

```
<210> SEQ ID NO 89
<211> LENGTH: 15
<212> TYPE: PRT
<213> ORGANISM: Mus musculus

<400> SEQUENCE: 89

Ser Ala Ser Gln Trp Tyr Thr Lys His His Asn Asn Ala Thr Thr
1               5                   10                  15

<210> SEQ ID NO 90
<211> LENGTH: 15
<212> TYPE: PRT
<213> ORGANISM: Mus musculus

<400> SEQUENCE: 90

Ala Ser Gln Trp Tyr Thr Lys His His Asn Asn Ala Thr Thr Ser
1               5                   10                  15

<210> SEQ ID NO 91
<211> LENGTH: 15
<212> TYPE: PRT
<213> ORGANISM: Mus musculus

<400> SEQUENCE: 91

Ser Gln Trp Tyr Thr Lys His His Asn Asn Ala Thr Thr Ser Ile
1               5                   10                  15

<210> SEQ ID NO 92
<211> LENGTH: 15
<212> TYPE: PRT
<213> ORGANISM: Mus musculus

<400> SEQUENCE: 92

Gln Trp Tyr Thr Lys His His Asn Asn Ala Thr Thr Ser Ile Thr
1               5                   10                  15
```